(12) United States Patent
Hyde et al.

(10) Patent No.: US 10,780,017 B2
(45) Date of Patent: *Sep. 22, 2020

(54) TREATING SLEEP APNEA WITH NEGATIVE PRESSURE

(71) Applicant: Elwha LLC, Bellevue, WA (US)

(72) Inventors: Roderick A. Hyde, Redmond, WA (US); Kenneth G. Caldeira, Redwood City, CA (US); Gary L. McKnight, Bothell, WA (US); Lowell L. Wood, Jr., Bellevue, WA (US); Dennis J. Rivet, Chesapeake, VA (US); Katherine A. Sharadin, Redmond, WA (US); Michael A. Smith, Phoenix, AZ (US)

(73) Assignee: Somne LLC, Bellevue, WA (US)

( * ) Notice: Subject to any disclaimer, the term of this patent is extended or adjusted under 35 U.S.C. 154(b) by 484 days.

This patent is subject to a terminal disclaimer.

(21) Appl. No.: 15/406,379

(22) Filed: Jan. 13, 2017

(65) Prior Publication Data

US 2017/0196761 A1 Jul. 13, 2017

Related U.S. Application Data

(63) Continuation-in-part of application No. 13/839,933, filed on Mar. 15, 2013, now Pat. No. 10,548,760, and
(Continued)

(51) Int. Cl.
*A61H 9/00* (2006.01)
*A61B 5/0205* (2006.01)
(Continued)

(52) U.S. Cl.
CPC ......... *A61H 9/0057* (2013.01); *A61B 5/0205* (2013.01); *A61B 5/4818* (2013.01);
(Continued)

(58) Field of Classification Search
CPC ................... A61H 9/0057; A61F 5/56; A61M 16/06–0655; A61M 16/0683–0694
See application file for complete search history.

(56) References Cited

U.S. PATENT DOCUMENTS 5,123,425 A 6/1992 Shannon, Jr. et al.
5,199,424 A 4/1993 Sullivan et al.
(Continued)

FOREIGN PATENT DOCUMENTS

WO 03006095 1/2003

OTHER PUBLICATIONS

PCT International Search Report; International App. No. PCT/2018/013465; dated May 3, 2018; pp. 1-4.
(Continued)

*Primary Examiner* — Valerie L Woodward
(74) *Attorney, Agent, or Firm* — Fogg & Powers LLC

(57) ABSTRACT

An embodiment of a system for treating sleep apnea includes a collar, a pump, a motor, a sensor, and a controller. The collar is configured to maintain an airway of a subject open while the subject is sleeping by applying, to a throat of the subject, a negative pressure having a magnitude, and the pump is configured to generate the negative pressure. The motor is configured to drive the pump, and the sensor is configured to generate a sense signal that is related to a degree to which the airway is open. And the controller is configured to vary the magnitude of the negative pressure in response to the sense signal. For example, one or more of the pump, motor, sensor, and controller can be secured to the collar such that the system is self-contained, i.e., the entire sleep-apnea system can be worn by the subject.

31 Claims, 35 Drawing Sheets

Related U.S. Application Data a continuation-in-part of application No. 13/840,374, filed on Mar. 15, 2013, and a continuation-in-part of application No. 13/840,189, filed on Mar. 15, 2013, now Pat. No. 9,655,766, and a continuation-in-part of application No. 13/839,605, filed on Mar. 15, 2013, now Pat. No. 9,707,121.

(51) Int. Cl.
| | | |
|---|---|---|
| A61M 16/00 | (2006.01) | |
| A61B 5/00 | (2006.01) | |
| A61B 7/00 | (2006.01) | |
| A61F 5/56 | (2006.01) | |
| A61B 5/1455 | (2006.01) | |
| A61B 5/08 | (2006.01) | |

(52) U.S. Cl.
CPC .......... *A61B 5/4836* (2013.01); *A61B 5/6822* (2013.01); *A61B 7/003* (2013.01); *A61F 5/56* (2013.01); *A61M 16/0009* (2014.02); *A61M 16/0051* (2013.01); *A61M 16/0069* (2014.02); *A61M 16/026* (2017.08); *A61B 5/0816* (2013.01); *A61B 5/14551* (2013.01); *A61H 9/0078* (2013.01); *A61H 2201/0192* (2013.01); *A61H 2201/0207* (2013.01); *A61H 2201/0214* (2013.01); *A61H 2201/0228* (2013.01); *A61H 2201/10* (2013.01); *A61H 2201/165* (2013.01); *A61H 2201/1609* (2013.01); *A61H 2201/1654* (2013.01); *A61H 2201/5002* (2013.01); *A61H 2201/5064* (2013.01); *A61H 2201/5071* (2013.01); *A61H 2201/5092* (2013.01); *A61H 2201/5097* (2013.01); *A61H 2230/00* (2013.01); *A61H 2230/06* (2013.01); *A61H 2230/202* (2013.01); *A61H 2230/30* (2013.01); *A61H 2230/42* (2013.01); *A61H 2230/50* (2013.01); *A61M 2205/15* (2013.01); *A61M 2205/332* (2013.01); *A61M 2205/3306* (2013.01); *A61M 2205/3368* (2013.01); *A61M 2205/3375* (2013.01); *A61M 2205/3606* (2013.01); *A61M 2205/3653* (2013.01); *A61M 2205/42* (2013.01); *A61M 2205/8206* (2013.01); *A61M 2210/1028* (2013.01); *A61M 2210/1032* (2013.01)

(56) References Cited

U.S. PATENT DOCUMENTS

| | | | | |
|---|---|---|---|---|
| 5,275,159 | A * | 1/1994 | Griebel | A61B 5/0205 600/324 |
| 5,309,921 | A * | 5/1994 | Kisner | A61B 5/0064 128/925 |
| 5,343,878 | A | 9/1994 | Scarberry et al. | |
| 5,891,065 | A | 4/1999 | Cariapa et al. | |
| 5,897,512 | A | 4/1999 | Zagame | |
| 6,062,216 | A * | 5/2000 | Corn | A61B 5/113 128/204.23 |
| 6,349,724 | B1 | 2/2002 | Burton et al. | |
| 6,404,532 | B1 | 6/2002 | Berneth et al. | |
| 6,468,234 | B1 * | 10/2002 | Van der Loos | A61B 5/01 128/920 |
| 6,609,517 | B1 | 8/2003 | Estes et al. | |
| 6,846,294 | B2 | 1/2005 | Rastegar et al. | |
| 6,877,513 | B2 | 4/2005 | Scarberry et al. | |
| 7,182,082 | B2 | 2/2007 | Hofftichter | |
| 7,297,119 | B2 | 11/2007 | Westbrook et al. | |
| 7,762,263 | B2 | 7/2010 | Aarestad et al. | |
| 8,122,891 | B2 | 2/2012 | Kimani Mwangi | |
| 8,482,418 | B1 | 7/2013 | Harman | |
| 9,820,881 | B2 | 11/2017 | Aarestad et al. | |
| 10,092,442 | B2 | 10/2018 | Aarestad et al. | |
| 10,258,496 | B2 | 4/2019 | Aarestad et al. | |
| 2002/0002346 | A1 | 1/2002 | Horst | |
| 2002/0120207 | A1 | 8/2002 | Hoffman | |
| 2003/0083702 | A1 | 5/2003 | Standler et al. | |
| 2003/0153956 | A1 * | 8/2003 | Park | A61N 1/36585 607/17 |
| 2003/0167018 | A1 | 9/2003 | Wyckoff | |
| 2006/0266369 | A1 * | 11/2006 | Atkinson | A61F 5/56 128/848 |
| 2008/0114381 | A1 | 5/2008 | Voegele et al. | |
| 2008/0163875 | A1 * | 7/2008 | Aarestad | A61F 5/56 128/848 |
| 2008/0243017 | A1 | 10/2008 | Moussavi et al. | |
| 2009/0177124 | A1 | 7/2009 | Silwa et al. | |
| 2009/0234265 | A1 | 9/2009 | Reid, Jr. et al. | |
| 2009/0250071 | A1 | 10/2009 | Kimani Mwangi | |
| 2010/0016767 | A1 | 1/2010 | Jones et al. | |
| 2010/0101583 | A1 | 4/2010 | Chen et al. | |
| 2010/0106117 | A1 | 4/2010 | Lockwood et al. | |
| 2010/0163043 | A1 | 6/2010 | Hart et al. | |
| 2010/0174250 | A1 | 7/2010 | Hu et al. | |
| 2010/0275910 | A1 | 11/2010 | Aarestad et al. | |
| 2010/0277316 | A1 | 11/2010 | Schlangen et al. | |
| 2010/0294284 | A1 * | 11/2010 | Hohenhorst | A61F 5/012 128/848 |
| 2010/0298866 | A1 | 11/2010 | Fischvogt | |
| 2011/0066086 | A1 * | 3/2011 | Aarestad | A61F 5/56 601/11 |
| 2011/0066123 | A1 | 3/2011 | Tout et al. | |
| 2011/0132378 | A1 * | 6/2011 | Levendowski | A61B 5/11 128/848 |
| 2012/0123286 | A1 | 5/2012 | Wilson | |
| 2012/0330204 | A1 | 12/2012 | Baldauf et al. | |
| 2013/0046181 | A1 * | 2/2013 | Al-Abed | A61B 8/08 600/442 |
| 2013/0237793 | A1 * | 9/2013 | Farrugia | A61B 5/02405 600/383 |
| 2014/0144450 | A1 * | 5/2014 | Aarestad | A61F 5/56 128/845 |
| 2014/0276252 | A1 | 9/2014 | Hyde et al. | |
| 2014/0296751 | A1 | 10/2014 | Greenberg | |
| 2015/0126912 | A1 * | 5/2015 | Scarberry | A61F 5/56 601/6 |
| 2015/0142120 | A1 | 5/2015 | Papay | |
| 2016/0045356 | A1 | 2/2016 | Grossman et al. | |
| 2017/0367874 | A1 | 12/2017 | Aarestad et al. | |
| 2018/0028728 | A1 | 2/2018 | Aarestad et al. | |
| 2018/0125743 | A1 | 5/2018 | Aarestad et al. | |
| 2018/0177435 | A1 | 6/2018 | Aarestad et al. | |
| 2019/0021900 | A1 | 1/2019 | Aarestad | |
| 2019/0038453 | A1 | 2/2019 | Aarestad et al. | |
| 2019/0125572 | A1 | 5/2019 | Aarestad et al. | |
| 2019/0240065 | A1 | 8/2019 | Aarestad et al. | |

OTHER PUBLICATIONS

United States Patent and Trademark Office, "Final Office Action", "from U.S. Appl. No. 13/839,933", dated Sep. 8, 2016, pp. 1-22, Published in: US.

International Search Authority, "International Search Report for PCT/US2014/026122", "Foreign Counterpart to U.S. Appl. No. 13/839,933", dated Jul. 25, 2014, pp. 14, Published in: WO.

United States Patent and Trademark Office, "Office Action", "from U.S. Appl. No. 13/839,933", dated Jan. 20, 2016, pp. 1-27, Published in: US.

United States Patent and Trademark Office, "Final Office Action", "from U.S. Appl. No. 13/840,374", dated Oct. 26, 2016, pp. 1-20, Published in: US.

United States Patent and Trademark Office, "Office Action", "from U.S. Appl. No. 13/840,374", dated Jan. 20, 2016, pp. 1-20, Published in: US.

United States Patent and Trademark Office, "Restriction Requirement", "from U.S. Appl. No. 13/840,374", dated Jun. 12, 2015, pp. 1-8, Published in: US.

(56) References Cited

OTHER PUBLICATIONS

United States Patent and Trademark Office, "Advisory Action", "from U.S. Appl. No. 13/840,189", dated Nov. 16, 2015, pp. 1-4, Published in: US.

United States Patent and Trademark, "Advisory Action", "from U.S. Appl. No. 13/840,189", dated May 19, 2015, pp. 1-6, Published in: US.

United States Patent and Trademakr Office, "Final Office Action", "from U.S. Appl. No. 13/840,189", dated Jan. 30, 2015, pp. 1-31, Published in: US.

United States Patent and Trademark Office, "Final Office Action", "from U.S. Appl. No. 13/840,189", dated Jul. 14, 2016, pp. 1-27, Published in: US.

United States Patent and Trademark Office, "Notice of Allowance", "from U.S. Appl. No. 13/840,189", dated Feb. 13, 2017, pp. 1-9, Published in: US.

United States Patent and Trademark Office, "Office Action", "from U.S. Appl. No. 13/840,189", dated Sep. 25, 2014, pp. 1-30, Published in: US.

United States Patent and Trademark Office, "Office Action", "from U.S. Appl. No. 13/840,189", dated Dec. 31, 2015, pp. 1-20, Published in: US.

United States Patent and Trademark Office, "Office Action", "from U.S. Appl. No. 13/840,189", dated Jan. 13, 2017, pp. 1-30, Published in: US.

United States Patent and Trademark Office, "Advisory Action", "from U.S. Appl. No. 13/839,605", dated Mar. 18, 2016, pp. 1-3, Published in: US.

United States Patent and Trademark Office, "Final Office Action", "from U.S. Appl. No. 13/839,605", dated May 6, 2016, pp. 1-23, Published in: US.

United States Patent and Trademark Office, "Office Action", "from U.S. Appl. No. 13/839,605", dated Nov. 10, 2015, pp. 1-21, Published in: US.

United States Patent and Trademark Office, "Office Action", "from U.S. Appl. No. 13/839,605", dated Nov. 3, 2016, pp. 1-9, Published in: US.

United States Patent and Trademark Office, "Office Action", "from U.S. Appl. No. 13/839,605", dated Nov. 14, 2016, pp. 1-12, Published in: US.

U.S. Patent and Trademark Office, "Office Action", U.S. Appl. No. 13/840,374, dated Jul. 9, 2020, pp. 1-38, Published: US.

\* cited by examiner

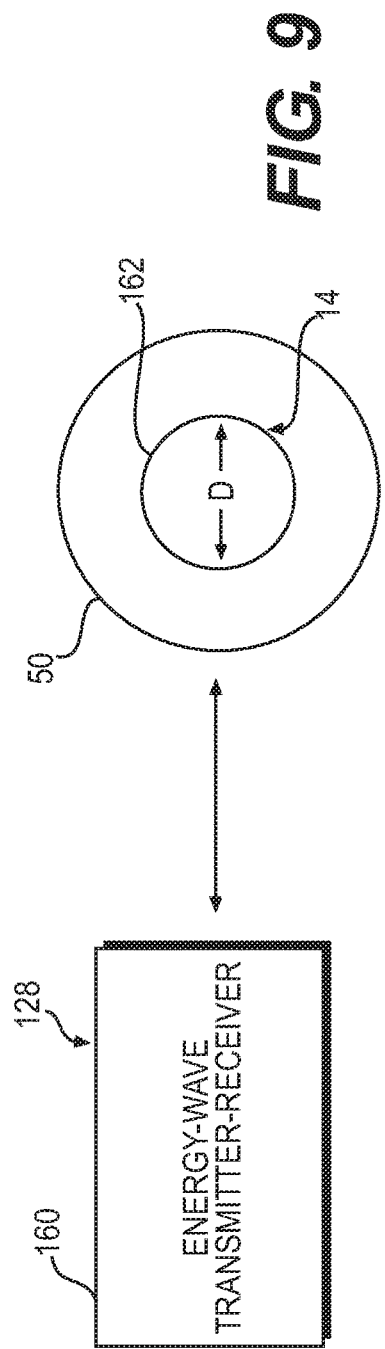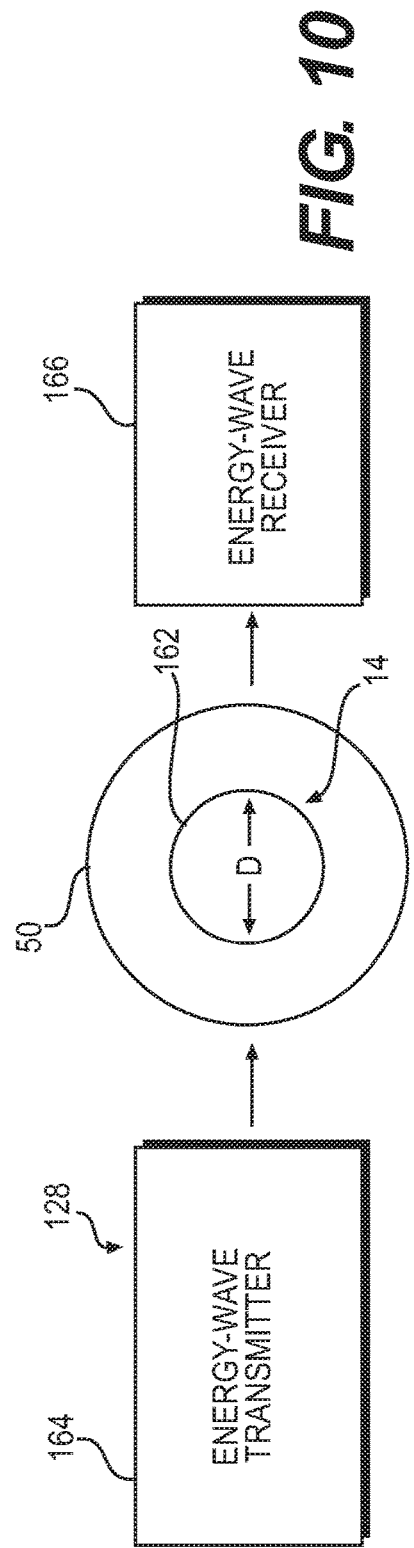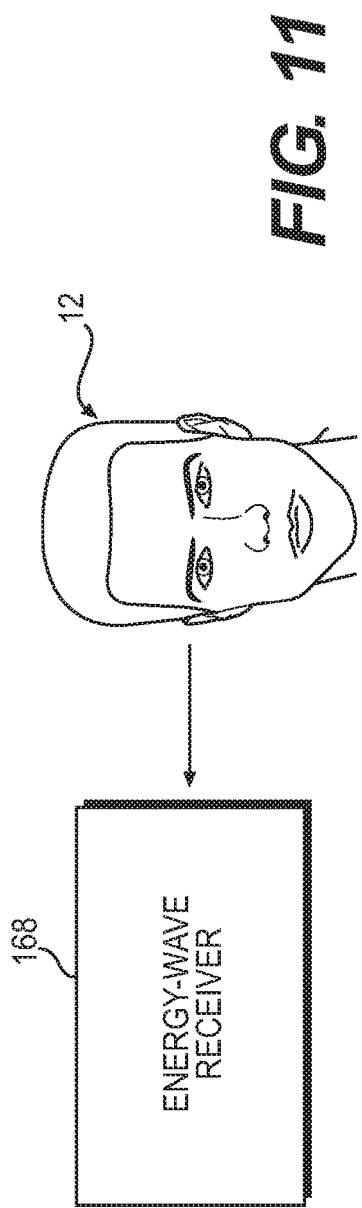

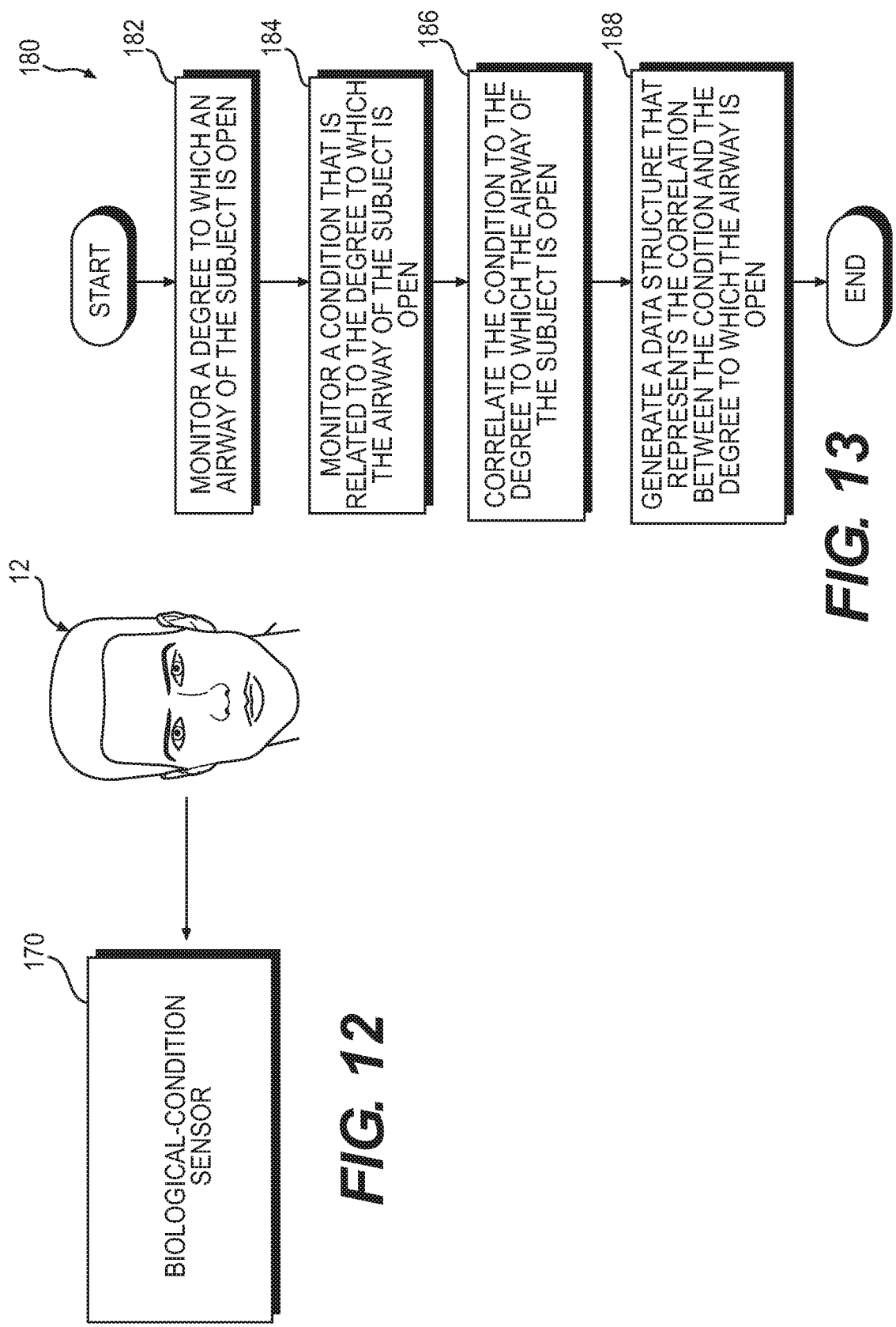

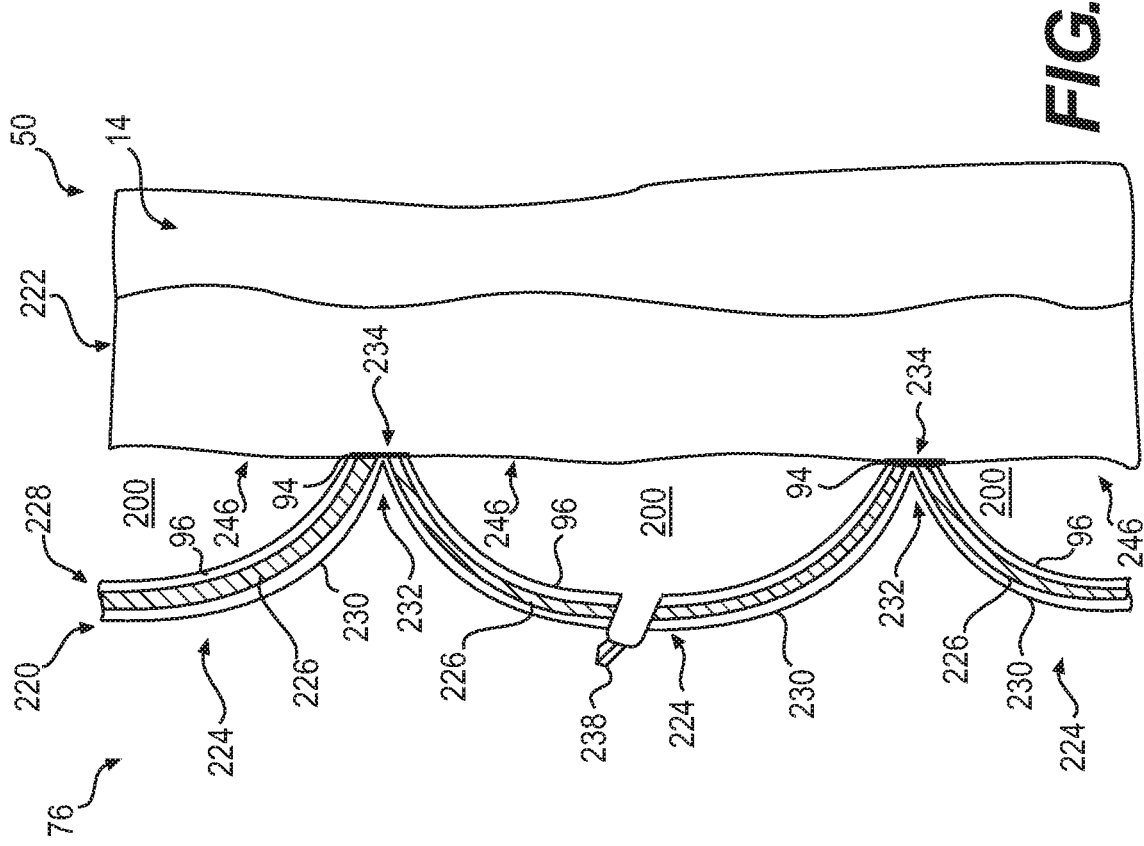
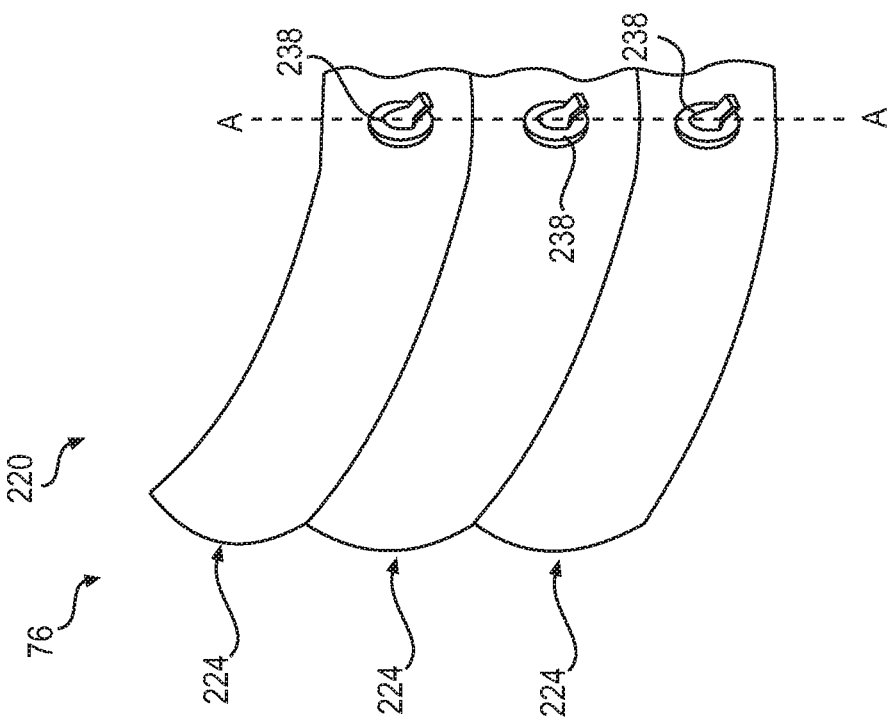

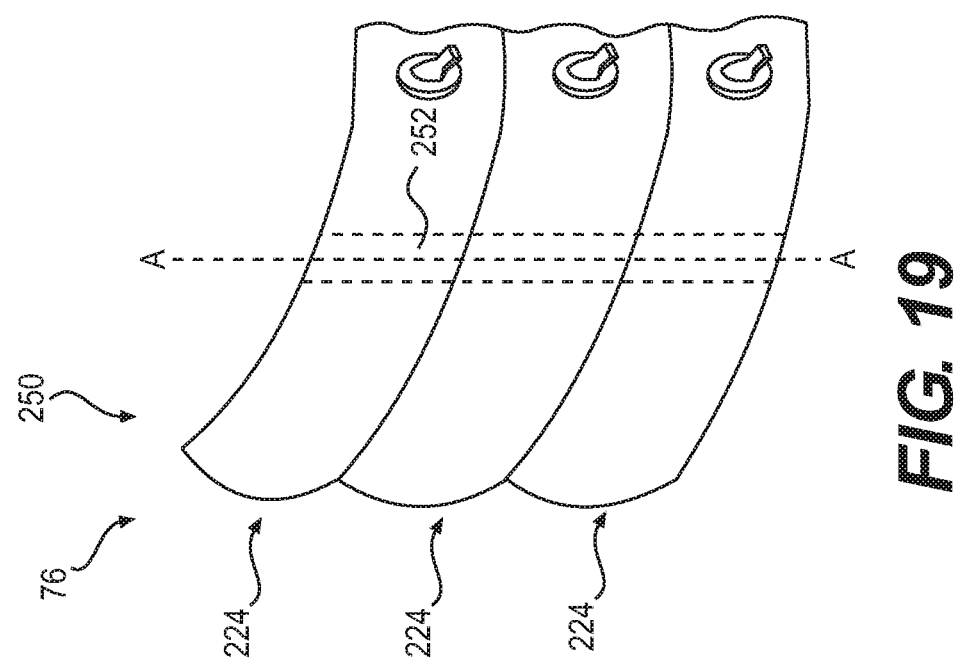

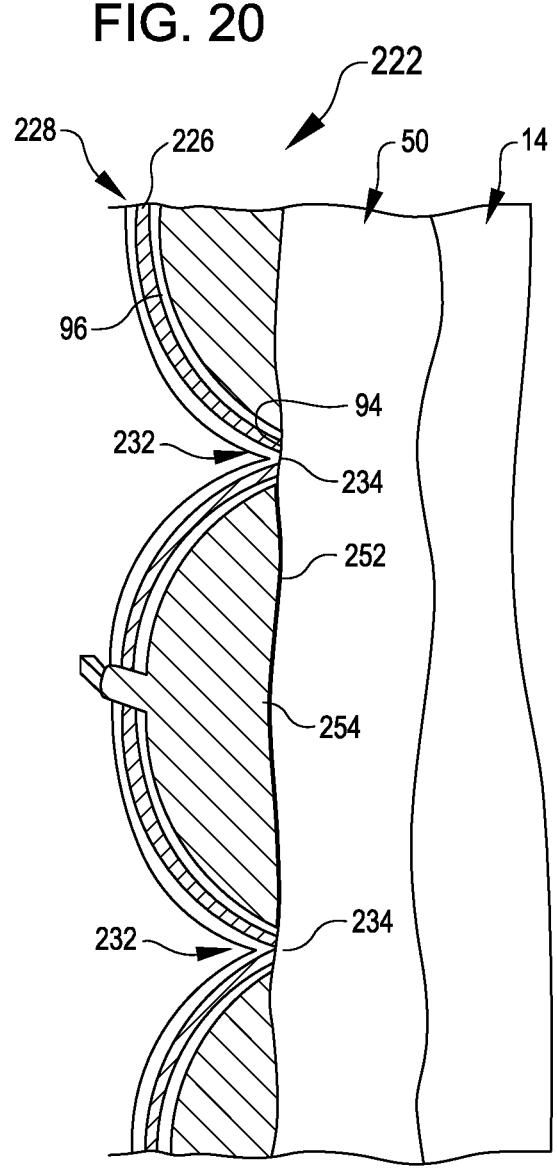

TREATING SLEEP APNEA WITH NEGATIVE PRESSURE

PRIORITY APPLICATIONS

The present application is a continuation-in-part of U.S. patent application Ser. No. 13/839,605, titled TREATING SLEEP APNEA WITH NEGATIVE PRESSURE, naming Roderick A. Hyde, Kenneth G. Caldeira, Lowell L. Wood Jr., Dennis J. Rivet, Michael A. Smith as inventors, filed 15 Mar. 2013, the contents of which are incorporated by reference.

The present application is a continuation-in-part of U.S. patent application Ser. No. 13/839,933, titled CORRELATING A CONDITION OF A SUBJECT WITH A DEGREE OF SLEEP APNEA BEING EXPERIENCED BY THE SUBJECT, naming Roderick A. Hyde, Kenneth G. Caldeira, Lowell L. Wood Jr., Dennis J. Rivet, Michael A. Smith as inventors, filed 15 Mar. 2013, the contents of which are hereby incorporated by reference.

The present application is a continuation-in-part of U.S. patent application Ser. No. 13/840,189, titled SLEEP-APNEA-TREATMENT SYSTEM THAT CHANGES THE TREATMENT PRESSURE OVER A PERIOD THAT BEGINS OR ENDS AT A SETTABLE TIME, naming Roderick A. Hyde, Kenneth G. Caldeira, Lowell L. Wood Jr., Dennis J. Rivet, Michael A. Smith as inventors, filed 15 Mar. 2013, the contents of which are hereby incorporated by reference.

The present application is a continuation-in-part of U.S. patent application Ser. No. 13/840,374, titled SLEEP-APNEA-TREATMENT SYSTEM WITH MULTIPLE PRESSURE AND SEALING SURFACES, naming Roderick A. Hyde, Kenneth G. Caldeira, Lowell L. Wood Jr., Dennis J. Rivet, Michael A. Smith as inventors, filed 15 Mar. 2013, the contents of which are hereby incorporated by reference.

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

RELATED APPLICATIONS

U.S. patent application Ser. No. 15/406,372, titled OBTAINING, WITH A SLEEP-APNEA DEVICE, INFORMATION RELATED TO SLEEP-APNEA EVENTS AND SLEEP-APNEA TREATMENT, AND CORRELATING SLEEP-APNEA EVENTS AND SLEEP-APNEA TREATMENT WITH SUBJECT LIFESTYLE AND WELLBEING, naming Roderick A. Hyde, Kenneth G. Caldeira, Gary L. McKnight, Lowell L. Wood Jr., Dennis J. Rivet, Katherine Sharadin, Michael A. Smith as inventors, filed Jan. 13, 2017, is related to the present application and its contents are hereby incorporated by reference.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

A system for treating sleep apnea includes a collar, a pump, a motor, a sensor, and a controller. The collar is configured to maintain an airway of a subject open while the subject is sleeping by applying, to a throat of the subject, a negative pressure having a magnitude, and the pump is configured to generate the negative pressure. The motor is configured to drive the pump, and the sensor is configured to generate a sense signal that is related to a degree to which the airway is open or obstructed. And the controller is configured to vary the magnitude of the negative pressure in response to the sense signal.

For example, one or more of the pump, motor, sensor, and controller can be secured to the collar such that the system is self-contained, i.e., the entire system can be worn by the subject, e.g., held over the subject's throat by strap assembly. Alternatively, the system can include a base unit that includes at least the pump and the motor, and can include an air hose that couples the base unit to the collar such that the pump can generate the negative pressure via the hose.

BRIEF DESCRIPTION OF THE FIGURES

FIG. 9 is a diagram of a portion of the apnea-degree-sensor assembly of FIG. 8, and of a cross section of a neck and an airway of a subject, according to an embodiment.

FIG. 10 is a diagram of a portion of the apnea-degree-sensor assembly of FIG. 8, and of a cross section of neck and an airway of a subject, according to another embodiment.

FIG. 11 is a diagram of a portion of the apnea-degree-sensor assembly of FIG. 8, and of a cross section of a neck and an airway of a subject, according to yet another embodiment.

FIG. 12 is a diagram of a portion of the apnea-degree-sensor assembly of FIG. 8, and of a subject, according to still another embodiment.

FIG. 13 is a flow diagram of a procedure for correlating a degree to which an airway of a subject is open to a condition that is related to the degree to which the airway is open, according to an embodiment.

FIG. 16 is a diagram of a portion of a collar of FIGS. 4-7, according to an embodiment.

FIG. 17 is a view of the collar portion of FIG. 16 taken along line A-A of FIG. 16, according to an embodiment.

FIG. 19 is a diagram of a portion of a collar of FIGS. 4-7, according to another embodiment.

FIG. 20 is a view of the collar portion of FIG. 19 taken along line A-A of FIG. 19, according to an embodiment.

DETAILED DESCRIPTION

Figure 1:
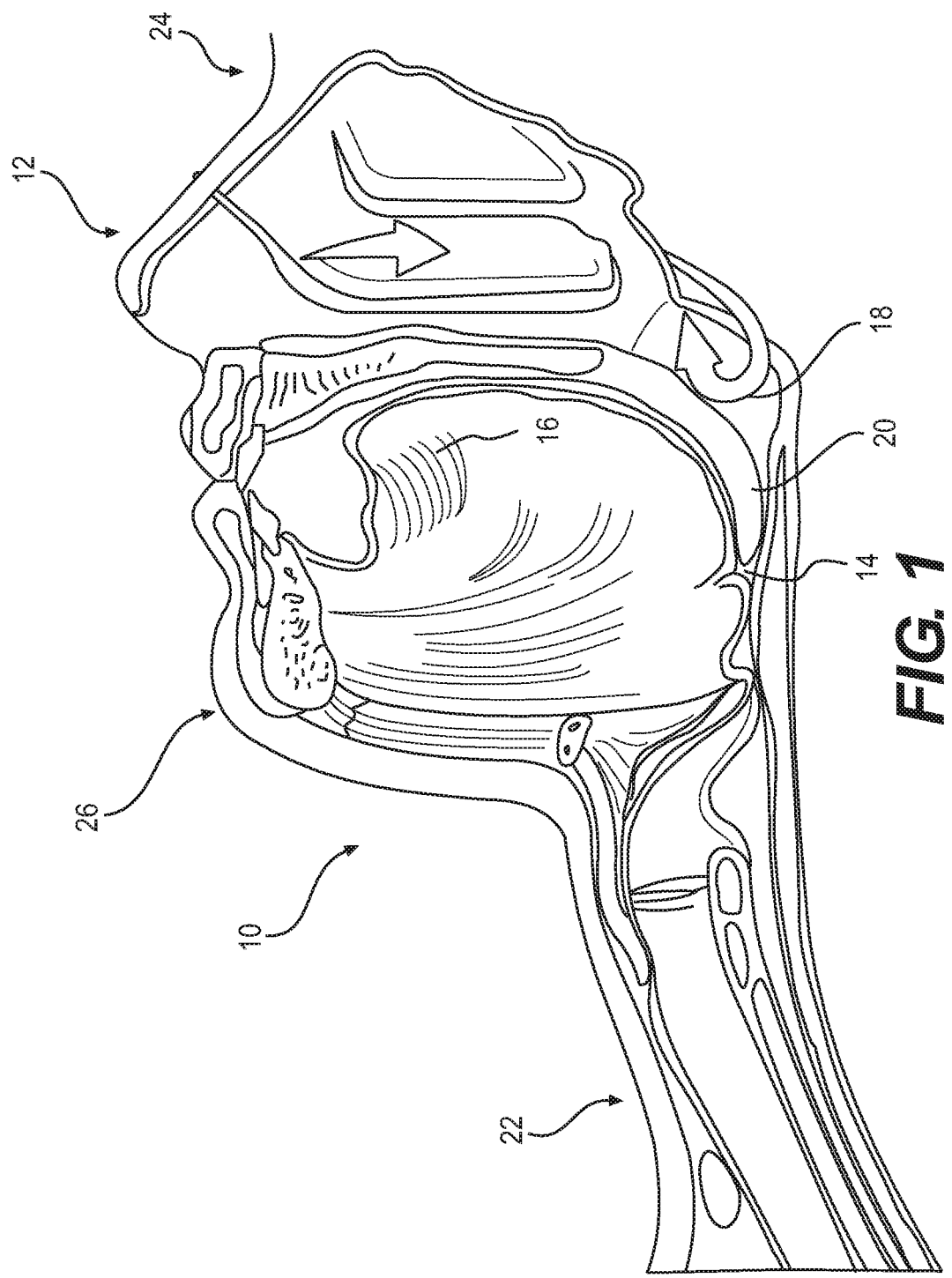
FIG. 1 is a diagram of an airway of a human subject, and of other biological tissues and structures near the airway.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

One or more embodiments are described with reference to the drawings, wherein like reference numerals may be used to refer to like elements throughout. In the following description, for purposes of explanation, numerous specific details are set forth in order to provide a thorough understanding of the one or more embodiments. It may be evident, however, that one or more embodiments may be practiced without these specific details. In other instances, well-known structures and devices are shown in block-diagram form in order to facilitate describing one or more embodiments.

Sleep apnea is a disorder characterized by instances of abnormally low breathing, or by instances of abnormal pauses in breathing (e.g., "apneas," or "apnea events"), during sleep; for example, such apneas can occur with a frequency of approximately 5-30 times or more per hour, and each apnea can last from approximately ten seconds to one or more minutes.

To prevent a subject who suffers from sleep apnea from suffocating during an apnea, the body produces a short "burst" of adrenaline, which burst typically rouses the subject enough to start him/her breathing again, but not enough to fully awaken him/her.

Unfortunately, these bursts of adrenaline can cause the subject to experience significant health problems. For example, because such bursts of adrenaline can stress the subject's heart by causing the subject's heart rate to increase relatively quickly, such bursts may increase the subject's risk of heart attack or stroke. Furthermore, because these bursts of adrenaline interrupt the subject's deep-sleep patterns, these bursts can be the underlying cause of health problems that are associated with a lack of sleep; examples of such lack-of-sleep-related health problems include an increase in non-lean (adipose tissue) body mass, arteriosclerosis, daytime fatigue, reduced cognitive function, reduced reaction time, and reduced attention span.

Because a subject suffering from sleep apnea is rarely aware of having difficulty breathing during sleep, or even after awakening, the subject may be unaware for many years that he/she suffers from sleep apnea until one or more symptoms, for example, in the form of one or more of the above-described health problems, manifest themselves to a degree that causes the subject to seek medical attention. But by then, the subject may have suffered serious injury (e.g., a heart attack), disability (brought on, e.g., by stroke), or even death (brought on, e.g., by the subject's failure to begin breathing after an apnea).

Consequently, proper treatment of sleep apnea can improve a subject's health in both the short term and in the long term, and, in some cases, can even prevent the subject's premature death.

The most common type of sleep apnea is obstructive sleep apnea.

FIG. 1 is a cut-away view of a head-and-neck region 10 of a subject 12.

Referring to FIG. 1, obstructive sleep apnea is characterized by an airway 14 of the subject 12 collapsing, i.e., becoming blocked during sleep by, e.g., the back of the tongue 16, the soft palate 18, or the uvula 20; therefore, each instance of a blocked airway typically causes an "apnea" as described above. Causes of a blocked airway 14 during sleep can include poor muscle tone in, over relaxation of, or excess tissue in, the tongue 16, soft palate 18, or uvula 20.

When the body of the subject 12 produces a burst of adrenaline during a blocked-airway-induced apnea to start the subject breathing again as described above, the adrenaline burst may unblock the airway 14 by causing the subject to, e.g., cough, move his/her neck 22, head 24, or jaw 26, or to breathe more deeply (the stronger suction caused by a deeper breath may force open the airway).

Then, after the subject 12 falls back into a deeper sleep, the muscles of the neck 22 and jaw 26 relax, the subject's respiratory rate returns to a deeper-sleep level, and, therefore, another cycle of an apnea followed by an adrenaline burst may commence.

Still referring to FIG. 1, there are many treatments available for obstructive sleep apnea.

Examples of invasive treatments include surgery to remove tissue from the body part (e.g., the tongue 16, soft palate 18, or uvula 20) responsible for the blockage of the airway 14, and surgery to implant one or more members into the blocking body part (e.g., to implant plastic rods into the soft palate) to "stiffen" the body part.

Unfortunately, potential problems with such invasive treatments include the risks, recovery time, irreversibility, and pain associated with a surgical procedure, including the risk that the procedure will cause the subject post-recovery discomfort when he/she swallows or while he/she is eating, and the risk that the procedure will ultimately prove unsuccessful in preventing reoccurrence of the airway blockages that cause obstructive sleep apnea.

And examples of non-invasive treatments include the subject 12 losing weight, using an oral appliance that maintains the subject's jaw 26 in a slightly protruding position during sleep, and using a Continuous Positive Airway Pressure (CPAP) machine, which is described below in conjunction with FIG. 2.

Although such non-invasive treatments are generally preferred over invasive treatments because, e.g., they can have fewer risks and side effects than invasive treatments, some non-invasive treatments, such as losing weight and using an oral appliance, may be difficult to obtain, or ineffective, for some subjects who suffer from obstructive sleep apnea.

But fortunately, it has been found that a CPAP machine can successfully treat obstructive sleep apnea in the majority of subjects who would otherwise suffer from it.

Figure 2:
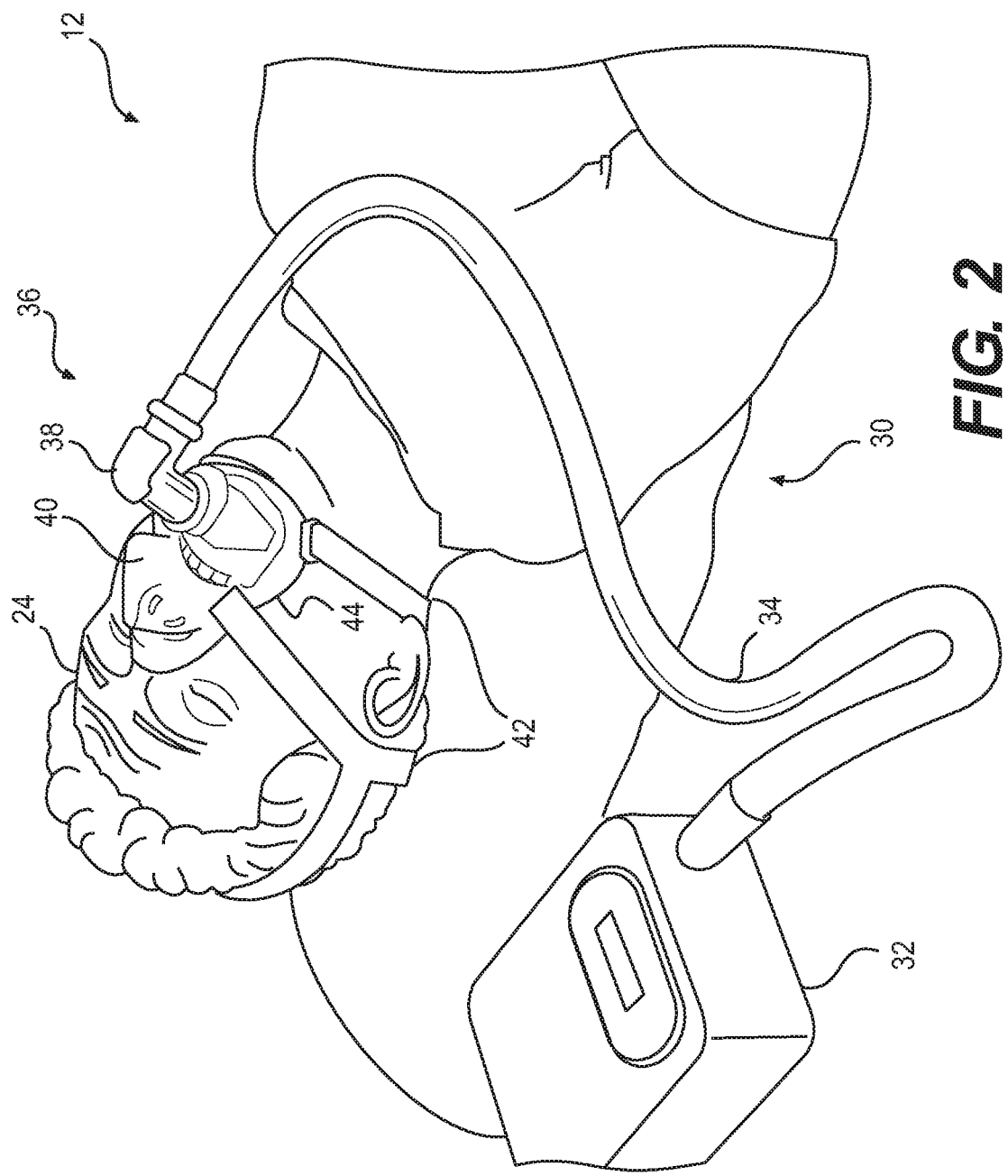
FIG. 2 is a diagram of a subject using a CPAP machine.

FIG. 2 is a view of a sleeping subject 12 using a CPAP machine 30 to prevent the occurrence of obstructive sleep apnea.

The CPAP machine 30 includes a base unit 32, a hose 34, and a mask assembly 36.

The base unit 32 is configured to maintain the air pressure within the hose 34, and thus within the airway 14 (FIG. 1) of the subject 12, at approximately constant levels while the subject is breathing in (inspiration) and while the subject is breathing out (expiration). If the CPAP machine 30 maintains the airway pressure at a different approximately constant level during inspiration than it does during expiration, then it is more properly called a BiPAP machine, although in common usage, "CPAP" is used to denote both a machine that maintains the airway pressure at the same positive level during inspiration and expiration and a machine that maintains the airway pressure at different positive levels during inspiration and expiration. The base unit 32 typically includes a power cord that plugs directly into a household power outlet (e.g., 110/220 VAC), or is coupleable to an AC adapter.

The hose 34 is configured to couple the base unit 32 to the mask assembly 36, and is typically long enough (e.g., six to ten feet) to allow the subject 12 to place the base unit on a floor or on a night stand while the subject is using the CPAP machine 30.

The mask assembly 36 includes a fitting 38, a mask 40, and straps 42. The fitting 38 is configured to couple the mask 40 to the hose 34, and may be coupled to the mask with a swivel joint that allows the subject 12 some freedom of movement. The mask 40 is configured to form an airtight seal 44 around at least the nose of the subject 12 (although the mask may also form a seal around the subject's mouth as shown in FIG. 2), and includes one or more openings (not shown in FIG. 2) that allow air to flow constantly from the base unit 32, through the hose 34 and fitting 38, into the mask 40, and out through the one or more openings, even during inspiration; without this constant airflow, the air inspired by the subject may become "stale." And the straps 42 secure the mask 40 to the head 24 of the subject 12 with a degree of tightness sufficient to form the airtight seal 44 between the mask and the face of the subject.

Still referring to FIG. 2, although, as described above, the CPAP machine 30 is an effective non-invasive treatment for obstructive sleep apnea, the CPAP machine may still have some shortcomings. For example, the nature of the hose 34 effectively tethering the mask assembly 36 to the base unit 32 may rob the subject 12 of his/her full range of movement during sleep. As an example, the subject 12 may be unable to roll to his/her left without causing the hose 34 to pull the base unit 32 off of a nightstand; or, if the base unit is on the floor, then the subject rolling to his/her left may cause the hose 34 to become taught and, therefore, to dislodge the mask 40 from the subject's face and break the seal 44. Furthermore, the subject 12 may be unable to sleep on his/her side without the pillow dislodging the mask 40 from the subject's face and breaking the seal 44. Moreover, the force with which the straps 42 must hold the mask 40 against the face of the subject 12 to form an airtight seal may cause discomfort to the subject. In addition, the CPAP machine 30 may prove inconvenient for travel, because, for example, when carrying the machine aboard an airplane, the subject 12 must separate at least the base unit 32 from other items while going through security, and the dimensions of the base unit may make it difficult for carrying in a briefcase or overnight bag.

Figure 3:
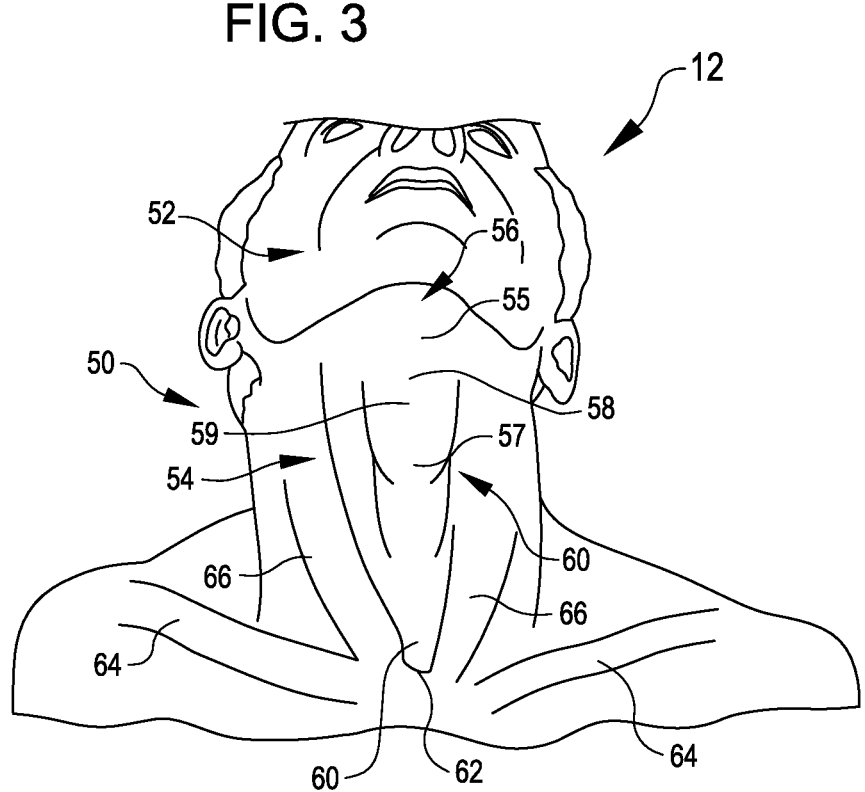
FIG. 3 is a diagram of a neck of a subject, and of a throat region of the neck.

FIG. 3 is a diagram of a neck 50 and a jaw 52 of a subject 12, and of a throat 54 of the neck.

Referring to FIG. 3, applying a negative pressure (i.e., suction or a vacuum) to one or more regions of the neck 50 and/or the jaw 52 of the subject 12 can treat obstructive sleep apnea non-invasively. For example applying a negative pressure to an underside 56 of the jaw 52, or to a region 58, such as the mylohyoideus, of the throat 54 beneath the jaw, while the subject 12 is sleeping can assist to position the subject's jaw, tongue 16 (FIG. 1), or one or more other biological structures of the subject so as to open, and to maintain open, the subject's airway 14 (FIG. 1). In another example, applying a negative pressure to one or more portions of a throat region 60 (which is below the throat region 58, above the sternal head 62 and clavicle 64, and between the sternocleidomastoid muscles 66) while the subject 12 is sleeping can also position one or more biological structures of the subject 12 so as to open, and to maintain open, the subject's airway 14. In yet another example, applying a negative pressure to a region of the throat 54 between the anterior belly of Digastricus 55, the thyroid cartilage (i.e., Adam's apple) 57, and the sternocleidomastoid muscles 66 while the subject 12 is sleeping can also position one or more biological structures of the subject 12 so as to open, and to maintain open, the subject's airway 14. In still another example, applying a negative pressure to a region of the throat 54 between the anterior belly of Digastricus 55, the hyoid bone 59, and the sternocleidomastoid muscles 66 while the subject 12 is sleeping can also position one or more biological structures of the subject 12 so as to open, and to maintain open, the subject's airway 14.

Figure 4:
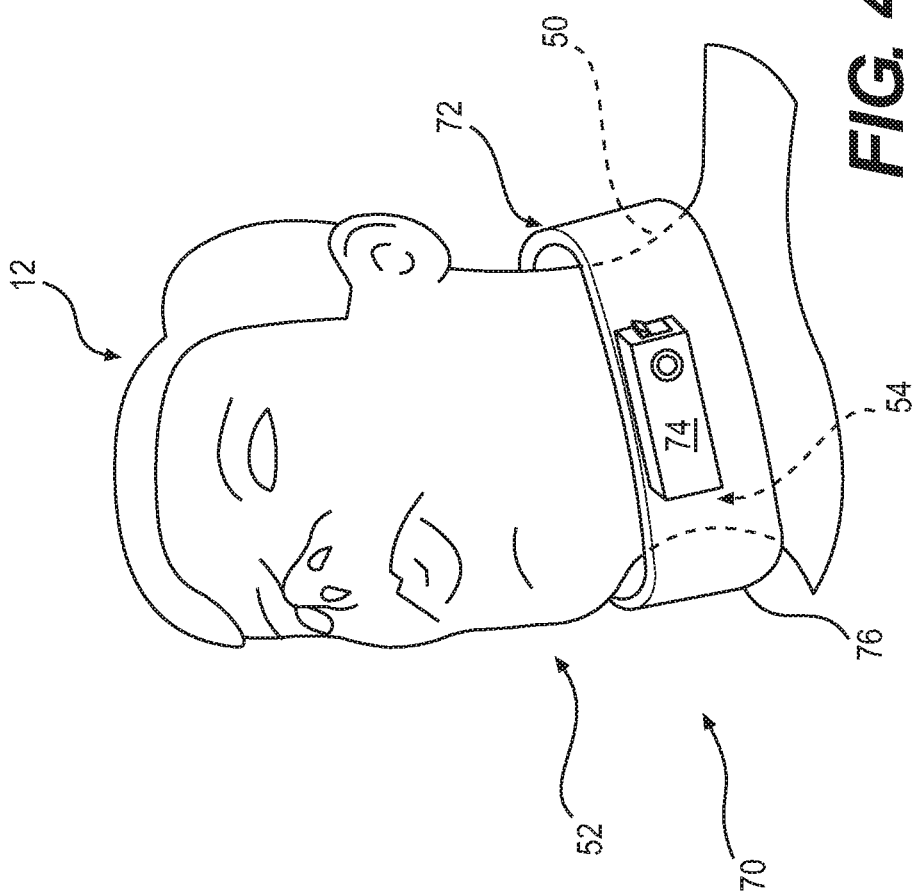
FIG. 4 is a view of a subject wearing a system for treating sleep apnea, according to an embodiment.

FIG. 4 is a diagram of a subject 12 using a negative-pressure sleep-apnea-treatment system 70, which is configured to treat obstructive sleep apnea, according to an embodiment. As described below in conjunction with FIGS. 5-22, the system 70 is self-contained, and is configured to open, and to maintain open, the subject's airway 14 (FIG. 1) during sleep by applying and maintaining a negative pressure to one or more regions of the subject's neck 50, jaw 52, or throat 54. As used above and hereinafter, "self-contained" means that the system 70 is configured to treat obstructive sleep apnea by itself. As compared to a CPAP machine such as the CPAP machine 30 of FIG. 2, the system 70 can allow the subject 12 more freedom of movement because it is not tethered to any other item or location, can be more comfortable because it is worn around the neck and not over the face, and can be more suitable for travel because it can have fewer pieces, can be smaller, and can be foldable.

The negative-pressure sleep-apnea-treatment system 70 includes a collar assembly 72 and a component module 74, which is configured to be secured to the collar.

The collar assembly 72 includes a collar 76 and fasteners (not visible in FIG. 4), such as straps, snaps, buttons, or Velcro® strips, that are configured to secure the collar to the subject's neck 50 such that the collar forms an airtight seal around the one or more regions of the subject's neck, jaw 52, or throat 54 to which the system 70 is configured to apply a negative pressure. The collar 76 may be partially or fully flexible, may be formed from one or more suitable materials such as cloth, foam, metal, or plastic, and the collar or the fasteners may be configured to allow adjustment of the interior dimensions of the collar assembly 72 such that the assembly can fit subjects having a variety of neck circumferences, lengths, and shapes. The collar assembly 72 is further described below in conjunction with FIGS. 5-7.

And the module 74 is configured to include one or more components of the system 70 other than the collar assembly 72. For example, the module 74 can include an air pump, motor, power supply, pressure, airway, and other sensors, and a controller circuit such as a microprocessor or microcontroller. The module 74 is further described below in conjunction with FIG. 8.

Still referring to FIG. 4, alternate embodiments of the negative-pressure sleep-apnea-treatment system 70 are contemplated. For example, instead of being flexible, the collar 76 may include two or more rigid portions that are hinged together such that these portions are configured to open and receive the subject's neck 50, and then to close and attach around the neck. Furthermore, not all of the system components other than the collar assembly 72 may be disposed within the module 74. For example, some or all of these other components can be secured to the outside of the collar 76 or the outsides of the fasteners, can be secured to the inside of the collar or the insides of the fasteners, or can be disposed inside of the collar 76 or fasteners. Moreover, the module 74 and collar 76 may have any suitable shapes other than those shown in FIG. 4.

Figure 5:
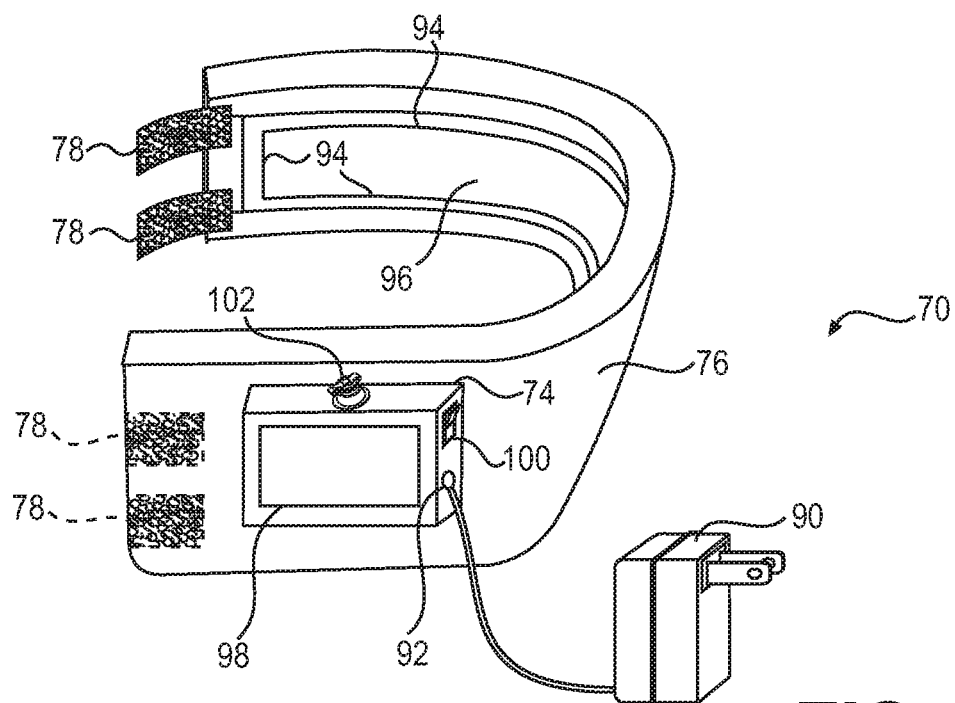
FIG. 5 is a view of a system for treating sleep apnea, according to an embodiment.

FIG. 5 is a view of the negative-pressure sleep-apnea-treatment system 70 of FIG. 4, according to an embodiment.

The collar 76 is a single, flexible piece that is configured to fully surround the subject's neck 50 (FIG. 4) while the subject wears the system 70, and the Velcro® fasteners 78 are adjustable so that the system 70 can fit a variety of neck sizes and shapes.

The system 70 also includes an AC adapter/charger 90, which is configured to couple to a receptacle 92 of the component module 74, and to power the system while the system is operating or to charge a battery (not shown in FIG. 5) of the system while the system is or is not operating. Alternatively, the receptacle 92 may be configured for coupling to a power cord that is configured for coupling to a standard power outlet (e.g., 110 VAC 220 VAC).

Furthermore, the system 70 includes one or more sealing surfaces 94, which are configured to form respective airtight seals with respective opposing regions of the subject's neck 50, and includes one or more vacuum surfaces 96, which are bounded by the sealing surfaces 94 and which are configured to sit opposite the regions of the subject's neck 50 (FIG. 4), jaw 52 (FIG. 4), or throat 54 (FIG. 4) to which the system applies a negative pressure. The one or more sealing surfaces 94 and the one or more vacuum surfaces 96 are further described below in conjunction with FIGS. 14-21.

Moreover, the component module 74 includes an input-output device 98, a power-switch assembly 100, and an air-outlet assembly 102. The input-output device 98 is, for example, a touch screen that allows the subject 12 (FIG. 4) to program, or otherwise to control, the system 70, and to receive information, such as status information and confirmation of programming, from the system 70. For example, the input-output device can be configured to allow the subject 12 to set the magnitude of the negative pressure, or of a maximum threshold thereof, and to allow the subject to set a wake-up time in anticipation of which the system 70 can adjust settings (e.g., the magnitude of the negative pressure) to gently awaken the subject. Alternatively, the input-output device 98 may include separate input (e.g., a keypad) and output (e.g., a display, a touchscreen display) devices. The power-switch assembly 100 is, for example, any suitable assembly (e.g., a toggle switch or a tactile slide switch displayed by a touchscreen) that allows the subject 12 (FIG. 4) to turn the system 70 "on" or "off." And the air-outlet assembly 102 provides an outlet for the air that the system 70 sucks from between the collar 76 and the subject's neck 50 (FIG. 4), jaw 52 (FIG. 4), or throat 54 (FIG. 4) to create one or more regions of negative pressure between the collar and the neck, jaw, or throat.

Figure 6:
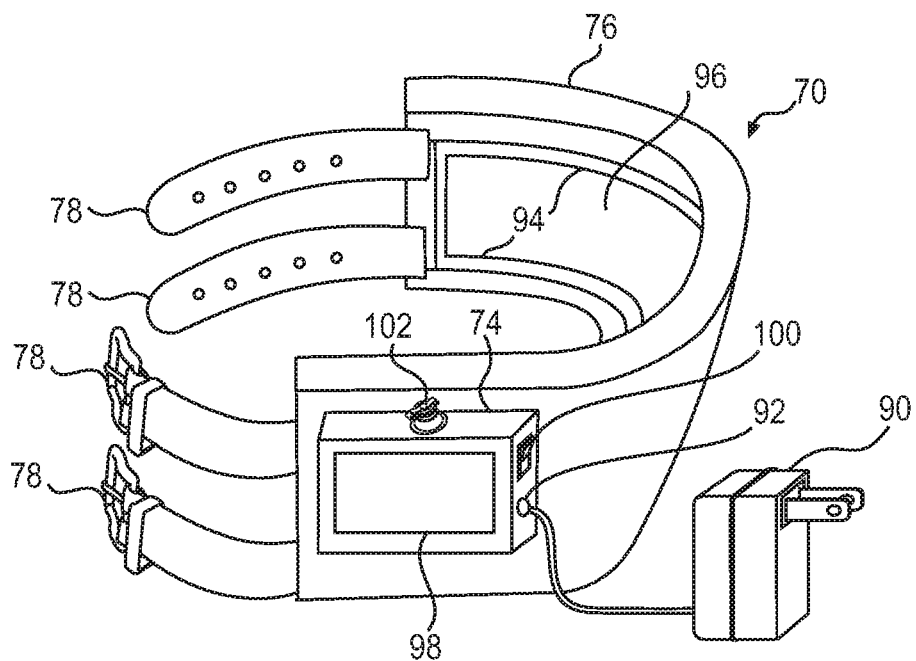
FIG. 6 is a view of a system for treating sleep apnea, according to another embodiment.

FIG. 6 is a view of the negative-pressure sleep-apnea-treatment system 70 of FIG. 4, according to yet another embodiment. The system 70 of FIG. 6 is similar to the system 70 of FIG. 5, except that the collar 76 is configured to surround the subject's neck 50 (FIG. 4) only partially when he/she wears the system, and the adjustable Velcro® fasteners 78 of FIG. 6 are longer than the fasteners 78 of FIG. 5 to compensate for the reduced length of the collar.

Figure 7:
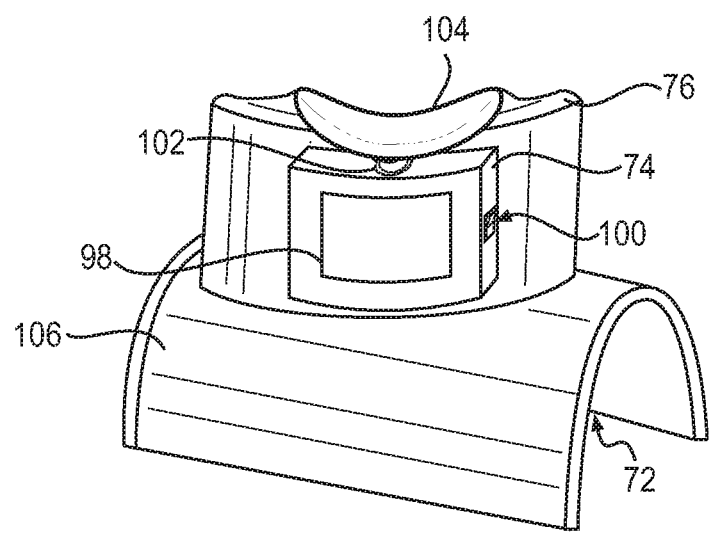
FIG. 7 is a view of a system for treating sleep apnea, according to yet another embodiment.

FIG. 7 is a view of the negative-pressure sleep-apnea-treatment system 70 of FIG. 4, according to still another embodiment. The system 70 of FIG. 7 is similar to the systems 70 of FIGS. 5-6, except that the collar 76 includes a portion 104, which is configured for positioning under the jaw 52 (FIG. 4) of the subject 12 (FIG. 4), and the system also includes a collar support 106. The collar 76 is configured to surround the neck 50 (FIG. 4) of the subject 12 (FIG. 4) only partially, and includes the portion 104, which is configured to allow for the application of negative pressure beneath the subject's jaw 52 (FIG. 4) or chin 26 (FIG. 1). And the collar support 106, which can take the place of, or be in addition to, the fasteners 78 of FIGS. 5 and 6, is configured to fit over the shoulders (not shown in FIG. 7) of the subject 12. The support 106 can be made of any suitable material that is flexible, rigid, or semi-rigid, and can have a design that affords the subject 12 freedom of movement while sleeping. And although not shown in FIG. 7, the system 70 of FIG. 7 may include one or more of the AC adapter 90, adapter receptacle 92, sealing surfaces 94, and vacuum surface 96, or any suitable alternatives thereof.

Referring to FIGS. 4-7, alternate embodiments of the sleep-apnea-treatment system 70 are contemplated. For example, the position of the component module 74 relative to the collar assembly 72 can be different than described. Furthermore, the positions of the input-output device 98, power switch 100, and air outlet 102 relative to the component module 74 may be different than described. Moreover, the collars 76 of FIGS. 4-6 may have chin or jaw portions that perform the same function as the portion 104 of FIG. 7. In addition, the system 70 may be modified any suitable manner.

Figure 8:
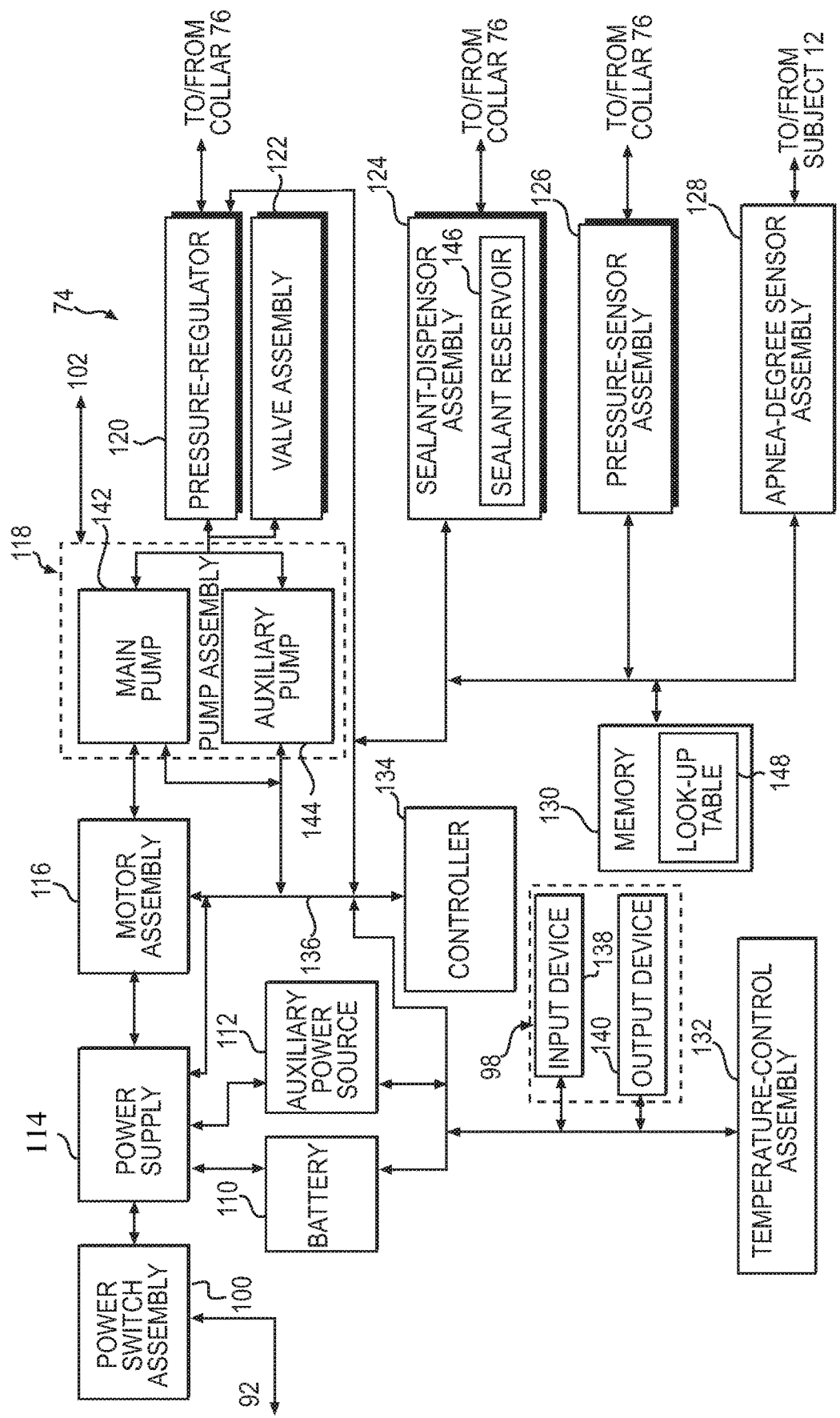
FIG. 8 is a block diagram of a component module of the sleep-apnea systems of FIGS. 4-7, according to an embodiment.

FIG. 8 is a block diagram of the component module 74 of FIGS. 4-7, according to an embodiment. In addition to the power receptacle 92, the input-output device 98, the power-switch assembly 100, and the air-outlet assembly 102, the component module 74 includes the following components: a power source such as a battery 110, an auxiliary power source 112, a power supply 114, a motor assembly 116, a pump assembly 118, a pressure-regulator assembly 120, a valve assembly 122, a sealant-dispenser assembly 124, a pressure-sensor assembly 126, an apnea-degree-sensor assembly 128, a memory 130, a temperature-control assembly 132, a controller 134, and a bus 136. The module 74 may also include a package (not shown in FIG. 8) that houses these components. For example, the package may be formed from an epoxy resin and may be sealed to protect, or to prevent access to, the housed components, or may include a structure that allows access to one or more of the housed components for, e.g., repair or replacement. Furthermore, in addition to the power receptacle 92, the component module 74 may include other suitable receptacles or connectors that allow, e.g., airflow between the pressure-regulator assembly 120, the valve assembly 122, and the collar 76 (FIGS. 4-7), sealant flow between the dispenser assembly 124 and the collar, and signal communication to or from the sensor assemblies 126 and 128.

The power receptacle 92 is configured to receive a DC power signal, via the power-switch assembly 100, from, e.g., the AC adapter 90 (FIGS. 5-6), or is configured to receive an AC power signal from, e.g., a standard power outlet (e.g., 110 VAC, 220 VAC).

The input-output device 98 is configured to receive data from, e.g., the subject 12 (FIG. 4), a sleep technician, or a sleep doctor, and to provide data to the subject, the technician, or the doctor. For example, the device 98 can be a touch screen that allows one to input data, and that displays data. Alternately, the device 98 may include a separate input device 138, such as a keypad or card reader, and a separate output device 140, such as a display screen or card writer. Examples of data that one may input to the component module 74 via the device 98 include program instructions for the controller 134, and system-configuration and system-operating parameters such as pressure and temperature ranges and threshold levels.

The battery 110 is configured to store energy for powering the components of the component module 74, and for powering the negative-pressure sleep-apnea-treatment system 70 (FIGS. 4-7) in general. The battery 110 can be any suitable type of battery, such as a nickel-cadmium battery, a lithium-ion battery, or an alkaline battery, can produce any suitable output voltage (e.g., in a range of 5-25 VDC), and can be one-time usable or rechargeable. Furthermore, the battery 110 can include more than one battery or battery cell coupled together in electrical series, electrical parallel, or both electrical series and electrical parallel. Moreover, the battery 110 can provide an alarm (e.g., an alarm signal) to, e.g., the controller 134 or the input-output device 98, when the magnitude of the charge or voltage that the battery stores reduce to or below a low-charge threshold; alternatively, another component, e.g., the controller 134, can monitor the battery charge or voltage and generate such an alarm. In addition, the component module 74 may include a receptacle to hold the battery 110.

The auxiliary power source 112 is configured to generate energy for powering the components of the component module 74, and for powering the negative-pressure sleep-apnea-treatment system 70 (FIGS. 4-7) in general. For example, the auxiliary power source 112 can include a spring and a manual winding mechanism that the subject 12 (FIG. 4) can turn to wind the spring so as to store energy in the wound spring; as it unwinds, the spring is configured to drive an electrical generator (also included in the auxiliary power source) that is configured to generate a power signal. Or, the auxiliary power source 112 can include an automatic winding mechanism that winds the spring in response to movement of the auxiliary power source, such as when the subject 12 moves while wearing the system 70; such an automatic winding mechanism can be similar to a conventional mechanism used to wind a spring in a self-winding watch. Alternatively, the auxiliary power source 112 can include a mechanism for automatically driving an electrical generator in response to movement of the auxiliary power source; such a mechanism can be similar to a conventional mechanism used to drive an electrical generator in a self-powered watch. The auxiliary power source 112 can be configured to provide the power signal generated by the electrical generator directly to the power supply 114, or can be configured to charge the battery 110, or another battery that is part of the auxiliary power source, with the generated power signal.

The power supply 114 is configured to receive power from one or more of the receptacle 92 (via the power-switch assembly 100), the battery 110, and the auxiliary power source 112, and to convert this power into one or more currents and voltages that are suitable for powering itself, the other components of the module 74, and any other components of the system 70 (FIGS. 4-7). For example, the power supply 114 can be configured to sense a power signal at the receptacle 92, and to convert this sensed signal into one or more DC power signals having respective DC voltages. Furthermore, the power supply 114 can be configured to charge the battery 110 (and any battery in the auxiliary power source 112) while the power supply is receiving a power signal from the receptacle 92. The power supply 114 also can be configured such that if it does not sense a power signal at the receptacle 92, then it converts a power signal from the auxiliary power source 112 into the one or more DC power signals, and uses any excess power (i.e., a level of power above what is needed to power the components of the sleep-apnea-treatment system 70) from the auxiliary power source to charge the battery 110 (and any battery in the auxiliary power source 112). Further, the power supply 114 can be configured such that if it does not sense a power signal at the receptacle 92 and it senses that the power from the auxiliary power source 112 is insufficient to meet the power demands of the system 70, then it converts a power signal from the battery 110 into the one or more DC power signals, and uses any power from the auxiliary power source to charge the battery. The power supply 114 can be, or can include, any suitable type of power supply, for example, a DC-DC converter such as a buck converter, a boost converter, or a buck-boost converter.

The motor assembly 116 includes one or more motors that are configured to convert electrical energy in the form of a power signal from the power supply 114 into mechanical energy for driving one or more pumps of the pump assembly 118. For example, the motor assembly 116 may include any suitable electrical motor such as a DC motor, a brushless DC motor, a brushed AC synchronous motor, or an induction motor. Furthermore, the motor assembly 116 may include a motor-controller circuit for converting the power signal from the power supply 114 into one or more suitable signals for driving, commutating, and otherwise controlling, the one or more motors. Moreover, the motor assembly 116 can include one or more structures that are configured for cooling the one or more motors, arresting, or otherwise compensating for, vibrations generated by the one or more motors, or muffling sounds generated by the one or more motors so that the motor assembly does not disturb the subject 12 (FIG. 4) while he/she is sleeping.

The pump assembly 118 includes a main pump 142, which is configured to generate a respective negative pressure within each pressure region—a pressure region is further described below in conjunction with FIGS. 14-21—between the collar 76 (FIGS. 4-7) and the neck 50 (FIG. 4) of the subject 12 (FIG. 4) while being driven by the motor assembly 116, and includes an auxiliary pump 144, which is configured to operate independently of the motor assembly. For example, the pump assembly 118 can be mechanically coupled to the motor assembly 116 with, e.g., one or more shafts and transmissions. The main pump 142 can be any suitable fluid pump or compressor, such as an impeller pump or a piston pump. And, like the main pump 142, the auxiliary pump 144 can be any suitable fluid pump or compressor, such as an impeller pump or a piston pump; but unlike the main pump, the auxiliary pump is configured to be drivable independently of the motor assembly 116. For example, the auxiliary pump 144 can include, and can be drivable by, a manual- or self-winding spring mechanism that can be similar to the spring mechanism described above in conjunction with the auxiliary power source 112. Or, the auxiliary pump 144 can include, and can be drivable by, a self-electrical-generator mechanism that can be similar to the self-electrical-generator mechanism described above in conjunction with the auxiliary power source 112.

The pump assembly 118 is configured to engage the main pump 142 while the power supply 114 is providing enough power to operate the motor assembly 116, and to engage the auxiliary pump 144, alone or together with the main pump, while the power supply is not providing enough power to operate the motor assembly. Consequently, the pump assembly 118 is configured to generate a negative pressure even in the absence of power from the supply 114.

The air that the pump assembly 118 pumps from the pressure regions between the collar 76 (FIGS. 4-7) and the subject's neck 50 (FIG. 4) to create the respective negative pressures exits the pump assembly via the air outlet 102.

Furthermore, although described as including a single main pump 142 and a single auxiliary pump 144, the pump assembly 118 may include multiple main pumps or multiple auxiliary pumps.

In addition, to reduce the magnitude of a negative pressure within a pressure region faster than such reduction would occur by only deactivating the main and auxiliary pumps 142 and 144, the pump assembly 118 can include one or more pumps that pump air into the pressure region. Or, the motor assembly 116 or pump assembly 118 can be configured to drive one or more of the main pumps 142 and auxiliary pumps 144 in reverse to pump air into the pressure region to more quickly reduce the magnitude of the negative pressure within the pressure region.

The pressure-regulator assembly 120 and the valve assembly 122 are configured to cooperate to provide a respective negative pressure to each of one or more pressure regions between the neck 50 (FIG. 4) of the subject 12 (FIG. 4) and the collar 76 (FIG. 4), and to regulate these one or more pressures. The valve assembly 122 includes one or more valves that are configured to direct one or more negative pressures to one or more respective pressure regions between the collar 76 (FIGS. 4-7) and the neck 50 (FIG. 4), and the pressure-regulator assembly 120 includes one or more pressure regulators coupled to the valves and configured to regulate these one or more negative pressures to respective pressure levels. For example, the one or more valves can each be one-way valves that allow air to flow from the collar 76 toward the pump assembly 118. And the one or more pressure regulators can each be mechanical, open-loop regulators that bypass any air drawn by the pump assembly 118 in excess of the level of drawn air needed to maintain each of the one or more negative pressures at a respective level. Or, each pressure regulator can employ feedback to the pump assembly 118 or the motor assembly 116, either directly or via the controller 134, to regulate the respective pressures by controlling the pumping power. Furthermore, the one or more pressure regulators and one or more valves can be coupled to each other and to the pressure regions between the collar 76 and the neck 50 via a suitable network of hoses and couplings, which can be part of one or both of regulator and valve assemblies 120 and 122, or which can be separate from these assemblies. Moreover, a pressure regulator of the regulator assembly 120 can be configured to detect an air leak in a pressure region between the collar 76 and the neck 50, and to instruct the sealant dispenser 124, directly or via the controller 134, to dispense a sealant in the vicinity of the air leak in an effort to seal the leak. In addition, one or more of the pressure regulators can each be configured to limit the magnitude of the negative pressure in a respective pressure region to a threshold pressure level that has been determined to be approximately the maximum safe limit for the subject 12. Furthermore, the regulator and valve assemblies 120 and 122 may form part, or all, of a rapid-re-pressurization assembly that is configured to quickly remove the application of negative pressure to the neck 50 of the subject 12 by rapidly increasing the pressure within one or more of the pressure chambers. This rapid re-pressurization may serve to prevent discomfort or injury to the subject 12, and may be manually activated by the subject (e.g., by an emergency or panic button or a voice command) or may be triggered by a sensor in response to, e.g., detecting respiratory-distress sounds abnormal heart activity, or a low blood-oxygen level). And this rapid re-pressurization can include stopping one or more of the pumps of the pump assembly 118, opening a valve (e.g., an emergency valve) or breaking a seal between the neck 50 and one or more sealing surfaces 94 to allow ambient air to enter the one or more of the pressure regions, or taking one or more similar actions.

The sealant-dispenser assembly 124 includes a sealant reservoir 146, and is configured to dispense a sealant from the reservoir to, or near, one or more sealing surfaces 94 (FIGS. 5-6 and 14-15) for the purpose of facilitating, fortifying, and/or repairing an airtight seal between a sealing surface and the neck 50 (FIG. 4) of the subject 12 (FIG. 4). For example, the dispenser assembly 124 can include on or more sealant pumps that can be similar to one or both of the pumps 142 and 144 of the pump assembly 118. Furthermore, the dispenser assembly 124 can include one or more pumps or other structures configured to pressurize the reservoir 146, to apply force to (e.g., squeeze) the reservoir, to push the sealant from the reservoir via a piston, or to take one or more similar actions, so as to transport the sealant from the reservoir. Moreover, the dispenser assembly 124 can be coupled to the reservoir 146 and to the collar 76 via a suitable network of hoses, couplings, and ejection nozzles; these components may be part of, or separate from, the dispenser assembly.

The sealant held in the reservoir 146 can be any suitable substance such as a liquid, gel, cream, or foam that forms a flexible or rigid seal and that does not irritate the subject's skin; examples of such gels include silicone-based gels. Furthermore, the sealant can be configured to form a second seal separate from the seal formed by the sealing surfaces 94 (FIGS. 5-6).

For example, if a pressure regulator of the assembly 120, or a pressure sensor of the assembly 126, senses a leak in one of the pressure regions (described below in conjunction with FIGS. 14-21), then the pressure regulator can instruct the dispenser assembly 124, directly or via the controller 134, to dispense the sealant held in the reservoir 146 at or near one or more of the sealing surfaces 94 (FIGS. 5-6 and 14-15) that border the pressure region. For example, the pressure regulator can be configured to instruct the dispenser assembly 124 to dispense the sealant successively via each sealant-dispense nozzle (e.g., described below in conjunction with FIG. 15) near the one or more sealing surfaces 94 that border the pressure region until the pressure regulator detects that the leak has slowed or stopped. The controller 134, pressure-regulator assembly 120, or another one or more components of the component module 74, can be configured to detect a leak in a pressure region in one or more of the following manners: determining that the speed of a pump within the pump assembly 118 exceeds a threshold level, determining that the energy consumed, or the heat generated, by the pump assembly 118 exceeds a threshold level, determining that the airflow level through the pump assembly exceeds a flow or leak threshold, or by detecting a space between a sealing surface 94 and portion of the subject's neck 50 (FIG. 4) opposite the sealing surface.

The pressure-sensor assembly 126 is configured to generate, and to provide to the controller 134, a respective indication (e.g., a feedback signal) of the pressure in each of the one or more pressure regions formed between the collar 76 (FIG. 4) and the neck 50 (FIG. 4) of the subject 12 (FIG. 4). For example, the pressure-sensor assembly 126 can include a respective pressure sensor (e.g., a piezoelectric vacuum sensor) in each pressure region, or in an air hose coupled to each pressure region. In response to these pressure indications, the controller 134 can be configured to control the pump assembly 118, the pressure-regulator assembly 120, or the valve assembly 122 to maintain the pressure in each pressure region at a respective programmed, or otherwise set, level. Furthermore, if the controller 134 determines that there is a leak in one of the pressure chambers, then the controller can be configured to control the sealant-dispenser assembly 124 to dispense a sealant as described above in an attempt to seal the leak. Moreover, if the controller 134 determines that a pressure in a pressure region has exceeded a threshold pressure level, such as a safety threshold pressure level, then the controller can control the pump assembly 118, the pressure-regulator assembly 120, or the valve assembly 122 to maintain the pressure within the pressure region at or below the safety threshold pressure level. In addition, in response to the one or more pressure indications from the pressure-sensor assembly 126, the controller 134 can implement a peristalsis procedure as described below in conjunction with FIGS. 16-18. In other words, the pump assembly 118, the pressure-regulator assembly 120, the valve assembly 122, the pressure-sensor assembly 124, and the controller 134 form at least part of a feedback loop for maintaining the respective pressure within each of the one or more pressure regions within a respective programmed, or otherwise set, range; alternatively, at least the controller 134 can be omitted from this feedback loop. Furthermore, the pressure-sensor assembly 126 can be configured to perform at least some of the functions of the pressure-regulator assembly 120, and, therefore, can be configured to provide redundancy for these functions. Alternatively, the pressure-sensor assembly 126 can be configured to perform some pressure-related functions, and the pressure-regulator assembly 120 can be configured to perform other pressure-related functions; for example, the pressure-regulator assembly 120 can be configured to prevent the magnitude of the pressure within any pressure region from exceeding a safety threshold pressure level, and the pressure-sensor assembly 126 can be configured to perform all other pressure-related sensing functions.

The apnea-degree-sensor assembly 128 is configured to generate, and to provide to the controller 134, an indication of the degree of sleep apnea being experienced by the subject 12 (FIG. 4) while he/she is sleeping. For example, the apnea-degree-sensor assembly 128 can include one or more sensors that are configured to generate an indication of the degree to which the subject's airway 14 (FIG. 1) is open. In response to this indication, the controller 134 is configured to control the pump assembly 118 or the pressure-regulator assembly 120 to change the pressure in at least one pressure region in a manner that lessens the degree of sleep apnea being experienced by the subject 12. For example, if the apnea-degree-sensor assembly 128 indicates that the degree to which a subject's airway 14 is open is below a target range, then the controller 134 is configured to control the pump assembly 118 or the pressure-regulator assembly 120 to change (e.g., increase) the magnitude of the negative pressure within at least one pressure region so as to increase the degree to which the subject's airway is open in an effort to drive the degree of airway openness into the target range—increasing the degree to which the subject's airway is open can mean, for example, increasing the cross-sectional area of the airway at the location at which it is, or would otherwise become, blocked. In contrast, if the apnea-degree-sensor assembly 128 indicates that the degree to which the subject's airway 14 is open is above the target range, then the controller 134 is configured to control the pump assembly 118 or the pressure-regulator assembly 120 to change (e.g., decrease) the magnitude of the negative pressure within at least one pressure region so as to decrease the degree to which the subject's airway is open in an effort to drive the degree of airway openness into the target range. That is, the pump assembly 118, the pressure-regulator assembly 120, the valve assembly 122, the apnea-degree-sensor assembly 128, and the controller 134 form at least part of a feedback loop for maintaining the degree to which the subject's airway 14 is open within a programmed, or otherwise set, target range so as to reduce (e.g., to zero) the degree of apnea experienced by the subject 12; alternatively, at least the controller 134 may be omitted from this feedback loop. The apnea-degree-sensor assembly 128 is further described below in conjunction with FIGS. 9-13.

The memory 130 can be any suitable type of volatile (e.g., DRAM, SRAM) or nonvolatile (e.g., EPROM, EEPROM, FLASH) memory circuit, is configured to store program instructions that the controller 134 is configured to execute, and is configured to store other software, firmware, and data for the system 70. For example, the memory 130 can be configured to store one or more safety threshold levels, or other threshold levels, for each pressure chamber, to store one or more apnea-degree target ranges, and to store one more configuration or operation parameters for the negative-pressure sleep-apnea system 70 (FIGS. 4-7). Furthermore, the memory 130 can be configured to include a look-up table (LUT) 148, which is configured to correlate a signal level received from the apnea-degree-sensor assembly 128 with a degree of apnea (e.g., a degree to which the subject's airway 14 (FIG. 1) is open) as further described below in conjunction with FIG. 13; the memory can also be configured to store a representation of a curve that correlates the signal level from the apnea-degree-sensor assembly with a degree of sleep apnea.

The temperature-control assembly 132 is configured to control the respective temperature of the one or more pressure regions between the collar 76 (FIGS. 4-7) and the subject's neck 50 (FIG. 4), for example, for the comfort of the subject 12 (FIG. 4) or to reduce the degree of an airway obstruction, or to eliminate an airway obstruction, that a subject experiences during a sleep-apnea event. The assembly 132 can be configured to be coupled to one or more heating elements (e.g., resistive heating elements) and cooling elements (e.g., thermoelectric cooling elements) that are strategically placed around the collar 76 (e.g., inside or on a surface of the collar), and can be configured to be coupled to one or more temperature sensors also so strategically placed; the heating elements, cooling elements, and temperature sensors may be included in the temperature-control assembly, or may be separate from the temperature-control assembly. In response to an indication (e.g., a temperature signal) from one such temperature sensor, the temperature-control assembly 132 can be configured to adjust the temperature in a corresponding pressure region to be within a programmed, or an otherwise set, temperature range. Alternatively, the assembly 132 can be configured to provide the respective indication of temperature for each pressure region to the controller 134, which can be configured to control the heating and cooling elements to maintain the temperature within each of the pressure regions within a respective temperature range. Furthermore, the temperature-control assembly 132 can be coupled to valves that are strategically placed around the collar 76 to vent the one or more pressure regions to the ambient air to help control the respective level of humidity, or the temperature, within each pressure chamber; these valves may form part of the temperature-control assembly or the valve assembly 122, or may be separate from these assemblies. Such valves are further described below in conjunction with FIGS. 14-22. Moreover, the controller 134 can be configured to adjust the temperature within one or more of the pressure regions to reduce a degree of sleep apnea experienced by the subject. For example, cooling the air or skin in one or more of the pressure regions can cause the subject's airway muscles to tense, which in turn can open the subject's airway. The controller 134 can be configured to implement a feedback loop that adjusts the temperature within one or more of the pressure regions to open, and to maintain open, the subject's airway. This loop can be independent of, or combined with, a feedback loop that the controller 134 is configured to implement by adjusting the negative pressure within one or more of the pressure regions to open, and to maintain open, the subject's airway with the smallest magnitude of negative pressure possible. Where these feedback loops are independent, then the controller 134 has at least two variables, pressure and temperature, that it can adjust to open, and maintain open, the subject's airway. The controller 134 and temperature-control assembly 132 can also be configured such that the controller 134 can adjust the temperatures of regions other than the pressure regions to reduce a degree of sleep apnea experienced by the subject. For example, the controller 134 can be configured to adjust the temperature of one or more regions of a subject's neck outside of the pressure regions to reduce a degree of sleep apnea experienced by the subject. In an embodiment, the device can be at a low or "off" pump position unless or until a sleep apnea event is detected, at which point the device pump is triggered "on" or higher power. In an embodiment, the device can have a continuous setting regardless of any sensed sleep apnea events or sleep disturbances.

The controller 134 can include a processor, microprocessor, microcontroller, or any other suitable instruction-executing or non-instruction-executing computing machine and computing circuitry, is configured to control the components of the component module 74 as described above, and can also be configured to control one or more other components of the sleep-apnea system 70 (FIGS. 4-7) in general. The controller 134 can be configured to execute program instructions that are stored in the memory 130, and to use the memory as working memory when performing calculations or otherwise making determinations.

For example, the controller 134 can be configured to operate the sleep-apnea system 70 in a constant-pressure mode. While in this mode, the controller 134 is configured to activate the motor assembly 116 and the pump assembly 118, and then to deactivate the motor assembly and pump assembly in response to one or more pressure sensors of the pressure-sensor assembly 126 indicating that the magnitude of the pressure in one or more pressure regions is at or above a respective first threshold. Next, in response to the one or more pressure sensors of the pressure-sensor assembly 126 indicating that the magnitude of the pressure in one or more of the pressure regions is at or below a respective second threshold, the controller 134 can activate the motor assembly 116 and the pump assembly 118, and can repeat this cycle as often as needed (each of the second thresholds can be lower than the corresponding first threshold to provide hysteresis). In response to one or more sensors of the apnea-degree sensor assembly 128 detecting that the subject 12 (FIG. 4) is experiencing an apnea event, e.g., an airway obstruction, the controller 134 can be configured to increase the first thresholds, or the first and second thresholds, to levels that arrest the apnea event, e.g., remove the obstruction from the airway. Alternatively, the controller 134 can be configured to maintain the negative pressure in the one or more pressure regions inclusively between the first pressure thresholds and the respective second pressure thresholds regardless of whether the subject 12 experiences a sleep-apnea event.

Furthermore, the controller 134 can be configured to operate the sleep-apnea system 70 in an off-until-apnea-detected mode. While in this mode, the controller 134 is configured to deactivate the motor assembly 116 and the pump assembly 118 until one or more sensors of the apnea-degree sensor assembly 128 indicates that the subject 12 (FIG. 4) is experiencing a sleep-apnea event. Then, in response to the one or more sensors detecting a sleep-apnea event, the controller 134 is configured to activate the motor assembly 116 and the pump assembly 118 until one or more sensors of the assembly 128 indicates that the subject is no longer experiencing the sleep-apnea event. Next, the controller deactivates the motor assembly 116 and the pump assembly 118 until the one or more sensors of the assembly 128 detect a next sleep-apnea event. The controller 134 also can be configured to deactivate the motor assembly 116 and the pump assembly 118 if the negative pressure in one or more pressure regions is greater than or equal to a respective first maximum-pressure threshold, regardless of whether the subject 12 is still experiencing the apnea event, and can be configured to reactivate the motor assembly 116 and the pump assembly 118 in response to the negative pressures in all of the pressure regions being less than or equal to respective second maximum-pressure thresholds that are less than the corresponding first maximum-pressure thresholds.

Moreover, the controller 134 can be configured to operate the sleep-apnea system 70 in a low-high mode. While in this mode, the controller 134 is configured to activate the motor assembly 116 and the pump assembly 118 until one or more sensors of the pressure-degree sensor assembly 126 indicate that the magnitude of the negative pressure within one or more pressure regions is, inclusively, between a first (higher) and a second (lower) threshold. Then, in response to one or more sensors of the apnea-degree sensor assembly 128 detecting that the subject 12 (FIG. 4) is experiencing a sleep-apnea event, the controller 134 is configured to activate the motor assembly 116 and the pump assembly 118 until one or more sensors of the pressure-degree sensor assembly 126 indicate that the magnitude of the negative pressure within one or more pressure regions is greater than or equal to the respective first pressure threshold, which is higher than the respective second pressure threshold. Next, in response to one or more sensors of the sleep-apnea sensor assembly 128 detecting that the subject 12 is no longer experiencing the previously detected sleep-apnea event, the controller 134 is configured to deactivate the motor assembly 116 and the pump assembly 118, or otherwise to reduce their outputs, until the one or more sensors of the pressure-sensor assembly 126 indicate that the negative pressure within the one or more pressure regions are each inclusively between the corresponding first threshold and second threshold. The controller 134 can repeat the above cycle in response to one or more sensors of the apnea-degree sensor assembly 128 detecting that the subject 12 is experiencing another sleep-apnea event.

Furthermore, the controller 134 can be configured to change (e.g., reduce) the magnitude of the pressure within each of one or more pressure regions at a set time (e.g., ½ hour, or another set time, before a wakeup time that one has programmed into the system 70 via the input device 88), or in response to an increase in ambient light (e.g., as an indication that it is morning), to assist the subject 12 (FIG. 4) in awakening, or to change (e.g., reduce) the pressure magnitude in response to an indication from the apnea-level-degree sensor assembly 128 that the subject is awakening. For example, the controller 134 can be programmed, or otherwise configured, to begin changing the respective pressure within each of one or more pressure regions at a settable start time, and to control the one or more pressures according to a settable pressure profile for a settable duration that ends at a settable stop time, where the pressure profile can include changing the one or more pressures linearly, or otherwise monotonically, over the settable duration, and where the pressure profile may be common to the one or more pressure regions, or where there may be multiple pressure profiles each associated with a respective group of the one or more pressure regions. As used herein, a "profile" is a plot, or a representation of a plot, of a quantity, such as pressure, over time. And the quantity can have units of, e.g., magnitude, phase, concentration, change in magnitude, change in phase, and change in concentration. Furthermore, a "profile" can include parameters for usage or function of the sleep-apnea system 70 itself, or can include sleep characteristics of the subject 12 (FIG. 4), or other parameters related to the subject, such as identification of the subject, the subject's diet, and the subject's exercise regime. Alternatively, instead of a settable stop time, the controller 134 may stop changing the one or more pressures individually when each of the one or more pressures exceeds a stop threshold, or may stop changing the one or more pressures at about the same time when any one of the one or more pressures exceeds the stop threshold. And, if after the duration of this wake-up procedure the controller 134 determines that the subject 12 (FIG. 4) is still asleep, then the controller can return to treating the subject's sleep apnea in the manner described above. Furthermore, although this wake-up procedure is described in conjunction with the system 70, which generates one or more negative pressures for treating sleep apnea, this wake-up procedure can be modified for a system, such as a CPAP system, that generates one or more positive pressures for treating sleep apnea. Moreover, the controller 134 can implement this procedure for a reason other than waking the subject 12.

Still referring to FIG. 8, alternate embodiments of the component module 74 are contemplated. For example, the module 74 may omit any one or more of the above-described components, or may include one or more other components. Furthermore, one or more of the above-described functions may be performed by one or more components other than the one or more components to which the operation is attributed. Moreover, at least the controller 134 may be implemented in software, firmware, hardware, or a combination or sub-combination of any of software, firmware, and hardware.

FIG. 9 is a diagram of a portion of the apnea-degree-sensor assembly 128 of FIG. 8, and a cross section of the neck 50 (FIG. 4) and airway 14 (FIG. 1) of the subject 12 (FIG. 4), according to an embodiment; although the neck is shown as having a circular cross section and the airway is shown as having a circular cross section, the neck and airway may each have a respective other cross section.

The sensor assembly 128 includes an energy-wave transmitter-receiver 160, which is configured to transmit an energy wave toward the neck 50 and airway 14, to receive portions of the transmitted energy wave redirected (e.g., reflected) by regions of the surface 162 of a wall of the airway, and to determine the degree to which the airway is open in response to the received portions of the energy wave, or to provide information related to the received portions of the energy wave to the controller 134 so that the controller can determine the degree to which the airway is open. Alternatively, the sensor assembly 128 can determine the degree to which the airway 14 is collapsed, or provide information so that the controller 134 can determine the degree to which the airway is collapsed. For example, the sensor assembly 128, or the controller 134, can use the received redirected portions of the energy wave to determine a dimension D of the airway 14, with the value of D corresponding to the degree to which the airway is open (or collapsed). That is, the larger the value of D, the higher the degree to which the airway 14 is open (the lower the degree to which the airway is collapsed), and the smaller the value of D, the lower the degree to which the airway is open (the higher the degree to which the airway is collapsed)—hereinafter, only determining the degree to which the airway is open is described, it being understood that the corresponding description can also apply to determining the degree to which the airway is collapsed. Alternatively, the sensor assembly 128, or the controller 134, can use the received redirected portions of the energy wave to determine more than one dimension of the airway 14, or to acquire an image of the airway and to determine one or more airway dimensions from the acquired image. For example, in an embodiment, the sensor assembly 128, or the controller 134, is configured to determine one or more dimensions of the airway 14, and to determine a cross-sectional area of the airway in response to at least one of the determined one or more dimensions of the airway, and the controller is configured to determine the degree to which the airway is open in response to the determined cross-sectional area of the airway.

The transmitter-receiver 160 can be configured to transmit any suitable type of energy wave that the surface 162 of the airway 14 at least partially redirects. For example, the transmitter-receiver 160 can be configured to transmit an acoustic ultrasound wave such as used in conventional ultrasound machines, or a micro-impulse-radar wave. Furthermore, the transmitter-receiver 160 can be configured to transmit a continuous energy wave, a pulsed energy wave, or any other suitable type of energy wave.

The transmitter-receiver 160 can include multiple transmitters and receivers so as to obtain an "image" of an entire cross section of the airway 14, or can include fewer, or one, transmitter that the sensor assembly 128 sweeps so as to cover an entire cross section of the airway, and fewer, or one, receiver that the sensor assembly sweeps in a similar manner, where the sensor assembly may sweep the transmitter or receiver mechanically or electronically (e.g., as in beam forming with a phased-array radar). If the transmitter-receiver 160 includes multiple transmitters or receivers, then these may be strategically located at various locations inside, or on a surface of, the collar 76 (FIGS. 4-7), or within the component module 74 (FIGS. 4-8). An example of a suitable transmitter and a suitable receiver includes a transducer, e.g., a piezoelectric transducer, that can operate as a transmitter at one time and a receiver at another time.

The sensor assembly 128, or the controller 134, is configured to determine the dimension D of the airway 14 by analyzing one or more of the time delay (e.g., relative to the time of wave transmission), the phase (e.g., relative to the transmitted phase), the frequency spectrum (e.g., relative to the frequency spectrum of the transmitted wave), the wave shape (e.g., relative to the wave shape of the transmitted wave), the power (e.g., relative to the transmitted power), and the amplitude (e.g., relative to the amplitude of the transmitted wave) of each of one or more of the received redirected portions of the energy wave in any suitable manner, such as, for example, in the manner in which an ultrasound machine analyzes received redirected portions of transmitted acoustic waves that are redirected by internal tissues of a subject.

FIG. 10 is a diagram of a portion of the apnea-degree-sensor assembly 128 of FIG. 8, and a cross section of the neck 50 (FIG. 4) and airway 14 (FIG. 1) of the subject 12 (FIG. 4), according to another embodiment; although the neck is shown as having a circular cross section and the airway is shown as having a circular cross section, the neck and airway may each have a respective other cross section.

The sensor assembly 128 includes an energy-wave transmitter 164, which is configured to transmit an energy wave toward the airway 14, and an energy-wave receiver 166, which is configured to receive one or more portions of the transmitted energy wave that penetrate the neck 50 and airway 14, and is configured to determine the degree to which the airway is open in response to the received portions of the energy wave, or to provide information related to the received portions of the energy wave to the controller 134 so that the controller can determine the degree to which the airway is open. For example, the sensor assembly 128, or the controller 134, can use the received portions of the energy wave to determine a dimension D of the airway 14, with the value of D corresponding to the degree to which the airway is open. That is, the larger the value of D, the higher the degree to which the airway 14 is open, and the smaller the value of D, the lower the degree to which the airway is open. Alternatively, the sensor assembly 128, or the controller 134, can use the received portions of the energy wave to determine more than one dimension of the airway 14.

The transmitter 164 can be configured to transmit any suitable type of energy wave that can pass, at least partially, through a first portion of the neck 50 between the transmitter and the airway 14, through the airway, and through a second portion of the neck between the airway and the receiver 166. For example, the transmitter 164 can be configured to transmit an x-ray wave such as used in conventional x-ray machines, or a micro-impulse-radar wave. Furthermore, the transmitter 134 can be configured to transmit a continuous energy wave, a pulsed energy wave, or any other suitable type of energy wave.

The transmitter 164 can include multiple transmitters, and the receiver 166 can include multiple receivers, so that the sensor assembly 128 can obtain an "image" of an entire cross section of the airway 14. Or the transmitter 164 can include fewer, or one, transmitter that the sensor assembly 128 sweeps so as to cover an entire cross section of the airway 14, and the receiver 166 can include fewer, or one, receiver that the sensor assembly sweeps in a similar manner, where the sensor assembly may sweep the transmitter or receiver mechanically or electronically (e.g., as in beam forming with a phased-array radar). If the transmitter 164 includes multiple transmitters, or the receiver 166 includes multiple receivers, then these may be strategically located at various locations inside, or on a surface of, the collar 76 (FIGS. 4-7), or within the component module 74 (FIGS. 4-8).

The sensor assembly 128, or the controller 134, is configured to determine the dimension D by analyzing one or more of the time delay (e.g., relative to the time of wave transmission), the phase (e.g., relative to the transmitted phase), the frequency spectrum (e.g., relative to the frequency spectrum of the transmitted wave), the wave shape (e.g., relative to the wave shape of the transmitted wave), the power (e.g., relative to the transmitted power), and the amplitude (e.g., relative to the amplitude of the transmitted wave), of each of one or more of the received portions of the energy wave in any suitable manner, such as, for example, in the manner in which an x-ray machine analyzes received portions of transmitted x-ray waves.

FIG. 11 is a diagram of a portion of the apnea-degree-sensor assembly 128 of FIG. 8, and of the subject 12 of FIG. 4, according to yet another embodiment.

The sensor assembly 128 includes an energy-wave receiver 168, which is configured to receive one or more portions of one or more energy waves generated by the subject 12, and is configured to determine the degree to which the subject's airway 14 (FIGS. 9-10) is open in response to the received one or more energy-wave portions, or to provide information related to the received one or more energy-wave portions to the controller 134 so that the controller can determine the degree to which the airway is open. For example, the sensor assembly 128, or the controller 134, can use the received one or more energy-wave portions to determine a dimension D (FIGS. 9-10) of the airway 14, with the value of D corresponding to the degree to which the airway is open. That is, the larger the value of D, the higher the degree to which the airway 14 is open, and the smaller the value of D, the lower the degree to which the airway is open. Alternatively, the sensor assembly 128, or the controller 134, can use the received one or more energy-wave portions to determine more than one dimension of the airway 14.

The energy-wave receiver 168 can be configured to receive any suitable type of energy wave that the subject 12 generates. For example, the receiver 168 can be configured to receive an acoustic wave, such as generated when the subject 12 makes respiratory sounds (e.g., breathing or snoring sounds), a disturbance in a light wave, such as generated when the subject moves his eyes (even when the eyes are closed) or another body part (e.g., nose, mouth, jaw, or chin), or an electromagnetic wave such as a brain wave or a heart wave (e.g., an electrocardiogram wave).

The sensor assembly 128 can include multiple receivers 168 so as to be able to pick up energy waves emanating from anywhere around the head region, neck region, or other region of the subject 12, or can include fewer, or one, receiver that the sensor assembly sweeps mechanically or electronically (e.g., as in beam forming with a phased-array radar). If the sensor assembly 128 includes multiple receivers 168, then these may be strategically located at various locations inside, or on a surface of, the collar 76 (FIG. 4), or within the component module 74 (FIGS. 4-8). Furthermore, the one or more receivers 168 may be directed at regions (e.g., head, chest) of the subject other than the subject's neck.

The sensor assembly 128, or the controller 134, is configured to determine the dimension D by analyzing one or more of the phase, the frequency spectrum, the wave shape, the power, and the amplitude of each of one or more of the received energy-wave portions in a conventional manner, and then correlating the results of this analysis with a degree to which the airway 14 (FIGS. 9-10) is open using, for example, the look-up table 148 of FIG. 8 or a fitted curve. A procedure for developing and using such a correlation is described below in conjunction with FIG. 13.

FIG. 12 is a diagram of a portion of the apnea-degree-sensor assembly 128 of FIG. 8, and of the subject 12 of FIG. 4, according to still another embodiment.

The sensor assembly 128 includes a biological-condition sensor 170, which is configured to sense one or more biological conditions of the subject 12, and is configured to determine the degree to which the subject's airway 14 (FIGS. 9-10) is open in response to the one or more sensed biological conditions, or to provide information related to the sensed one or more biological conditions to the controller 134 so that the controller can determine the degree to which the airway is open. For example, the sensor assembly 128, or the controller 134, can use the sensed one or more biological conditions to determine a dimension D (FIGS. 9-10) of the airway 14, with the value of D corresponding to the degree to which the airway is open. That is, the larger the value of D, the higher the degree to which the airway 14 is open, and the smaller the value of D, the lower the degree to which the airway is open. Alternatively, the sensor assembly 128, or the controller 134, can use the sensed one or more biological conditions to determine more than one dimension of the airway 14.

The sensor 170 can be configured to sense any suitable type of biological condition of the subject 12. Examples of such a biological condition include respiratory rate, heart rate, blood-glucose level, blood-oxygen level, blood-adrenaline level, body temperature, body-perspiration level, body-cortisol level (from cortisol in the subject's sweat) body-movement level (e.g., the sensor can include an accelerometer), blood pressure, expiration-gas composition, and body-part position (e.g., chin position, the degree to which the subject's mouth is open, or the degree to which the subject's nostrils are flared).

The sensor assembly 128 can include multiple biological-condition sensors 170 so as to be able to sense multiple biological conditions of the subject 12, and the one or more sensors may be strategically located at various locations inside, or on (removably or fixedly attached to) a surface of, the collar 76 (FIGS. 4-7), within the component module 74 (FIGS. 4-8), or even on or in the subject's body, in which case each such sensor can be tethered to the component module 74 (FIGS. 4-8) with a wire or other suitable connector, or can communicate with a base portion of the sensor assembly 128 wirelessly. For example, the sensor assembly 128 can utilize one or more motion sensors configured to monitor motion of the sleeping subject 12. These one or more sensors can be on-board the collar assembly 72 (e.g., one or more accelerometers), or can be remote from the collar assembly (e.g., accelerometers attached to the limbs or torso of the subject, or remote imagers, e.g., low-light or IR cameras, or micro-impulse radar). A sensor that is remote from the collar assembly 72 can deliver its measurements to a portion of the sensor assembly 128 that is on-board the collar assembly wirelessly or via one or more signal cables.

In response to readings provided by such one or more sensors, the controller 134 can interpret excessive motion (e.g., thrashing, or frequent posture changes) or lack of motion (e.g., excessive stillness) of the subject 12 as an indication that the subject is experiencing sleep apnea.

The sensor assembly 128, or the controller 134, is configured to determine the dimension D by analyzing one or more parameters of each of one or more of the sensed biological conditions in any suitable manner, and then correlating the results of this analysis with a degree to which the airway 14 (FIGS. 9-10) is open using, for example, the look-up table 148 of FIG. 8, or a fitted curve stored in the memory 130. A procedure for developing and using such a correlation is described below in conjunction with FIG. 13.

Referring to FIGS. 8-12, alternate embodiments of the apnea-degree-sensor assembly 128 are contemplated. For example, the sensor assembly 128 can include any combination or sub-combination of one or more of each of the energy-wave transmitter-receiver 160, the energy-wave transmitter 164, the energy-wave receivers 166 and 168, and the biological-condition sensor 170.

FIG. 13 is a flow diagram 180 of a procedure for correlating one or more biological conditions of the subject 12 (e.g., FIG. 12) to a degree of sleep apnea that the subject is experiencing, according to an embodiment. For example, the procedure may correlate the one or more biological conditions to a degree to which the subject's airway 14 (e.g., FIGS. 9-10) is open, the degree of airway openness being related to the degree of sleep apnea that the subject is experiencing. In the example described below in conjunction with the flow diagram 180, the correlated biological condition is the respiratory rate of the subject 12, although it is understood that any one or more other biological conditions sensed by any of the embodiments of the apnea-degree-sensor assembly 128 described above in conjunction with FIGS. 8-12 can be correlated in a similar manner. Furthermore, a sleep doctor or sleep technician can perform the correlation with the subject 12 in a sleep-laboratory setting, and then, for example, program the look-up-table (LUT) 148 (FIG. 8) of the subject's sleep-apnea-treatment system 70 with a correlation-data structure, or program the memory 130 (FIG. 8) of the system with a representation of a fitted curve that relates the biological condition to the degree of sleep apnea. Alternatively, the subject's system 70, or a laboratory version of the system, may perform this procedure with or without the assistance of a sleep-medicine professional or the subject 12.

At a step 182, one, e.g., a sleep technician, monitors a degree to which the airway 14 (FIGS. 9-10) of the subject 12 (FIG. 4) is open while the subject is sleeping. For example, one may use ultrasound to monitor one or more dimensions D (FIGS. 9-10) of the airway 14 as described above in conjunction with FIG. 9. The ultrasound waves and resulting ultrasound images may be generated by an embodiment of the apnea-treatment system 70 described above in conjunction with FIG. 9, or may be generated by an independent ultrasound machine.

Simultaneously at a step 184, one also monitors one or more biological conditions of the subject 12 (FIG. 4) that are related to the degree to which the subject's airway 14 (FIGS. 9-10) is open while the subject is sleeping. For example, one may monitor the volume or frequency spectrum of the subject's respiratory sounds (e.g., breathing, snoring), or, as in this example, the subject's respiratory rate.

Then, after performing steps 182 and 184 for a suitable period of time (e.g., 2-8 hours while the subject is sleeping), at a step 186, one correlates each of the monitored one or more biological conditions to the degree of openness of the airway 14 (FIGS. 9-10). For example, one may digitize the observed values of the subject's respiratory rate at corresponding sample times, digitize the observed values of the degrees of openness of the subject's airway 14 at the same corresponding sample times, and match each value of the respiratory rate taken at a respective sample time with the corresponding degree of airway openness taken at the same respective sample time. Furthermore, in some cases, a predictive correlation can be derived. For example, it may be determined that during a period (e.g., two-minutes long) preceding an apnea-inducing closure of the airway 14 of the subject 12, a particular pattern of respiratory sounds often precedes the airway closure. Therefore, such a correlation can be used to preemptively apply negative pressure to a selected one or more regions of the subject's neck 50 to prevent the onset of a sleep-apnea event before it even occurs.

Next, at a step 188, one generates a respective data structure that represents the correlation between each of the biological conditions to the degree of airway openness.

For example, on may generate a data structure that represents the correlation of the digitized values of the respiratory rate with the corresponding digitized values of the degree of airway openness, and store this data structure in the LUT 148 (FIG. 8). That is, one may associate each of the values of the respiratory rate with a corresponding address of the LUT 148, and, at each address, store the degree of airway openness corresponding to the value of the respiratory rate associated with the address.

When the apnea-degree-sensor assembly 128 (FIGS. 8 and 12) provides a digitized value of the subject's respiratory rate, a respiratory-rate-value-to-address converter (such a converter can be part of the assembly 128, can be part of any other component of the component module 74, or can be a separate component of the component module) converts the value into an address of the LUT 148. And the sensor assembly 128, or the controller 134, obtains the corresponding value of the degree of airway openness from the location of the LUT 148 at this address, and uses this value of the degree of airway openness to control the pump assembly 118 (FIG. 8), pressure-regulator assembly 120, or valve assembly 122 so as to control the level of sleep apnea experienced by the subject 12. For example, if the value of the degree of airway openness obtained from the LUT 148 is below a programmed, or otherwise set, apnea-level target range, then the sensor assembly 128 or controller 134 can act to increase the degree of airway openness toward the target range; in contrast, if the value of the degree of airway openness obtained from the LUT is above the apnea-level target range, then the sensor assembly 128 or controller 134 can act to decrease the degree of airway openness toward the target range, or to maintain the degree of airway openness at its present level.

Alternatively, one may fit the digitized values of the respiratory rate and the corresponding digitized values of the degree of airway openness to a curve, and store a representation of this curve in the memory 130 (FIG. 8).

When the apnea-degree-sensor assembly 128 (FIGS. 8 and 12) provides a digitized value of the subject's respiratory rate, the controller 134 converts the value into a corresponding value of the degree of airway openness using the representation of the fitted curve, and uses this value of the degree of airway openness to control the pump assembly 118 (FIG. 8), pressure-regulator assembly 120, or valve assembly 122 so as to control the level of sleep apnea experienced by the subject 12. For example, if the fitted curve is a straight line, then the mathematical expression defining the line in terms of the respiratory-rate values and the degree-of-airway-openness values is stored in the memory 130, and the controller 134 uses this mathematical expression to calculate the degree of airway openness that corresponds to the provided value of the respiratory rate. So, if the value of the degree of airway openness obtained from the fitted curve is below a programmed, or otherwise set, apnea-level target range, then the sensor assembly 128 or controller 134 can act to increase the degree of airway openness toward the target range; in contrast, if the value of the degree of airway openness obtained from the fitted curve is above the apnea-level target range, then the sensor assembly 128 or controller 134 can act to decrease the degree of airway openness toward the target range, or to maintain the degree of airway openness at its present level.

Still referring to FIG. 13, alternate embodiments of the procedure represented by the flow diagram 180 are contemplated. For example, any one or more of the recited steps 182-188 may be omitted, and one or more other steps may be added. Furthermore, any of the recited steps may be performed manually, by a computing apparatus, or by any other suitable apparatus.

Figure 14:
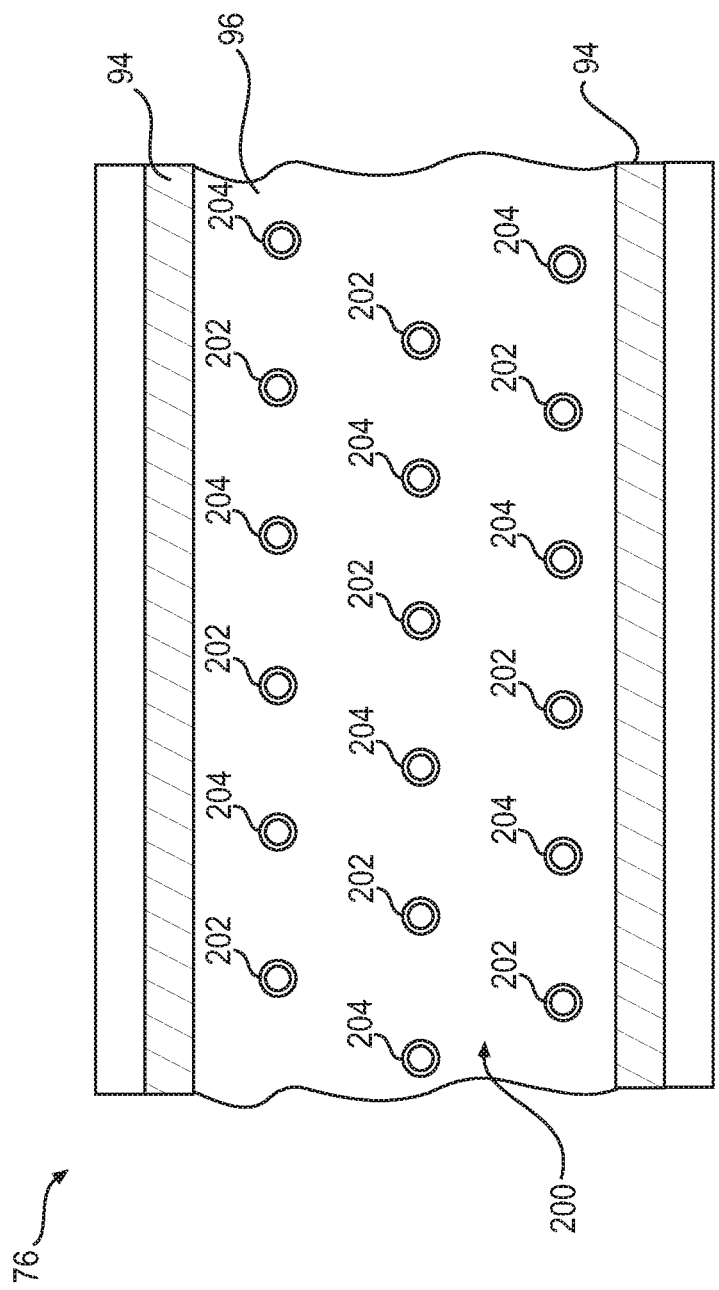
FIG. 14 is a diagram of sealing and vacuum surfaces of the collars of FIGS. 4-7, according to an embodiment.

FIG. 14 is a plan view of an inner portion of the collar 76 of FIGS. 4-7, including portions of two sealing surfaces 94 and a portion of vacuum surface 96, according to an embodiment. "Inner portion" means a portion of the collar 76 that is configured to face the neck 50 (FIG. 4) of the subject 12 (FIG. 4) while the subject is wearing the sleep-apnea-treatment system 70 (FIGS. 4-7).

The sealing surfaces 94 are each configured to contact a respective portion of the neck 50 (FIG. 4) of the subject 12 (FIG. 4), and to form a respective airtight seal with the respective contacted neck portion.

And the vacuum surface 96 is configured to form a negative-pressure region 200 together with the sealing surfaces 94, the contacted portions of the neck 50, and the portion of the subject's neck opposite the vacuum surface—the vacuum surface may also be called a pressure surface, and the negative-pressure region may also be called a vacuum region, pressure chamber, or vacuum chamber. As described below in conjunction with FIGS. 16-22, the collar 76 can include a frame such that at least a portion of the vacuum surface 96 does not contact the subject's neck 50.

Each sealing surface 94 can be rigid, semi-rigid, or flexible, and may be formed from any suitable sealing material, such as plastic, rubber, foam, or silicone.

The vacuum surface 96 also can be rigid, semi-rigid, or flexible, can be formed from any suitable material, such as plastic, rubber, foam, or silicone, and includes a set of one or more inlet openings 202, and a set of one or more outlet openings 204; the inlet and outlet openings can be arranged relative to each other in any suitable pattern, and can have any suitable sizes and shapes. Furthermore, nozzles, one-way valves, or other suitable components may be disposed within one or more of the openings 202 and 204.

The one or more inlet openings 202 are configured to allow air to flow from an outer portion of the collar 76, through one or more inlet valves (described below in conjunction with FIGS. 16-22), through the one or more inlet openings, and into the negative-pressure region 200—"outer portion" means a portion of the collar 76 that is configured to face away from the neck 50 (FIG. 4) of the subject 12 (FIG. 4) while the subject is wearing the sleep-apnea-treatment system 70 (FIGS. 4-7). Hoses and couplings within the collar 76 can couple the one or more inlet openings 202 to the one or more inlet valves. Furthermore, some or all of these hoses and couplings, the one or more inlet valves, and the one or more inlet openings 202 can be considered to be part of the valve assembly 122 (FIG. 8).

And the one or more outlet openings 204 are configured to allow air to flow from the negative-pressure region 200, through the one or more outlet openings, through the valve assembly 122 (FIG. 8) and the pressure-regulator assembly 120 (FIG. 8), through the pump assembly 118 (FIG. 8), and out through the outlet valve 102 (FIGS. 4-8). Hoses and couplings within the collar 76 can couple the one or more outlet openings 204 to the valve and pressure-regulator assemblies 120 and 122 (FIG. 8). Furthermore, some or all of these hoses and couplings and the one or more outlet openings 204 can be considered to be part of the valve assembly 122 (FIG. 8).

Allowing air to flow through the negative-pressure region 200 may be more comfortable for the subject 12 (FIG. 4) than if no inlet openings 202 were present, because without one or more inlet openings, the air within the pressure region could become hot or humid due to the subject perspiring, and could become otherwise "stale." Even though the negative-pressure sleep-apnea treatment system 70 (FIGS. 4-7) can include the temperature-control assembly 132 (FIG. 8) to cool the air within the pressure region 200, the above-described airflow can reduce or eliminate the need for such cooling, and, therefore, can reduce the energy that the system consumes, and can allow one to reduce the cost of the system by omitting the cooling capability from the temperature-control assembly.

Still referring to FIG. 14, alternate embodiments of the sealing surfaces 94 and vacuum surface 96 are contemplated. For example, although shown arranged parallel to one another, the sealing surfaces 94 can be arranged with any other suitable orientation relative to one another. Furthermore, the collar 76 can include fewer or more than two sealing surfaces 94, and more than one vacuum surface 96. Moreover, one or more of the sealing surfaces 94 can each include one or more outlet openings 204 to increase the strength of the seal that the respective surfaces make with the neck 50 (FIG. 4). In addition, one or more portions of a sealing surface 94 and one or more portions of a vacuum surface 96 can be parts of a same surface. Furthermore, the portion of the vacuum surface 96 that forms a respective pressure region 200 can be fully or partially surrounded by one or more sealing surfaces 94 (if partially surrounded, then part of the vacuum surface can form the remainder of the seal around the pressure region by forming an airtight seal with a portion of the subject's neck 50 (FIG. 4) opposite the sealing portion of the vacuum surface). Moreover, the airtight seal that the one or more sealing surfaces 94 and one or more vacuum surfaces 96 form with respective portions of the subject's neck 50 (FIG. 4) to form a pressure region 200 can extend only partially around the pressure region; this can, for example, eliminate the need for the inlet openings 202, because the pump assembly 118 (FIG. 8) can draw in outside air through a side of the pressure region where no airtight seal is formed. In addition, one or more sealing surfaces 94 can each include one or more outlet openings 204, which enable each sealing surface to use negative pressure to form a seal against the skin of the subject. The one or more sealing surfaces 94 can each include an array of closely spaced discrete outlet openings 204, or can include a porous surface. The outlet openings 204 or pores in the one or more sealing surfaces can be coupled through a manifold or plenum to a pump (e.g., belonging to the pump assembly 118, pressure-regulator assembly 120, or valve assembly 122), which is used to provide the negative pressure causing the sealing surface to adhere to the skin of the user. The one or more negative-pressure levels that form the one or more seals can be different from the one or more negative-pressure levels in the one or more pressure regions 200. Alternatively, the pressure level used to form a seal and the pressure level in an adjacent pressure region 200 can be the same; for example, a manifold servicing the outlet openings/pores of a sealing surface 94 can couple the outlet openings/pores to the adjacent pressure region, thereby not requiring a separate pump.

Figure 15:
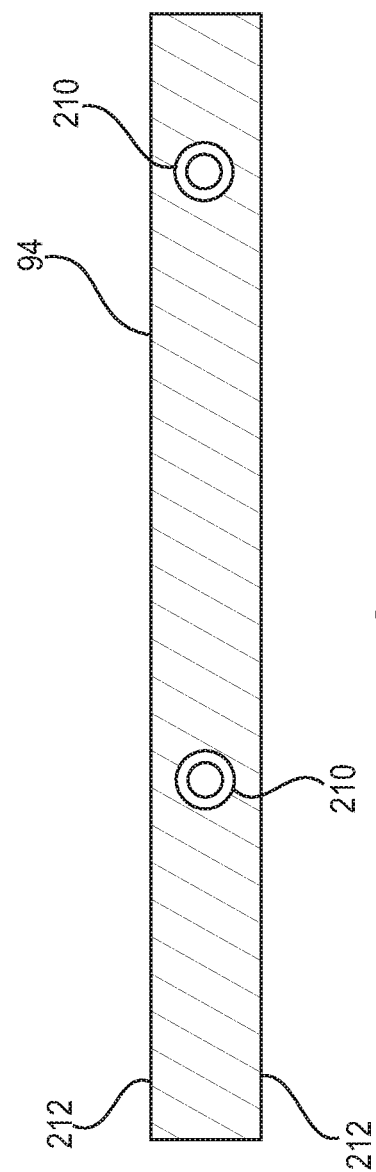
FIG. 15 is a diagram of a sealing surface of the collars of FIGS. 4-7, according to another embodiment.

FIG. 15 is a plan view of a portion of a sealing surface 94, according to an embodiment.

The portion of the sealing surface 94 of FIG. 15 can be similar to the portions of the sealing surfaces 94 of FIG. 14, except that the portion of the sealing surface of FIG. 15 includes one or more sealant-dispensing openings 210.

Each sealant-dispensing opening 210 is configured to eject a sealant from the sealant-dispersing assembly 124 of FIG. 8, where the sealant is configured to fortify, or repair a leak in, the airtight seal that the sealing surface 94 is configured to form with a portion of the neck 50 (FIG. 4) of the subject 12 (FIG. 4) as described above in conjunction with FIG. 14. For example, the sealant may repair a leak formed around one or more strands of the subject's hair that lay between the sealing surface 94 and the subject's neck 50 (FIG. 4). Furthermore, nozzles, one-way valves, or other suitable components may be disposed within one or more of the openings 210. Moreover, hoses and couplings within the collar 76 (FIG. 14) can couple the one or more sealant-dispensing openings 210 to the sealant-dispenser assembly 124 (FIG. 8); some or all of these hoses and couplings, and the one or more sealant-dispensing openings, can be considered to be part of the sealant-dispenser assembly. In addition, the one or more sealant-dispensing openings 210 can have any suitable sizes and shapes, and can be located at any suitable spacing and in any suitable pattern along the sealing surface 94. Furthermore, an opening 210 can overlap an edge 212 of the sealing surface 94 such that one portion of the sealant-dispensing opening is formed in the sealing surface, and another portion is formed in the adjacent vacuum surface 96 (FIG. 14). Or, an opening 210 can be formed entirely in the vacuum surface 96, for example, near an edge 212 of the sealing surface 94.

In operation of the sleep-apnea system 70 (FIGS. 4-7), according to an embodiment, if, for example, the controller 134 (FIG. 8) detects a leak in a pressure region 200 (FIG. 14), then the controller can cause the sealant-dispenser assembly 124 (FIG. 8) to dispense a sealant from the reservoir 146 (FIG. 8) via one or more of the sealant-dispensing openings 210 along a portion of a sealing surface 94 that forms, or otherwise borders, the pressure region. For example, the controller 134 can cause the sealant-dispenser assembly 124 to dispense sealant from one opening 210 in the sealing surface 94 at a time until the controller detects that the leak has been sealed.

Still referring to FIG. 15, alternate embodiments are contemplated. For example, although only one sealing surface 94 is described, multiple sealing surfaces can include one or more sealant-dispensing openings 210. Furthermore, the sealant-dispenser assembly 124 (FIG. 8) can be configured to selectively dispense a sealant from one or more, but not all, of the sealant-dispensing openings 210 at any one time. Moreover, if an opening 210 includes a nozzle, then the sealant-dispenser assembly 124 may be able to orient the nozzle in a selected direction before, while, or after dispensing the sealant.

FIG. 16 is a view of a portion 220 of the collar 76 of FIGS. 4-7 and 14, according to an embodiment.

FIG. 17 is a cross-sectional view of a mid region of the collar portion 220 of FIG. 16 taken along a line A-A of FIG. 16, and of a portion 222 of a subject's neck 50 and airway 14, according to an embodiment.

Figure 18:
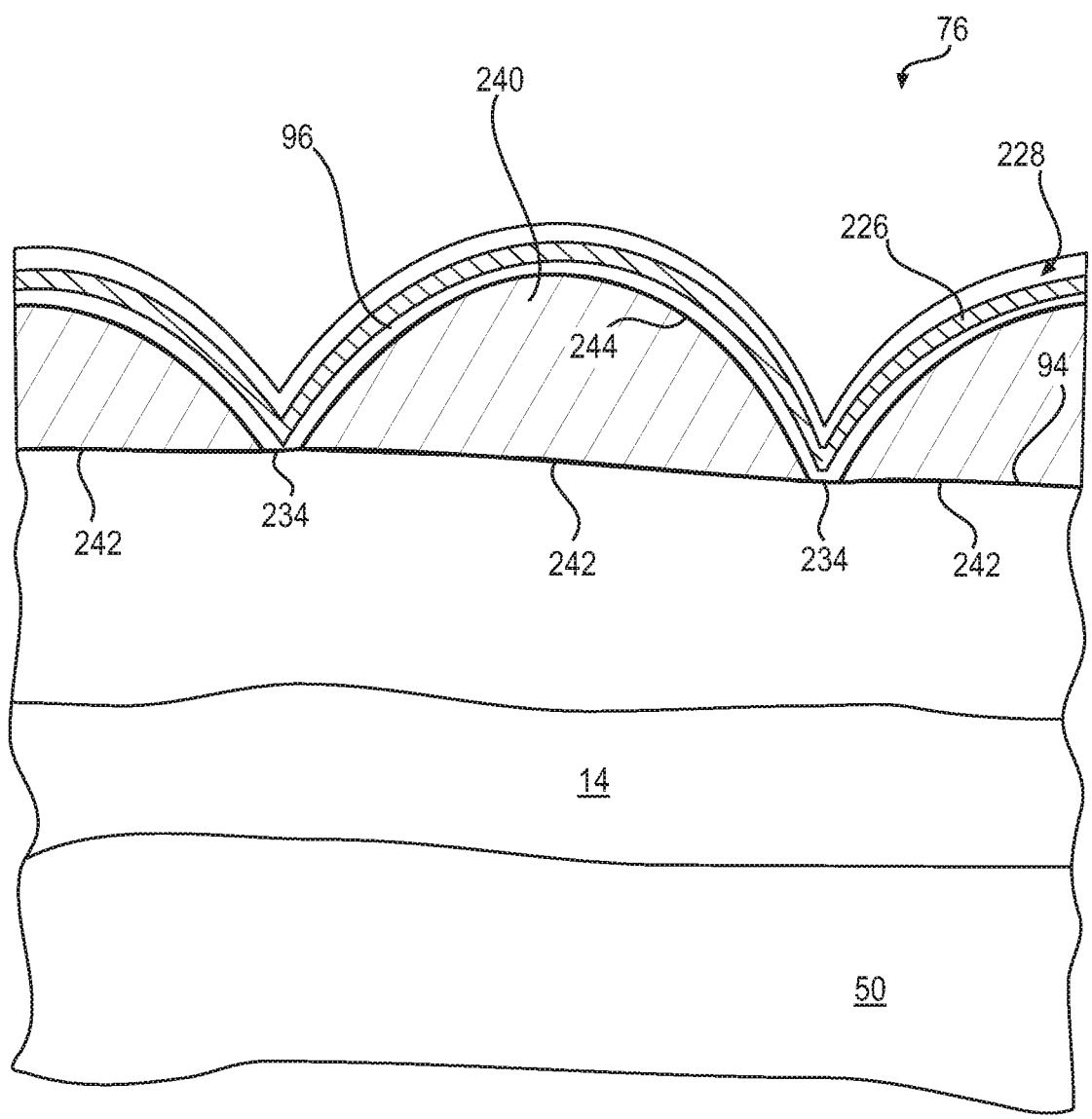
FIG. 18 is a view of an end region of the collar portion of FIG. 16, according to an embodiment.

FIG. 18 is a cross-sectional view of an end region of the collar portion 220 of FIG. 16, and of the portion 222 of the subject's neck 50 and airway 14, according to an embodiment.

Referring to FIGS. 16-17, the collar 76 includes one or more segments 224, which, while the negative-pressure sleep-apnea-treatment system 70 (FIGS. 4-7) is being worn by the subject 12 (FIG. 4), are configured to be oriented approximately in a circumferential direction around the subject's neck 50.

Each segment 224 is formed by a respective rigid, or semi-rigid, portion 226 of a frame 228. Each frame portion 226 has a curved shape, and can be made from any suitable material such as a plastic, a metal, or a wire mesh.

To each frame portion 226 is attached a respective portion of the vacuum surface 96 (described above in conjunction with, e.g., FIG. 14), and a respective portion of an outer covering 230, which can be made from any suitable material such as a plastic or a cloth. Any suitable attachment technique, such as cementing or gluing, may be used to attach the vacuum surface 96 and outer covering 230 to the frame portions 226.

Each frame portion 226 is attached to an adjacent frame portion at a respective joint 232 by any suitable attachment technique such as welding, bonding, cementing, or gluing. Alternatively, the frame 228 may be made from one piece such that the frame portions 226 are integral with one another. Or, the joints 232 may be flexibly coupled together, e.g., with hinges.

A respective sealing surface 94 (described above in conjunction with FIGS. 14-15) is disposed along each joint 232.

While the collar 76 is being worn by the subject 12 (FIG. 4), the sealing surfaces 94 engage respective portions 234 of the subject's neck 50 so as to form the pressure regions 200, one pressure region per collar segment 224 in this example.

Each collar segment 224 also includes a respective inlet valve 238, which allows the pump assembly 118 (FIG. 8) to draw outside air into the respective pressure regions 200 as described above in conjunction with FIG. 14.

Any hoses or couplings that may be disposed in the collar 76, for example as described above in conjunction with FIGS. 8 and 14-15, are omitted from FIGS. 16-18 for clarity.

Referring to FIG. 18, the cross section of an end region of the collar 76 is similar to the cross section of the mid region of the collar as described above in conjunction with FIG. 17, but with the addition of segment terminators 240.

The terminators 240 are configured to form airtight seals at the ends of the collar segments 224, and may be made from any suitable rigid or semi-rigid material such as plastic, metal, or wire mesh.

The sealing surfaces 94 extend along the bottoms of the terminators 240 and are configured to make airtight seals with portions 242 of the neck 50, and the curved tops of the terminators are attached to the vacuum surfaces 96 along seams 244 in any suitable airtight manner.

Alternately, the terminators 240 may be attached directly to the respective frame portions 226, or may be formed integrally with the frame portions or as an integral part of the frame 228 as a whole.

Referring to FIGS. 16-18, in operation of the sleep-apnea-treatment system 70 (FIGS. 4-7), according to an embodiment, the pump assembly 118 (FIG. 8) is configured to cause a negative pressure to exist within the negative-pressure regions 200 by drawing air from these regions; although the inlet valves 238 allow a flow of air into the negative-pressure regions, the power of the pump assembly overcomes this airflow to create the negative pressures within the negative-pressure regions. Furthermore, the negative pressures within the regions 200 may be the same or different from one another.

Because the pressure outside of the collar 76 is greater than the pressure within the pressure regions 200, the outside air effectively presses against the frame 228, which in turn presses the sealing surfaces 94 against the neck portions 234 and 242 to form respective airtight seals. Or, viewed another way, the frame 228 is effectively "sucked" against the neck 50 such that the sealing surfaces 94 are forced against the respective neck portions 234 and 242. This effect can be used as the primary mechanism for attaching the collar assembly 72 to the neck 50 of the subject 12, thus enabling a collar assembly that does not need to be positively attached to the subject via straps or by fully encircling the neck. Such a collar assembly 72 can generically utilize, in one or more of the pressure regions 200, a modest "gripping" level of negative pressure that is sufficient to hold the collar assembly against the subject's neck 50, but that is too weak to appreciably open his/her airway 14; and the collar assembly can increase the magnitude of the negative pressure in one or more of the pressure regions as needed to open the subject's airway 14, or to maintain the airway open, so as to arrest an apnea, or to prevent an apnea from occurring.

Furthermore, because the frame 228 and terminators 240 are rigid or semi-rigid, the frame portions 226 and the terminators hold the vacuum surfaces 96 away from the portions 246 of the neck 50 covered by the frame portions. Therefore, the negative pressure within the regions 200 can cause the neck portions 246 to expand outward, thus giving the desired result of "pulling" open the subject's airway 14. If the frame portions 226 and terminators 240 were not rigid or semi-rigid, then the vacuum surfaces 96 would collapse against the neck portions 246 such that the subject's airway 14 would not be "pulled" open as intended.

Still referring to FIGS. 16-18, in operation of the sleep-apnea-treatment system 70 (FIGS. 4-7), according to another embodiment, the system may regulate the pressures within the pressure regions 200 in a manner that mimics peristalsis. For example, the system 70 can so regulate the pressures to reduce or eliminate the chances that the system will cause a portion 246 of the neck 50 to form an edema (e.g., a "hickey") caused by a prolonged continuous exposure to a negative pressure.

Peristalsis is a radially symmetrical contraction and relaxation of muscles that form a muscular tube, which contraction propagates in a wave down the muscular tube in an anterograde fashion. An example of such a muscular tube in humans is the esophagus, the muscles of which contract in a peristalsis manner to move food and drink from the mouth to the stomach.

In an embodiment, the pressure-regulator assembly 120 (FIG. 8) first increases the pressure (i.e., lessens the magnitude of the negative pressure) within the bottom pressure region 200 of the collar 76 while maintaining the pressures in the middle and top pressure regions unchanged. The amount and profile by which the pressure-regulator assembly 120 increases the pressure in the bottom pressure region 200, and the duration of this pressure increase, can be suitable to reduce or eliminate the chances of an edema forming in the bottom neck portion 246 without breaking the airtight seal formed between the adjacent sealing surfaces 94 and neck portions 234 and 242.

Next, the pressure-regulator assembly 120 (FIG. 8) decreases the pressure (i.e., increases the magnitude of the negative pressure) within the bottom pressure region 200 until it reaches the level that the controller 134 (FIG. 8) determines is suitable to treat the subject's sleep apnea. The profile by which the pressure-regulator assembly 120 reduces the pressure within the bottom pressure region 200, and the duration of this pressure reduction, can be suitable to reduce or eliminate the chances of an edema forming in the bottom neck portion 246.

Then, while or after reducing the pressure in the bottom negative-pressure region 200, the pressure-regulator assembly 120 (FIG. 8) increases the pressure (i.e., lessens the magnitude of the negative pressure) within the middle pressure region 200 while maintaining the pressure in at least the top pressure region unchanged. The amount and profile by which the pressure-regulator assembly 120 increases the pressure within the middle pressure region 200, and the duration of this pressure increase, can be suitable to reduce or eliminate the chances of an edema forming in the middle neck portion 246 without breaking the airtight seal formed between the adjacent sealing surfaces 94 and neck portions 234 and 242.

Next, the pressure-regulator assembly 120 (FIG. 8) decreases the pressure (i.e., increases the magnitude of the negative pressure) within the middle pressure region 200 until it reaches the level that the controller 134 (FIG. 8) determines is suitable to treat the subject's sleep apnea. The profile by which the pressure-regulator assembly 120 reduces the pressure in the middle pressure region 200, and the duration of this pressure reduction, may be suitable to reduce or eliminate the chances of an edema forming in the middle neck portion 246.

Then, while or after reducing the pressure in the middle negative-pressure region 200, the pressure-regulator assembly 120 (FIG. 8) increases the pressure (i.e., lessens the magnitude of the negative pressure) within the top pressure region 200 while maintaining the pressure in at least the bottom pressure region unchanged. The amount and profile by which the pressure-regulator assembly 120 increases the pressure within the top pressure region 200, and the duration of this pressure increase, can be suitable to reduce or eliminate the chances of an edema forming in the top neck portion 246 without breaking the airtight seal formed between the adjacent sealing surfaces 94 and neck portions 234 and 242.

Next, the pressure-regulator assembly 120 (FIG. 8) decreases the pressure (i.e., increases the magnitude of the negative pressure) within the top pressure region 200 until it reaches the level that the controller 134 (FIG. 8) determines is suitable to treat the subject's sleep apnea. The profile by which the pressure-regulator assembly 120 reduces the pressure within the top pressure region 200, and the duration of this pressure reduction, may be suitable to reduce or eliminate the chances of an edema forming in the top neck portion 246.

In summary of the above-described peristalsis procedure, the controller 134 changes the pressures within the bottom, middle, and top pressure regions so that these pressures are offset from each other in time, and, therefore, in phase, and so that the controller effectively generates a pressure "wave" that propagates up or down the collar 76.

The controller 134 (FIG. 8) may perform this peristalsis procedure periodically at a programmed, or otherwise set, interval, or may do so in response to a sensor of the system 70 indicating that an edema of a threshold size has formed, or may soon form, in a region (e.g., a region 246) of the subject's neck 50. Furthermore, the controller 134 can cause one or more of the pressure regions 200 to have a respective positive pressure during respective portions of the peristalsis procedure, as long as the number of pressure regions having positive pressures at any one time is small enough so as not to cause the collar 76 to fully disengage from the subject's neck 50 (FIG. 4) or to otherwise cause a problem with the treatment of the subject's sleep apnea. For example, the controller 134 can be configured so that no more than one end pressure region (e.g., the top or the bottom pressure region) 200 has a reduced-magnitude negative pressure, or a positive pressure, at any one time.

Still referring to FIGS. 16-18, alternate embodiments of the collar 76, and of the system 70 (FIGS. 4-7) in general, are contemplated. For example, the collar segments 224 can have different sizes or shapes from one another and from what is described. Furthermore, there can be fewer or more than three segments 224. Moreover, the peristalsis action can propagate from top to bottom of the collar 76 instead of from bottom to top, can alternate propagation directions, and can be altered in any suitable manner.

FIG. 19 is a view of a portion 250 of the collar 76 of FIGS. 4-7 and 14, according to another embodiment.

FIG. 20 is a cross-sectional view of the collar portion 250 of FIG. 19 taken along a line A-A of FIG. 11, and of the portion 222 of the subject's neck 50 and airway 14, according to an embodiment.

Referring to FIGS. 19-20, the collar portion 250 is similar to the collar portion 220 of FIGS. 16-18 but for the addition of one or more sealing surfaces 252 that are each transverse to the sealing surfaces 94 away from the terminators 240, and the addition of a corresponding one or more pressure-region separators 254, which may be similar to the terminators 240 and which support the transverse sealing surfaces. The transverse sealing surfaces 252 can be similar to the sealing surfaces 94, and can be attached to the separators 254 in any suitable manner. And the separators 254 can be made from the same material as the frame portions 226 or the terminators 240, and can be attached to the vacuum surface 96 or to the frame portions in a manner similar to the manner in which the terminators can be attached to the vacuum surface or the frame portions as described above in conjunction with FIG. 18. Alternatively, the separators 254 can be formed integrally with the frame portions 226 in a manner similar to the manner in which the terminators 240 can be formed integrally with the frame portions 226 as described above in conjunction with FIG. 18.

The transverse sealing surfaces 252 and separators 254 form additional pressure regions 200 (FIGS. 16-18) by dividing the collar segments 224 into multiple sections.

Furthermore, if the sleep-apnea-treatment system 70 (FIGS. 4-7) regulates the pressures within the pressure regions 200 (FIGS. 16-18) in a manner that mimics peristalsis, the controller 134 (FIG. 8) can be configured to change the pressures within the pressure regions belonging to the same collar segment 224 simultaneously. Alternatively, the controller 134 can be configured to regulate the pressures within the pressure regions 200 in a manner similar to the peristalsis technique described above in conjunction with FIGS. 16-18, but in a circumferential direction (i.e., in a direction around the neck 50 instead of in a direction up or down the neck). Or, the controller 134 system can be configured to so regulate the pressures within the pressure regions 200 both in a transverse direction (i.e., up or down the neck) and in a circumferential direction.

Still referring to FIGS. 19-20, alternate embodiments of the collar 76, and of the system 70 (FIGS. 4-7) in general, are contemplated. For example, the same alternatives discussed above for the collar 76 of FIGS. 16-18 can be applicable to the collar 76 of FIGS. 19-20.

Figure 21:
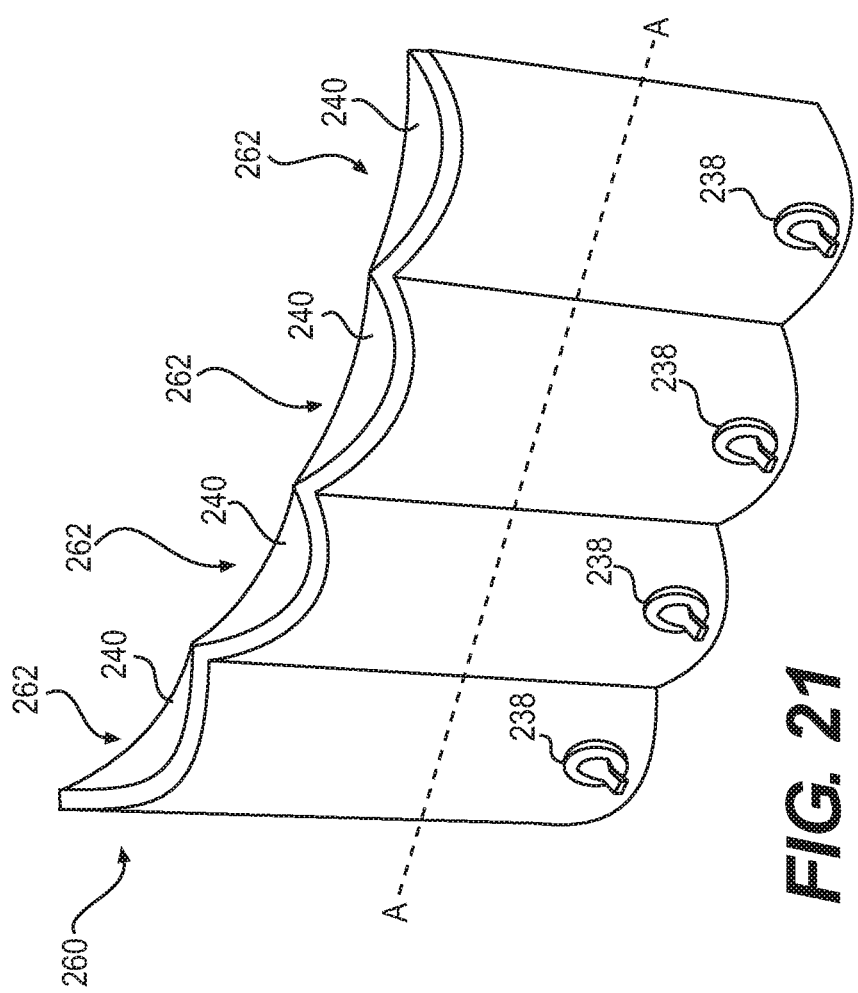
FIG. 21 is a diagram of a portion of a collar of FIGS. 4-7, according to yet another embodiment.

FIG. 21 is a view of a portion 260 of the collar 76 of FIGS. 4-7 and 14, according to yet another embodiment.

Figure 22:
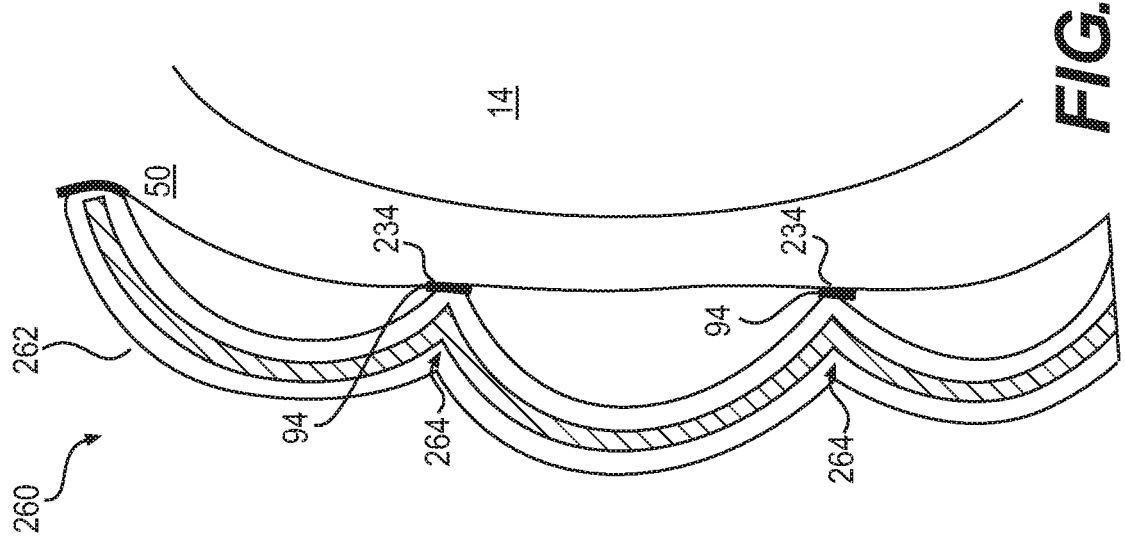
FIG. 22 is a view of the collar portion of FIG. 21 taken along line A-A of FIG. 21, according to an embodiment.

FIG. 22 is a cross-sectional view of the collar portion 260 of FIG. 21 taken along a line A-A of FIG. 21, and of the portion 222 of the subject's neck 50 and airway 14, according to an embodiment.

Referring to FIGS. 21-22, the collar portion 260 is similar to the collar portion 220 of FIGS. 16-18, except that collar segments 262 are configured to extend in a transverse direction (i.e., up/down the neck 50) while the subject 12 (FIG. 4) is wearing the sleep-apnea system 70, unlike the collar segments 224 (FIGS. 16-18), which are configured to extend in a circumferential direction (i.e., around the neck). And although not shown, the collar portion 260 may be similar to the collar portion 250 of FIGS. 19-20 in that it can include sealing surfaces and separators that are similar to the sealing surfaces 252 and the separators 254 and that are approximately transverse to (i.e., in approximately the same direction as the line A-A in FIG. 21) the sealing surfaces 92 and joints 264.

Still referring to FIGS. 21-22, alternate embodiments of the collar 76, and of the system 70 (FIGS. 4-7) in general, are contemplated. For example, the same alternatives discussed above in conjunction with FIGS. 16-20 can be applicable to the collar 76 of FIGS. 21-22.

Figure 23:
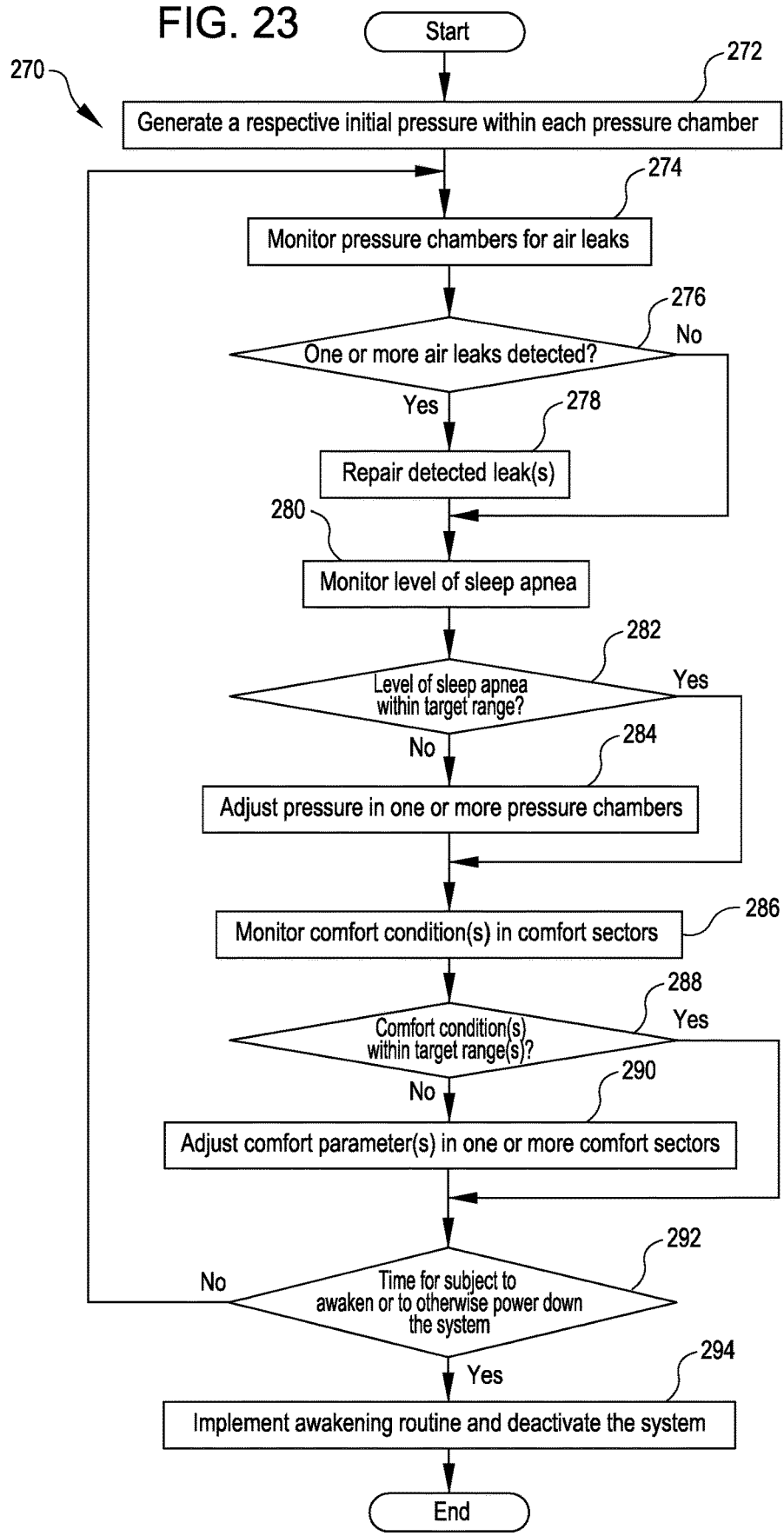
FIG. 23 is a flow diagram of the operation of the sleep-apnea-treatment system of FIGS. 4-7, according to an embodiment.

FIG. 23 is a flow diagram 270 of an operational mode of the sleep-apnea-treatment system 70 (FIGS. 4-7), according to an embodiment.

Referring to FIGS. 4-8, and 14-22, operation of the sleep-apnea-treatment system 70 (FIGS. 4-7) is described, according to an embodiment.

After the subject 12 puts on and activates the treatment system 70 (e.g., via the power-switch assembly 100), at a step 272 of the flow diagram 270, the controller 134 causes the pump assembly 118 and the pressure-regulator assembly 120 to generate a respective initial pressure, for example, a respective negative pressure, within each pressure region 200. That is, the pump assembly 118 generates the one or more negative pressures by drawing air from outside of the collar 76 into the inlet valves 238, through the inlet openings 202, into the one or more pressure regions 100, through the outlet openings 204, through the valve and pressure-regulator assemblies 120 and 122, into the pump assembly 118, and out through the outlet valve 102. Alternatively, one or more of the inlet valves 238 and inlet openings 202 can be inactivated or omitted such that the pump assembly generates at least some of the one or more negative pressures without generating respective sustained airflows.

Next, at a step 274 of the flow diagram 270, the controller 134 monitors the one or more pressure regions 200 for air leaks in response to one or more pressure indications from the pressure-sensor assembly 126.

At a step 276, the controller 134 determines whether there are any air leaks. If the controller 134 determines that there are no leaks, then the controller proceeds to a step 280. But if the controller 134 determines that there is at least one leak, then the controller proceeds to a step 278, At the step 278, the controller 134 causes the repair of each of the detected one or more leaks, for example, by causing the sealant-dispenser assembly 124 to dispense a sealant from the reservoir 146 via one or more of the sealant-dispensing openings 210 in the vicinity of the respective leak.

Then, at the step 280, the controller 134 monitors the degree of sleep apnea that the subject 12 is experiencing via the apnea-degree-sensor assembly 128. For example, the controller 134 can monitor the subject's respiratory rate.

Next, at a step 282, the controller 134 determines whether the degree of sleep apnea that the subject 12 is experiencing is within a target range. For example, the controller 134 may determine whether the subject's respiratory rate is within a target range. If the controller 134 determines that the degree of sleep apnea is within the target range, then the controller proceeds to a step 286. But if the controller 134 determines that the degree of sleep apnea is outside of the target range, then the controller proceeds to a step 284.

At the step 284, the controller 134 identifies one or more pressure regions 200 that the controller has determined are to be adjusted, and controls the pump assembly 118 or the pressure-regulator assembly 120 to adjust the pressure in the identified one or more pressure regions in an effort to drive the degree of sleep apnea toward the target range.

Then, at the step 286, the controller 134 monitors one or more comfort conditions in one or more comfort sectors of the system 70 (FIGS. 4-7). For example, the controller 134 can monitor temperature or pressure in one or more of the pressure regions 200.

Next, at a step 288, the controller 134 determines whether the one or more comfort conditions in one or more comfort sections are within respective target ranges. For example, the controller 134 can determine whether the temperature within each pressure region 200 is within a respective target range. If the controller 134 determines that each of the one or more comfort conditions is within its respective target range, then the controller proceeds to a step 292. But if the controller 134 determines that at least one of the one or more comfort conditions is outside of its respective target range, then the controller proceeds to a step 290.

At the step 290, the controller 134 identifies one or more comfort sectors that are to be adjusted, and controls the temperature-control assembly 132 to adjust one or more comfort parameters (e.g., temperature) in the identified one or more comfort sectors in an effort to drive the one or more comfort conditions toward their respective target ranges. In addition, or in the alternative, the controller 134 may control the pump assembly 118 and the pressure-regulator assembly 120 in a peristalsis manner so as to temporarily reduce the magnitude of the pressure within one or more pressure regions 200 to reduce the chances of an edema forming, or to otherwise give the respective regions 246 of the subject's neck 50 a "break" from the higher-magnitude pressures.

At the step 292, the controller 134 determines whether it is time for the subject 12 to awaken or to otherwise power down the system (e.g., because the subject has removed the system 70 and turned the system "off" via the power-switch assembly 100). If it is not time to awaken the subject 12, then the controller 134 returns to the step 274. But if it is time to awaken the subject 12, then the controller 134 proceeds to a step 294.

At the step 294, the controller 134 implements an awakening routine and then deactivates the system 70 (FIG. 4), or, alternatively, the controller skips an awakening routing and deactivates the system. As example of an awakening routine, the controller 134 can be programmed to help awaken the subject 12 at a specified time, or in response to increasing ambient light, by sounding an audible alarm and slowly reducing the magnitude of the respective pressure within each pressure region 200, or by varying the respective pressure within one or more pressure regions according to a sequence or pattern that gently awakens the subject.

After the step 294, the above-described operational mode ends, and is repeated the next time that the subject 12 activates the sleep-apnea-treatment system 70.

Additional embodiments of a negative-pressure sleep-apnea-treatment system are described below in conjunction with FIGS. 24-63. The sleep-apnea-treatment system 70 described above in conjunction with FIGS. 4-23 may be modified to include any one or more features of any embodiment of any sleep-apnea-treatment system described below in conjunction with FIGS. 24-63; likewise, the sleep-apnea-treatment systems described below in conjunction with FIGS. 24-63 may each be modified to include any one or more features of any embodiments of the sleep-apnea-treatment 70. Furthermore, the embodiments of the sleep-apnea-treatment systems described below in conjunction with FIGS. 24-63 may be structurally and operationally configured the same as one or more of the embodiments of the sleep-apnea-treatment system 70 unless otherwise noted.

Figure 24:
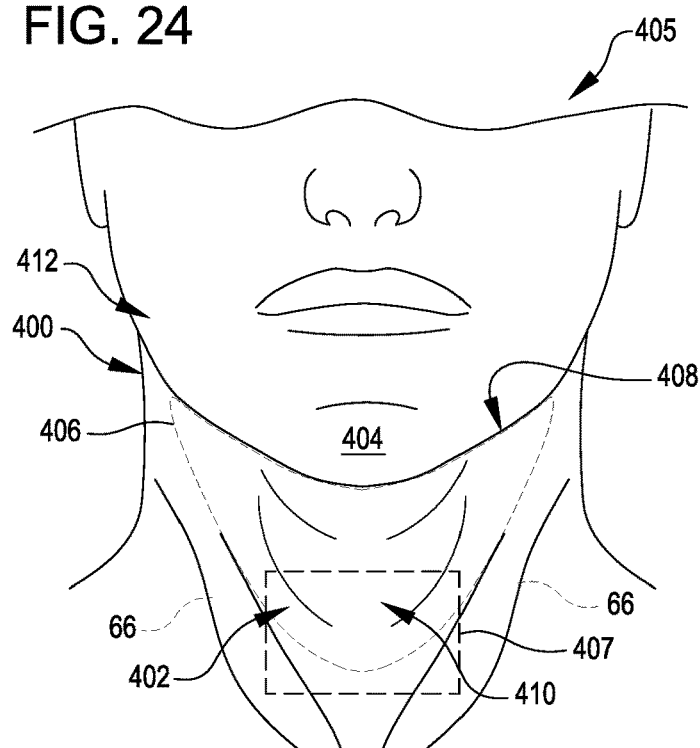
FIG. 24 is a front view of a neck of a subject, of a throat region of the neck, and of a region of the throat for applying a negative pressure for the treatment of sleep apnea, according to an embodiment.
Figure 25:
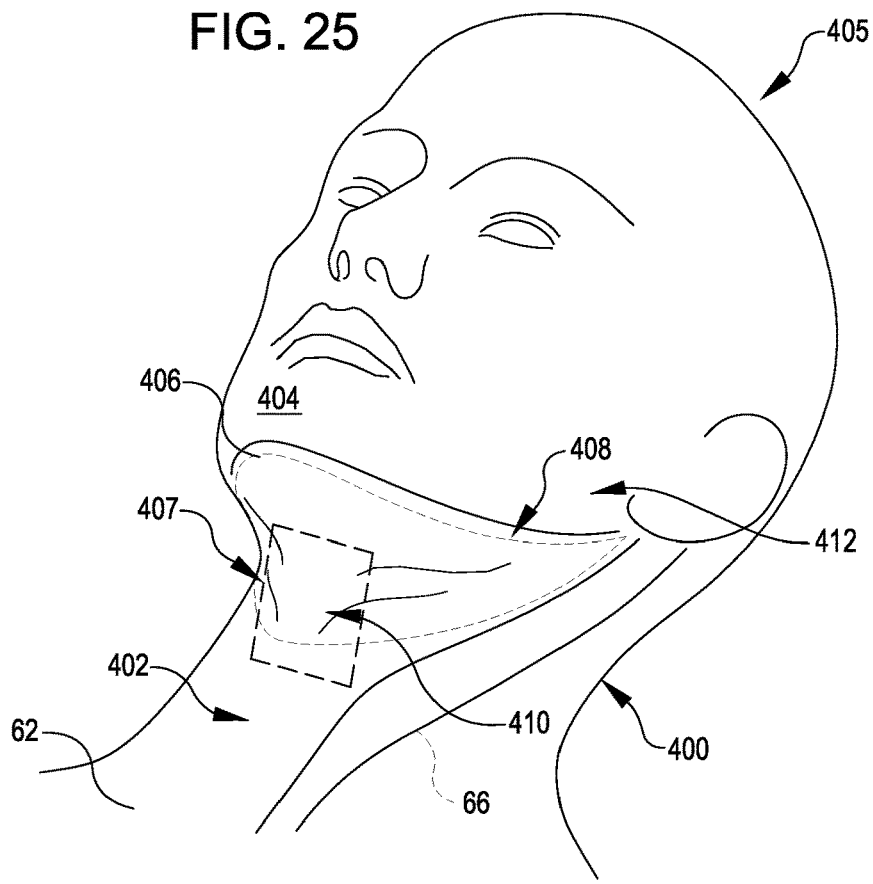
FIG. 25 is a side view of the neck, throat region, and negative-pressure-application region of FIG. 24, according to an embodiment.

FIGS. 24-25 are an isometric front view, and an isometric side view, respectively, of a neck 400, throat 402, and chin 404, of a subject 405, and of throat areas 406 and 407 for applying a negative pressure to treat sleep apnea, such as obstructive sleep apnea, according to an embodiment.

Referring to FIGS. 3 and 24-25, in an embodiment, the negative-pressure-application area 406 is bounded on the bottom by the subject's sternal head 62, on the sides by the subject's sternocleidomastoid muscles 66, and on the top by the intersection 408 (i.e., the anterior belly of Digastricus 55 in FIG. 3) of the subject's chin 404 with the subject's throat 402. In another embodiment, which is illustrated in FIGS. 24-25, the negative-pressure-application area 406 is bounded on the bottom by the subject's Adam's apple 410 (thyroid cartilage 57 in FIG. 3), on the sides by the subject's sternocleidomastoid muscles 66, and on the top by the intersection 408 of the subject's chin 404 with the subject's throat 402.

The negative-pressure-application area 407 is typically smaller than the area 406, can be partially or fully within the area 406, and can be a rectangle or square about the subject's Adam's apple 410. For example, the side boundaries of the area 407 can be aligned with the respective corners of the subject's mouth, and the top boundary of the area 407 can be just under the subject's chin 404. In an embodiment, the negative pressure application is sufficient to move the subject's tongue and/or other soft palate tissue anteriorly, thereby reducing or eliminating airway obstruction. In an embodiment, the negative pressure application is sufficient to move the subject's tongue and/or other soft palate tissue anteriorly, thereby reducing or eliminating snoring without airway obstruction.

As discussed above, a negative pressure (e.g., a suction) applied to the area 406 or to the area 407 can cause movement of tissue obstructing the subject's airway (airway 14 of FIG. 1) sufficient to reduce or remove the obstruction. The negative pressure can "pull out" tissue within the area 406 or area 407, which tissue, by virtue of being connected to the obstructing tissue or to other tissue adjacent to the subject's airway, can "pull" the obstructing tissue or other tissue adjacent to the subject's airway a distance sufficient to reduce or remove the obstruction. Alternatively, the negative pressure can cause the subject's jaw 412 to move (e.g., forward, down, or both forward and down) sufficiently to reduce or remove the obstruction. Or, the negative pressure can reduce or remove the airway obstruction by both "pulling out" tissue within the area 406 or 407 and by causing the jaw 412 to move.

Referring to FIGS. 24-25, other embodiments of the negative-pressure-application areas 406 and 407 are contemplated. For example, each of the above-described boundaries of the area 406 or the area 407 can be altered by any distance within a distance range of, e.g., ±25 millimeters (mm).

Figure 26:
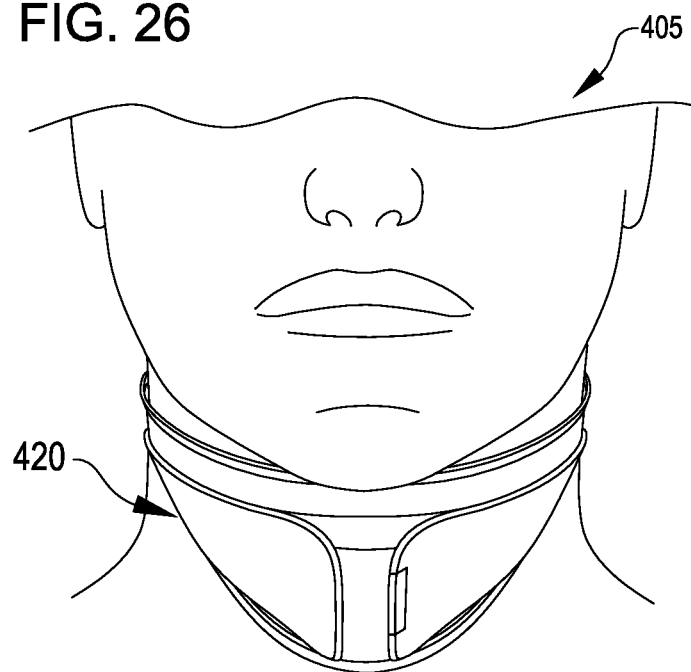
FIG. 26 is a front view of a subject wearing a system designed to treat sleep apnea by applying a negative pressure to the negative-pressure-application region of FIGS. 24-25, according to an embodiment.

FIG. 26 is an isometric front view of a subject 405 wearing a negative-pressure sleep-apnea-treatment system 420, according to an embodiment. The system 420 is designed to apply negative pressure to the throat area 406, the throat area 407, or both the throat areas 406 and 407, of the subject as described above in conjunction with FIGS. 24-25. In addition to the structural and operational features described below in conjunction with FIGS. 26-63, the system 420 can have any of the structural and operational features of any embodiment of the sleep-apnea-treatment system 70 described above in conjunction with FIGS. 4-23.

The sleep-apnea-treatment system 420 can be self-contained such that it requires no connection to an external device (e.g., a base station, a power outlet) to operate, and therefore, can be more comfortable than a conventional CPAP machine or other sleep-apnea-treatment system that includes, e.g., a base station and an air hose coupled between the base station and the system. For example, a self-contained version of the sleep-apnea system 420 can include a battery (e.g., the battery 110) that is rechargeable while the subject 405 is not wearing/using the sleep-apnea system such that the sleep-apnea system needs no physical connection (e.g., no power cord, no hose, and no wired communication link) to another device or location while the subject is wearing, or otherwise using, the sleep-apnea system. But a self-contained version of the sleep-apnea system 420 can be configured to include a wireless communication link and a wireless power link.

Figure 27:
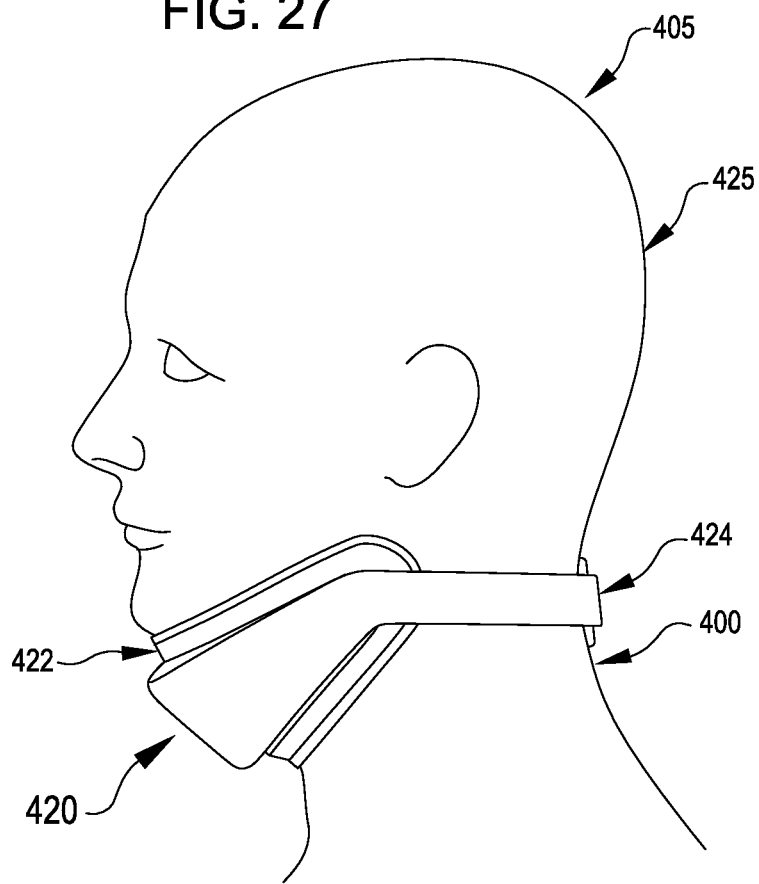
FIGS. 27-28 are respective side views of a subject wearing the sleep-apnea-treatment system of FIG. 26, according to an embodiment.
Figure 28:
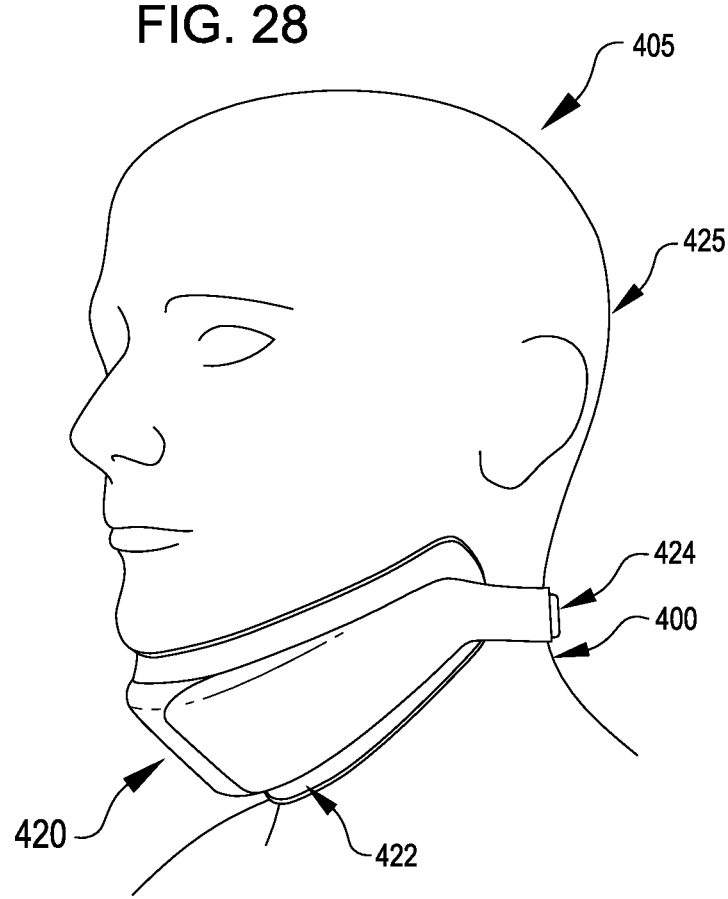

FIGS. 27-28 are respective isometric side views of the subject 405 wearing the negative-pressure sleep-apnea-treatment system 420 of FIG. 26, according to an embodiment. The sleep-apnea system 420 includes a removable gasket assembly 422, which is configured to form an airtight seal around the perimeter of the sleep-apnea system, and which includes a removable strap assembly 424, which is configured to secure the sleep-apnea system around the neck 400 of the subject 405. Alternatively, the strap assembly 424 can be configured to secure the sleep-apnea system 420 to, or around, a head 425 of the subject 405.

Figure 29:
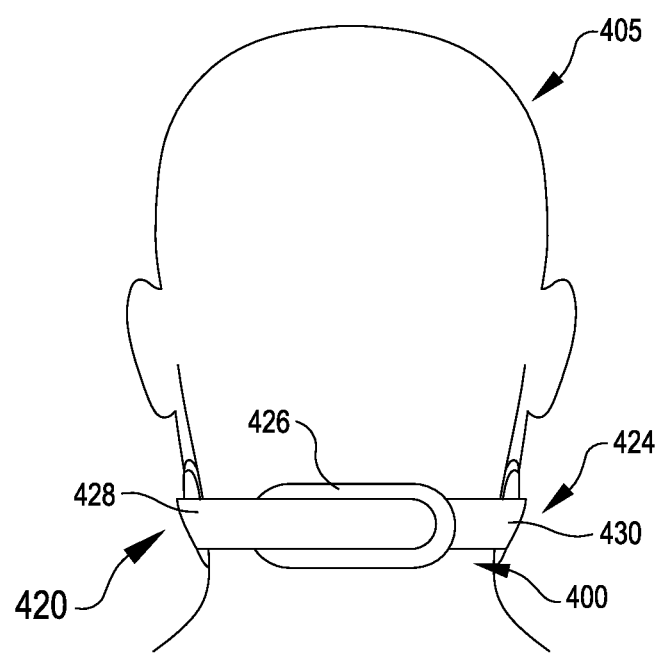
FIG. 29 is a rear view of a subject wearing the sleep-apnea-treatment system of FIGS. 26-28, according to an embodiment.

FIG. 29 is an isometric rear view of the subject 405 wearing the negative-pressure sleep-apnea-treatment system 420 of FIGS. 26-28, according to an embodiment. The strap assembly 424 can include a coupler 426, which is configured to couple together rear ends of straps 428 and 430 of the strap assembly at the back of the subject's neck 400. The coupler 426 is also configured to allow adjustment of the size of the neck loop formed by the straps 428 and 430 of the strap assembly 424. That is, one can use the coupler 426 to adjust the loop size such that the fit of the sleep-apnea system 420 is not so "tight" that it causes the subject 405 discomfort, and is not so "loose" that it allows an air leak where the gasket assembly 422 contacts the neck 400 of the subject. The coupler 426 and ends of the straps 428 and 430 can include Velcro® or any other suitable material or structure that allows adjustably coupling together the straps. Alternatively, the coupler 426 can be omitted from the sleep-apnea system 420, and one can couple the strap ends, which can include Velcro®, directly to one another.

Figure 30:
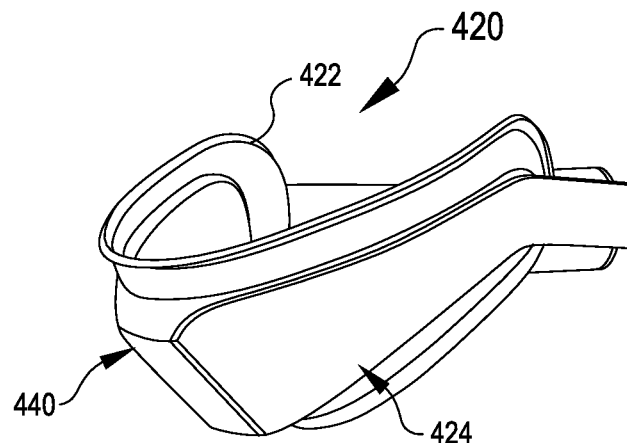
FIG. 30 is an isometric side view of the sleep-apnea-treatment system of FIGS. 26-29, according to an embodiment.

FIG. 30 is an isometric side view of the negative-pressure sleep-apnea-treatment system 420 of FIGS. 26-29, according to an embodiment.

Figure 31:
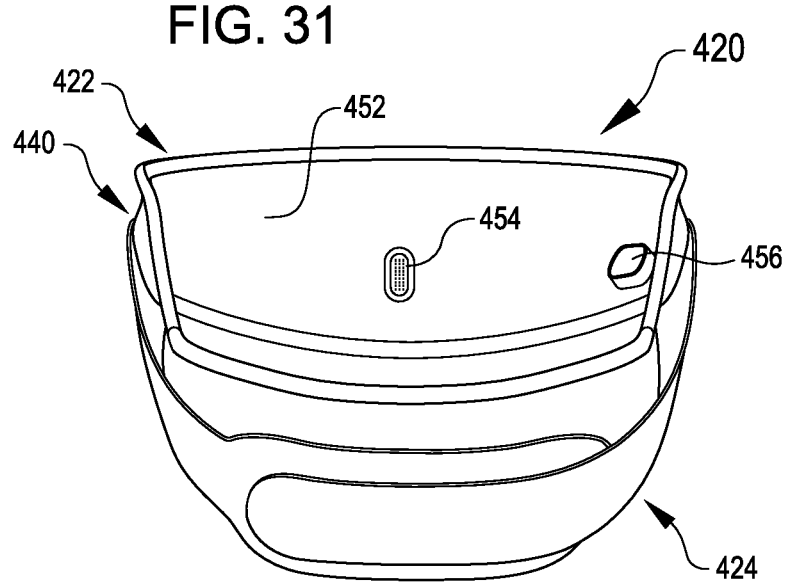
FIG. 31 is an isometric rear view of the sleep-apnea-treatment system of FIGS. 26-30, according to an embodiment.

FIG. 31 is an isometric rear view of the negative-pressure sleep-apnea-treatment system 420 of FIGS. 26-30, according to an embodiment.

Figure 32:
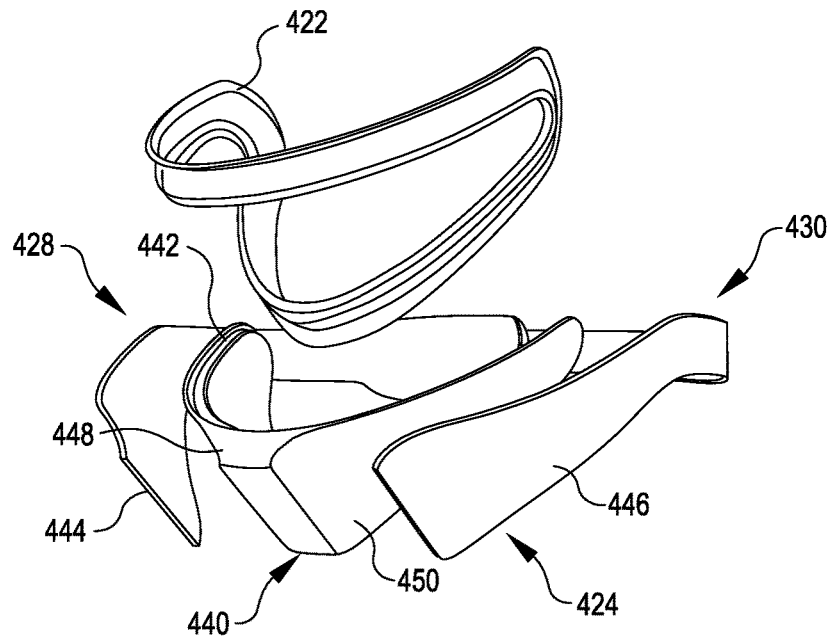
FIG. 32 is an exploded view of the sleep-apnea-treatment system of FIGS. 26-31, according to an embodiment.

FIG. 32 is an isometric exploded view of the negative-pressure sleep-apnea-treatment system 420 of FIGS. 26-31, according to an embodiment.

Referring to FIGS. 30-32, in addition to the gasket assembly 422 and the strap assembly 424, the negative-pressure sleep-apnea-treatment system 420 includes a collar assembly (hereinafter "collar") 440.

The gasket assembly 422 is configured to be removably attachable to the collar 440, e.g., by "snapping" onto a perimeter 442 of the collar. In an embodiment of the sleep-apnea system 420, it is anticipated that the gasket assembly 422 will wear out, be upgraded, or will otherwise require repair or replacement more frequently than the collar 440; therefore, configuring the gasket assembly to be removable can allow replacement of the gasket assembly independently of the collar.

The strap assembly 424 also is configured to be removably attachable to the collar 440, e.g., by attaching to the sides of the collar. The straps 428 and 430 of the strap assembly 424 have respective front ends 444 and 446, which are configured for removable attachment to respective side portions 448 and 450 of the collar 440. For example, the strap front end 444 and the collar side portion 448 can include oppositely structured Velcro® pieces, as can the strap front end 446 and the collar side portion 450. Furthermore, the positions of the strap front ends 444 and 446 can be adjustable relative to the collar side portions 448 and 450 to allow one to adjust the size of the neck loop formed by the straps 428 and 430 of the strap assembly 424. Moreover, in an embodiment of the sleep-apnea system 420, it is anticipated that the strap assembly 424 will wear out, be upgraded, or will otherwise require repair or replacement more frequently than the collar 440; therefore, configuring the strap assembly to be removable can allow replacement of the strap assembly independently of the collar 440.

Referring to FIG. 31, the collar 440 includes a rear side 452 (the side configured to faces the subject's neck 400 (e.g., FIGS. 26-29 when the sleep-apnea system 420 is worn), on, or through, which are disposed one or more outlet openings 454 (only one opening shown in FIG. 31) and one or more sensors 456 (only one sensor shown in FIG. 31). For example, the one or more outlet openings 454 can be structurally and functionally similar to the outlet openings 204 of FIG. 14, and the one or more sensors 456 can be structurally and functionally similar to the sensors of the sensor assemblies 126 and 128 of FIG. 8. As described above in conjunction with FIGS. 4-23, and as described below, a pump (not shown in FIG. 31) draws air through the one or more outlet openings 454 to create a volume, or region, of negative pressure between the rear side 452 of the collar 440 and the subject's throat area 406 or throat area 407 (FIGS. 24-25).

Drawing air through the one or more outlet opening 454 can also be referred to as drawing a vacuum, or drawing a partial vacuum, via the one or more outlet openings, and the volume or region of negative pressure can be called a vacuum, a partial-vacuum, or a pressure region, and can be structurally and functional similar to the pressure region 200 described above in conjunction with, e.g., FIG. 17. Further as described above in conjunction with FIGS. 4-24, and as described below, the one or more sensors 456 can be configured to sense and to provide information, or to sense and to provide one or more physical parameters from which the sleep-apnea system 420 can derive information, that the sleep-apnea system can use to adjust the magnitude of the negative pressure, or to adjust other parameters (e.g., neck temperature), so as to open, or maintain open, an airway of the subject (e.g., the airway 14 of FIG. 1). Moreover, the one or more sensors 456 can be configured to sense and to provide other information, or to sense and to provide one or more physical parameters from which the sleep-apnea system 420 can derive other information. For example, as described above in conjunction with FIG. 8 and below, the one or more sensors 456 can be configured to sense and to provide information related to a physical, a mental, an emotional, a health, or a wellbeing condition or state of the subject 405 (e.g., FIGS. 26-29), or information related to a subject's use, or the settings, of the sleep-apnea system 420. In addition, the one or more outlet openings 454 and the one or more sensors 456 can have any suitable positions, shapes, and sizes, which positions, shapes, and sizes can be different than as shown in FIGS. 30-32.

Still referring to FIGS. 30-32, the collar 440 can be custom manufactured to better fit the neck 400 of the subject 405 (e.g., FIG. 29). For example, a doctor or other person can use a conventional image-capture device or a conventional scanner to generate a three-dimensional (3D) image or map of the subject's neck 400 (at least the front and sides of the subject's neck). The 3D image or map can then be converted to a print file having a format suitable for a 3D printer, which can "print" the collar 440. Or the collar 440 can be manufactured by a CNC or other machine from the 3D image or map. Other components (e.g., the gasket assembly 422, the strap assembly 424) of the sleep-apnea system 420 can be manufactured in a similar manner.

Figure 33:
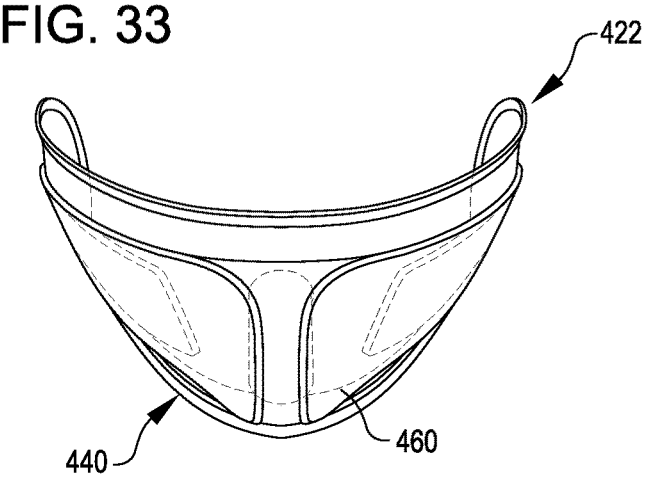
FIG. 33 is an isometric front view of the collar assembly of the sleep-apnea-treatment system of FIGS. 26-32 with transparent portions, according to an embodiment.

FIG. 33 is an isometric front view of the gasket assembly 422 and of the collar 440 of FIGS. 26-32, according to an embodiment.

Figure 34:
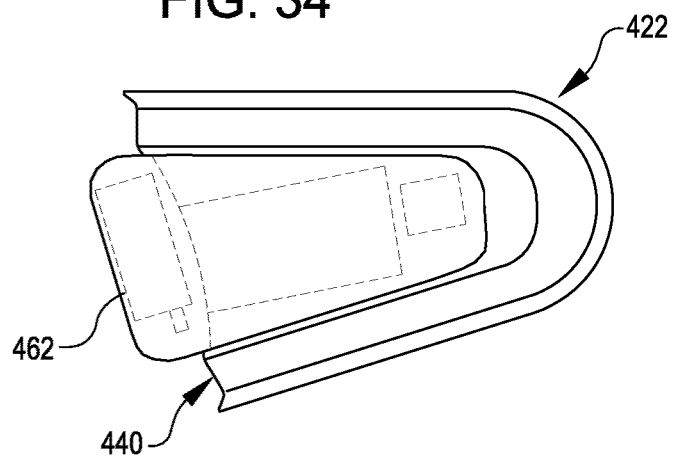
FIG. 34 is an isometric side view of the collar assembly of the sleep-apnea-treatment system of FIGS. 26-33 with transparent portions, according to an embodiment.

FIG. 34 is an isometric side view of the gasket assembly 422 and of the collar 440 of FIGS. 26-33, according to an embodiment.

Figure 35:
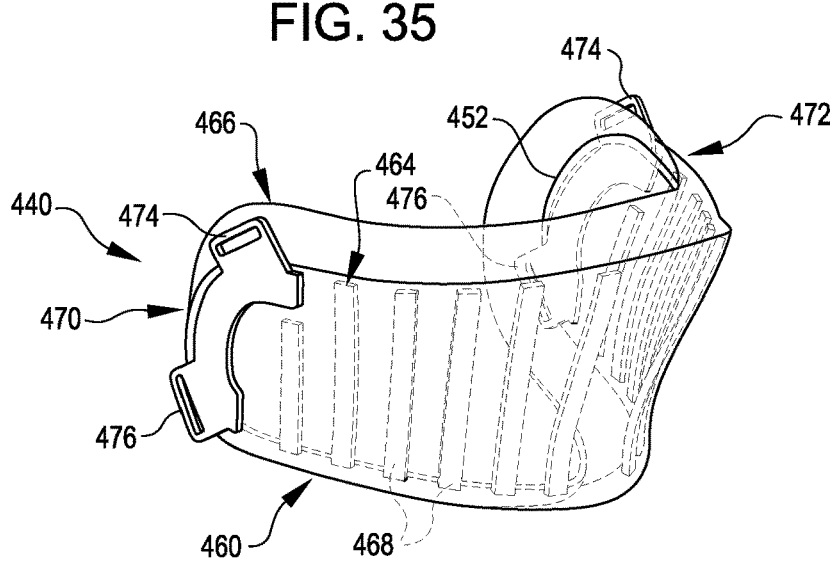
FIG. 35 is an isometric transparent side view of the collar assembly of FIGS. 26-34, according to an embodiment.

FIG. 35 is an isometric side isometric view of the collar 440 of FIGS. 26-34 with transparent portions, according to an embodiment.

Referring to FIGS. 33-35, the collar 440 includes a semi-rigid housing 460, and includes a compartment 462, which is formed in the front of the housing and which is configured for holding one or more components of the sleep-apnea system 420.

Referring to FIG. 35, the collar housing 460 includes a rigid internal frame 464 disposed in a flexible, elastomeric, overmold or package 466.

The frame 464 includes slats 468, and can be formed from a plastic metal, or any other material with strength and rigidity sufficient to allow the collar 440 to form a region of negative pressure between the rear surface 452 of the collar and the neck 400 of the subject 405 (e.g., FIGS. 26-29) without the rear surface "collapsing" against the neck. Although shown as being oriented in a vertical dimension, one or more of the slats 468 can be oriented in a horizontal dimension or in a diagonal dimension, and the vertical slats can be coupled together by horizontal or diagonal cross slats (not shown in FIG. 35). Furthermore, the frame 464 can include optional strap-attachment sections 470 and 472 for engaging the strap assembly 424 (e.g., FIG. 32), where the attachment sections can replace, or otherwise render unnecessary, the Velcro® strap-attachment sections 444, 446, 448, and 450 described above in conjunction with FIGS. 30-32.

Although each strap-attachment section 470 and 472 is shown as including two strap eyelets 474 and 476, one or both of the strap-attachment sections can include fewer than two, or more than two, strap eyelets.

The overmold 466 can be formed from a plastic metal, or from any other suitable material with strength and rigidity sufficient to allow the collar 440 to form a region of negative pressure between the rear surface 452 of the collar and the throat area 406 or the throat area 407 (FIGS. 24-25) of the subject 405 (e.g., FIGS. 27-28) without the rear surface "collapsing" against the throat, yet with sufficient flexibility and surface texture to allow the collar to comfortably fit against, and to conform to the shape of, the subject's neck 400 (e.g., FIGS. 27-28). If the collar 440 is configured to form a region of negative pressure between the rear surface 452 of the collar and the throat area 407, then the collar 440 can be smaller, or, for a given size, can have more room for components such as the components of the component module 550, than if the collar is configured to form the region of negative pressure between the rear surface of the collar and the throat area 406.

To form the housing 460, one first can form the frame 464 by conventional injection molding, and then can form the overmold 466 over the frame also by conventional injection molding.

Referring again to FIGS. 33-35, the compartment 462 can be formed as a compartment integral to the overmold 466, or can be formed as part of the frame 464 for additional strength. Furthermore, the compartment 462 can include an access panel (not shown in FIGS. 33-35) in the rear (the side facing the subject 105) of the collar 440, or in the front (the side facing away from the subject) of the collar, to allow repair or replacement of components within the compartment. Alternatively, the compartment 462 can include no access panel such that that the components are sealed within the compartment and cannot be repaired or replaced without dismantling or destroying (e.g., by cutting through the overmold 466) the collar 440. And examples of components that can be disposed within the compartment 462 include batteries, motors, pumps, valves, sensors, electronic circuitry and electronic components, and mechanical assemblies and mechanical components (further examples of such components are described above in conjunction with, e.g., FIG. 8, and below in conjunction with, e.g., FIG. 45.

Figure 36:
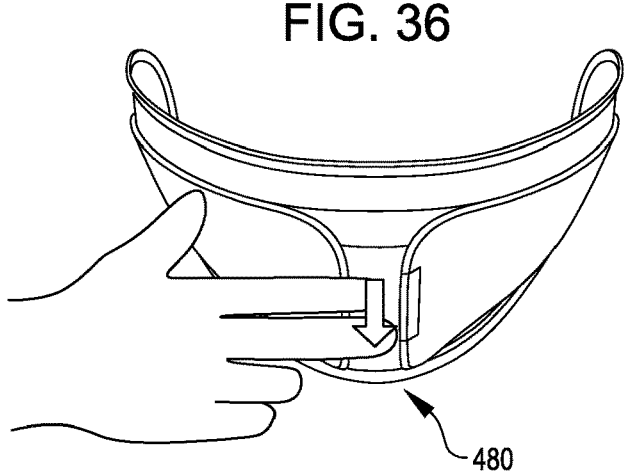
FIG. 36 is an isometric front view of the collar assembly of FIGS. 26-35 including a tactile on/off switch, according to an embodiment.

FIG. 36 is an isometric front view of the collar 440 of FIGS. 26-35, and of an on/off switch 480 for the negative-pressure sleep-apnea-treatment system 420, according to an embodiment. The switch 480 can be a tactile-type slide switch located, for example, on the front side of the component compartment 462. That is, one can toggle the switch 480 between its "on" and "off" states by swiping a finger across the front side of the compartment 462, much like how one can toggle a switch displayed on a smart phone's screen. For example, the collar 440 can include a display screen, a capacitance sensor, or other device exposed through, or located just behind, the front side of the compartment 462, where the switch 480 is formed, or otherwise implemented, by the device. In its "on" state, the switch 480 is configured to activate the sleep-apnea system 420 by connecting the components of the system (e.g., motors and other components within the compartment 462, and the sensor 456 of FIG. 31) to a power source, such as a battery, disposed within the compartment; and in its "off" state, the switch is configured to deactivate the sleep-apnea system by disconnecting the components of the sleep-apnea system from the power source. The switch 480 is further configured such that it is difficult to impossible for the subject 405 (e.g., FIG. 29) to inadvertently toggle the switch to its "off" state while the subject is sleeping and wearing the sleep-apnea system 420. For example, the switch 480 can be configured such that it would be difficult or impossible for bedding to become entangled with the switch and to toggle the switch to its "off" state due to movement of the subject 405 (e.g., the subject rolling over to sleep on his/her stomach, or moving while sleeping on his/her stomach). Furthermore, although shown as being located on the front side of the compartment 462, the switch 480 can be disposed at any other suitable location in or on the collar 440. Moreover, the switch 480 can be configured for control by a controller (e.g., the controller 134 of FIGS. 8 and 45) of the sleep-apnea system 420. For example, the controller can be configured to toggle, automatically, the switch 480 to its "off" state in response to detecting that the subject 405 removed the sleep-apnea system 420 from around his/her neck 400, and to toggle, automatically, the switch to its "on" state in response to detecting that the switch toggled to its "off" state while the subject is still sleeping.

Figure 37:
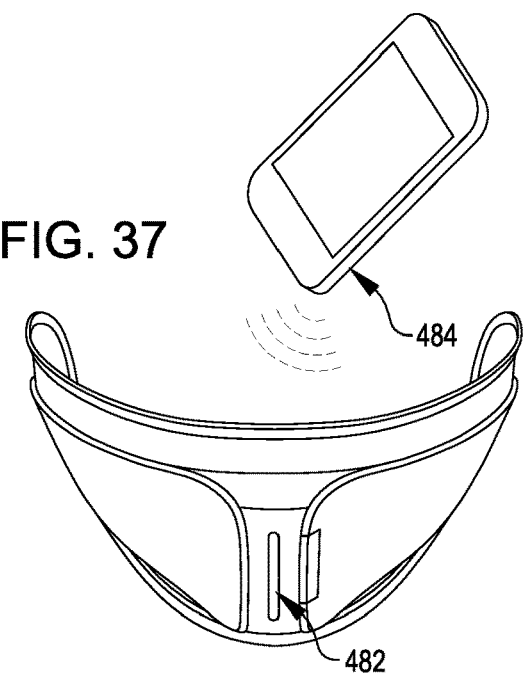
FIG. 37 is an isometric front view of the collar assembly of FIGS. 26-35 including having a light-emitting-diode (LED) battery-level indicator, and of a device for remote control of the collar assembly, according to an embodiment.

FIG. 37 is an isometric front view of the collar 440 of FIGS. 26-36, of a battery-level indicator 482, and of a remote-control device 484, according to an embodiment.

The battery-level indicator 482 can be any suitable type of indicator, such as a Light-Emitting-Diode (LED) display, configured to change color, intensity, or both color and intensity, to indicate a charge state of one or more of the batteries 110 (FIGS. 8 and 45), which power the sleep-apnea-treatment system 420. The indicator 482 can be located, for example, on the front side of the component compartment 462, or at any other suitable location of the collar 440. In response to the indicator 482 indicating that the one or more batteries 110 have low charge states, one can charge the battery, e.g., with an AC adapter, as described above in conjunction with FIG. 5.

The remote-control device 484 can be configured to control the operation of the sleep-apnea-treatment system 420, can be any suitable device, such as a dedicated remote-control device or a smart phone, and can be configured to communicate with the sleep-apnea system according to any suitable wireless or wired protocol such as Bluetooth®, WiFi®, Zigbee®, Radio Frequency (RF), or infrared (IR). For example, the remote-control device 484 can be configured to allow one to adjust the settings (e.g., magnitude of the negative pressure, wake-up time) of the sleep-apnea-treatment system 420, to enter data into, or to retrieve data from, the memory 130 (FIGS. 8 and 45) of the sleep-apnea system, and to turn "on" or "off" the sleep-apnea treatment system. The remote-control device 484 also can be configurable and reconfigurable by, e.g., firmware or software. For example, if the remote-control device 484 is a smart phone, then one may be able to download, into the smart phone's memory, a software application that allows one to use the smart phone to control the sleep-apnea-treatment system 420. In addition to the remote-control device 484, or as an alternative to the remote-control device, the collar 440 can include the input device 98 (FIGS. 8 and 45), which can be, for example, a keypad or a display screen, and which can be configured to allow one to control, to input data into the memory 130 of, or to retrieve data from the memory of, the sleep-apnea-treatment system 420. Furthermore, the remote-control device 484 can be part of, or separate and distinct from, the sleep-apnea-treatment system 420 (e.g., FIGS. 26-32).

Figure 38:
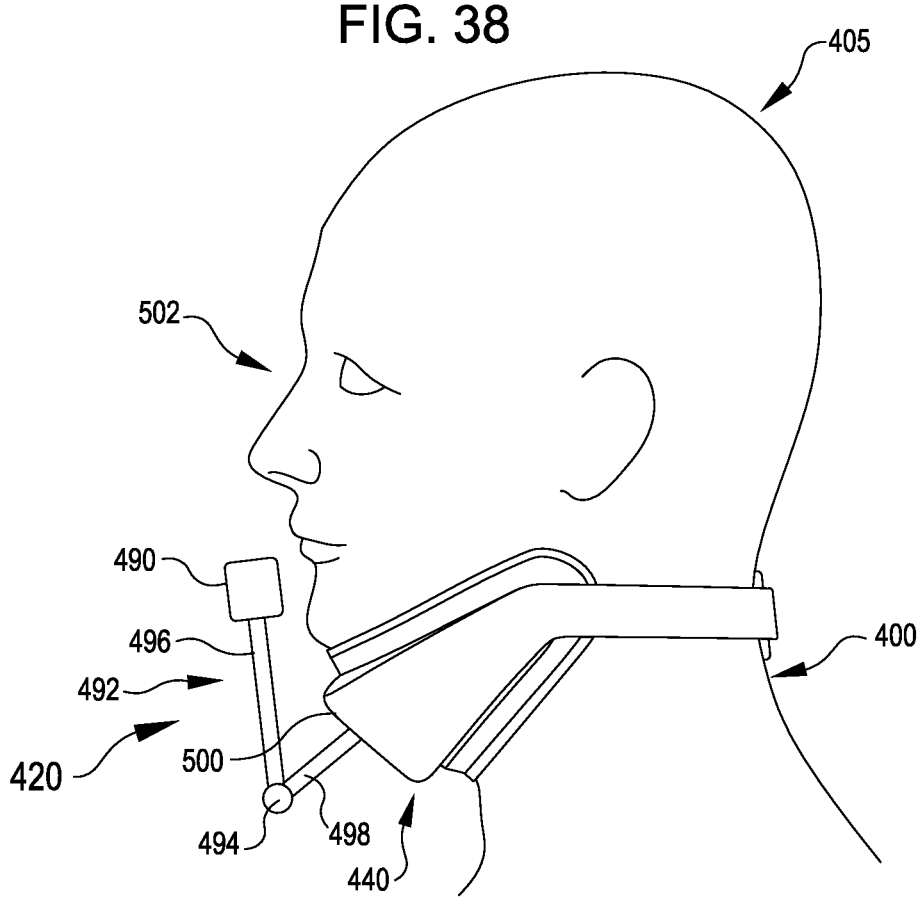
FIG. 38 is an isometric side view of a subject wearing the sleep-apnea-treatment system of FIGS. 26-32 including a position-adjustable sensor, according to an embodiment.

FIG. 38 is an isometric side view of the subject 405 wearing the negative-pressure sleep-apnea-treatment system 420 of FIGS. 26-32, according to an embodiment in which the system includes one or more sensors 490, which are located other than on a rear side 452 of the collar 440 as are the one or more sensors 456 of FIG. 31.

Figure 45:
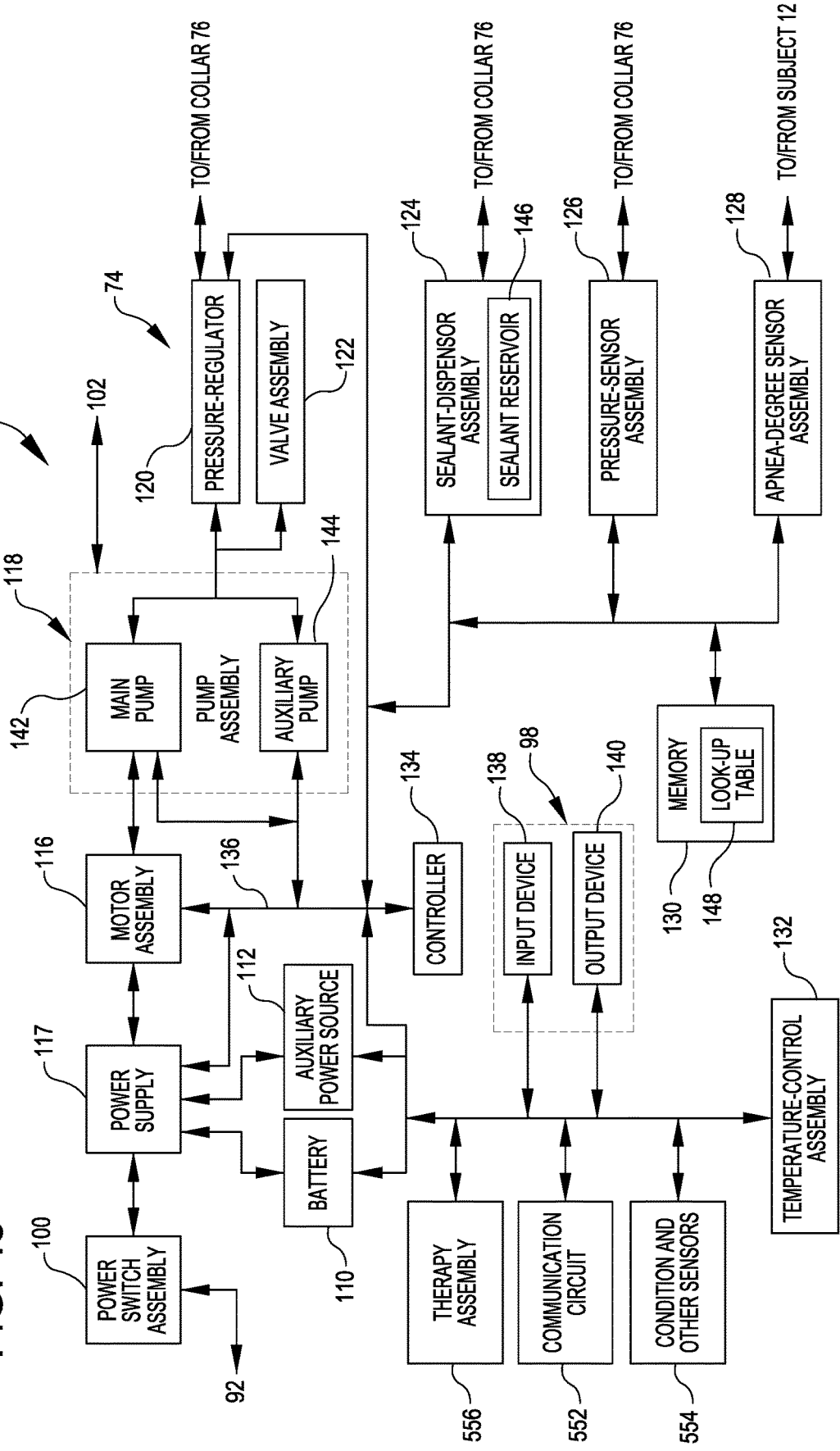
FIG. 45 is a block diagram of a component module of the sleep-apnea-treatment system of FIGS. 26-32, 42, and 44, according to an embodiment.

The one or more sensors 490 are mounted to an adjustable arm 492, which is attached to, or integral with, the collar 440, and which can be made from any suitable material such as metal or plastic. For example, the arm 492 can include a joint 494 about which one can rotate an upper section 496 of the arm in a plane parallel to a plane in which a lower section 498 of the arm lies. Furthermore, the arm 492 can include another joint 500 disposed between the collar 440 and the lower-arm section 498 and about which one can rotate or swivel the lower-arm section. Moreover, one or both of the upper-arm and lower-arm sections 496 and 498 can be extendible or retractable, e.g., by telescoping. In addition, the sleep-apnea system 420 can include one or more motors to change the position of the one or more sensors 490 under the control of the controller 134 (FIGS. 8 and 45). Furthermore, the arm 492 can be structurally and functionally configured in any other suitable manner. Moreover, although shown mounted to the end of the arm 492, the one or more sensors 490 can be mounted to any other part of the arm.

The one or more sensors 490 can include any suitable types of sensors that are configured to sense respective physical quantities and to generate respective analog or digital electronic signals that represent respective parameters (e.g., magnitude, phase, frequency) of the corresponding quantities. For example, the one or more sensors 490 can include one or more gas sensors configured to sense one or more substances in the air exhaled by (e.g., the exhalant of) the subject 405, or to sense a difference in levels of one or more substances in the ambient air and the levels of the same one or more substances in the subject's exhalant. Or, the one or more sensors 490 can include one or more sound sensors, such as microphones, configured to sense one or more sounds (e.g., snoring) made by the subject 405. Alternatively, the one or more sensors 490 can include one or more cameras, or other vision sensors, configured to sense whether the subject 405 is awake or asleep by sensing whether the subject's eyes 502 are opened or closed. Furthermore, the one or more sensors 490 can include one or more accelerometers or gyroscopes (e.g., microelectromechanical (MEMS) accelerometers or gyroscopes) to sense motion of the subject 405 or to sense the force at which the subject exhales air.

Figure 39:
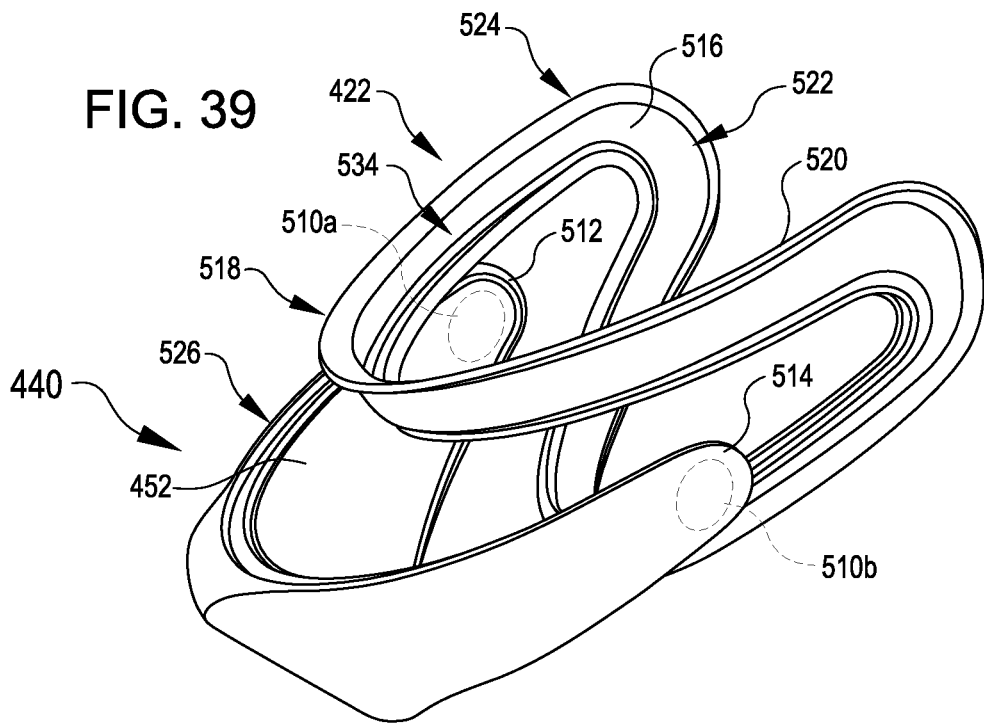
FIG. 39 is an isometric exploded view of the collar assembly and the gasket assembly of the sleep-apnea-treatment system of FIGS. 26-32, according to an embodiment.

FIG. 39 is an isometric exploded view of the gasket assembly 422 and of the collar 440 of the negative-pressure sleep-apnea-treatment system 420 of FIGS. 26-32 and 38, according to an embodiment in which the sleep-apnea system includes one or more electrodes 510 located at any suitable position(s) of the collar, such as on the rear side 452 of the collar at collar ends 512 and 514.

Figure 40:
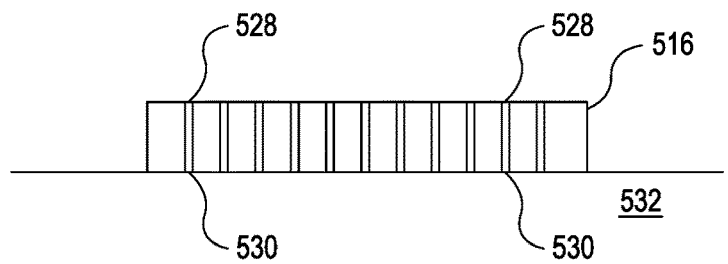
FIG. 40 is a cut-away side view of the gasket of the gasket assembly of FIG. 29, according to an embodiment.

FIG. 40 is a cutaway side view of a gasket 516 of the gasket assembly 422 of FIGS. 26-34 and 39, according to an embodiment.

Referring to FIGS. 39-40, a front 518 of the gasket assembly 422 includes an engagement portion (e.g., a "lip") 520, and a rear 522 of the gasket assembly includes the gasket 516.

The engagement portion 520 of the gasket assembly 422 is disposed about a perimeter 524 of the gasket assembly 422 and is configured to removably engage a rim 526 disposed about the perimeter 442 of the collar 440. For example, the engagement portion 520 can engage the rim 526 by "snapping" onto the rim, and can disengage the rim by "snapping" off of the rim. Alternatively, the engagement portion 520 can attach to the rim 526 with an adhesive (not shown in FIGS. 39-40), or with pins (not shown in FIGS. 39-40) that are disposed on the engagement portion and that "snap" into and out of receptacles (not shown in FIGS. 39-40) disposed in the rim. Furthermore, the engagement portion 520 can be formed from any suitable material that is flexible and elastomeric enough to flex with the collar 440 and, e.g., to allow "snapping" of the engagement portion onto and off from the collar rim 526.

The gasket 522 is configured to form an airtight seal with the neck 400 of the subject 405 (e.g., FIG. 38) wearing the sleep-apnea-treatment system 420 of FIGS. 26-32 and 38. The gasket 522 can be mounted to the front 518 of the gasket assembly 422, e.g., by adhesive, such that the gasket is removable/replaceable independently of the front of the gasket assembly; or, the gasket can be permanently attached to, or integral with, the front of the gasket assembly. Furthermore, the gasket 522 can be formed from any material suitable for forming an airtight seal with the subject's neck 400; examples of such material include foam, foam rubber, rubber, and a gel. Moreover, referring to FIG. 40, the gasket 522 can include channels 528, which have openings 530 configured to be contiguous with skin 532 of the subject's neck 400 such that when a vacuum is pulled through the channels, the gasket is pulled or "sucked" against the skin to form a tighter seal than may be obtainable with only the strap assembly 424 (e.g., FIG. 32). For example, the channels 528 can include openings (not shown in FIGS. 39-40) on an interior-facing side 534 of the gasket-assembly front 516 such that the vacuum pulled through the one or more outlet openings 454 (FIG. 31) to create a negative-pressure region between the collar 440 and a subject's neck 400 is also pulled through the channels 528. Alternatively, the collar rim 526, and also the gasket-assembly front 516, can include one or more vacuum channels (not shown in FIGS. 39-40) that are configured to allow a pump that generates the negative-pressure region to communicate with the channels 528 independently of the negative-pressure region. In addition, one can enhance the seal formed by the gasket 522 by applying a sealant, such as a gel or foam, to the surface of the gasket that is configured to contact the skin before the subject 405 "puts on" the sleep-apnea system 420. This sealant can also moisturize and otherwise soothe or heal the subject's skin to prevent marks, sores, or a rash in the area in which the gasket 522 contacts the skin. Furthermore, the gasket 522 can include one or more of the sealant-dispensing openings 210 (FIG. 15) through which a sealant-dispenser assembly 124 (FIGS. 8 and 45) can dispense a sealant from a sealant reservoir 146 (FIGS. 8 and 45) to form a seal, or to stop a leak in the seal, as described above in conjunction with FIGS. 8 and 15. Moreover, the seal formed by the gasket 522 can be enhanced by a replaceable and disposable self-adhesive sealing member (not shown in FIGS. 39-40) that has one side configured to adhere to the skin-facing surface of the gasket 522, and has another side configured to contact the skin and having an adhesive or other substance to enhance the seal with the skin. One could replace such a sealing member periodically, e.g., daily prior to each use, and more often than one replaces the gasket 522 and gasket assembly 422.

Referring again to FIG. 39, the one or more electrodes 510 (two electrodes 510a and 510b shown in FIG. 39) can function as sensors, as therapy-applying devices, or as both sensors and therapy-applying devices. For example, while functioning as sensors, the controller 134 (FIGS. 8 and 45), or other circuitry, of the sleep-apnea-treatment system 420 can be configured to measure a voltage across the electrodes 510a and 510b, and to measure respective currents into or out of the electrodes, where the voltage, currents, or both the voltage and currents (e.g., magnitude, phase of voltage or currents) can indicate a level of sleep apnea being experienced by the subject 405 (e.g., FIG. 38), or can indicate a condition or parameter of the subject such as blood pressure, blood-sugar level, blood-oxygen level, and body or skin temperature. And while functioning as therapy-applying devices, the controller 134, or other circuitry, of the sleep-apnea-treatment system 420 can be configured to apply a voltage across the electrodes 510a and 510b, and to apply respective currents into or out of the electrodes to treat the subject 405 (e.g., the controller/circuitry can be configured to control the magnitudes and phases of the voltage and currents). Examples of such treatments include reducing a level of sleep apnea, reducing high blood pressure, reducing high blood-sugar level, and increasing low blood-oxygen level. Examples of how the controller 134 or circuitry can effect such treatments include changing body or skin temperature, and relaxing, tensing, or "shocking" the muscles and other tissues, e.g., in the subject's neck or throat. Any data collected from the subject may be stored and/or shared with other devices (e.g., a physician, a database of other users, a mobile device, tablet, social media, etc.)

Figure 41:
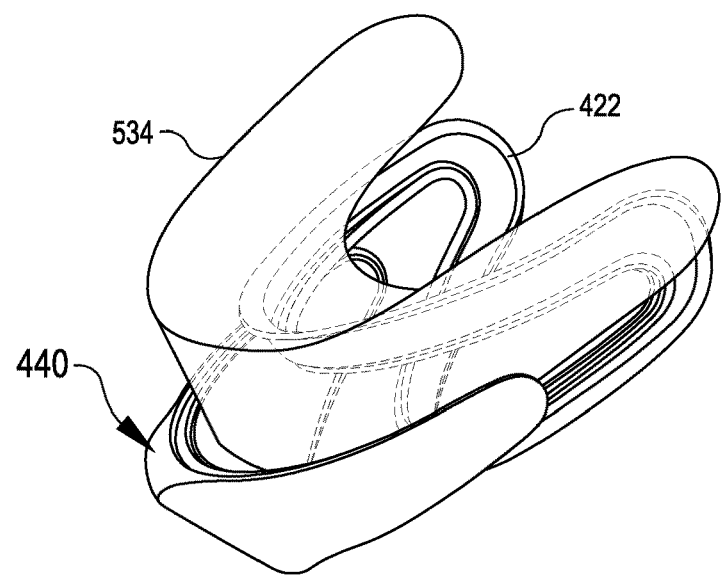
FIG. 41 is an isometric exploded view of the sleep-apnea-treament system of FIGS. 26-32 including a replaceable sleeve, according to an embodiment.

FIG. 41 is an isometric exploded view of the gasket assembly 422, the collar 440, and a sleeve 534 of the negative-pressure sleep-apnea-treatment system 420 of FIGS. 26-32 and 38, according to an embodiment. The sleeve 534 can be configured for disposal between the collar 440 and the gasket assembly 422, and can be held in place in any suitable manner. For example, one can install the sleeve 534 against, or adjacent to, the rear surface 454 of the collar 440, and then secure the sleeve in place by "snapping" the gasket assembly 422 to the collar rim 526 as described above in conjunction with FIGS. 39-40. Or, one can secure the sleeve 534 to the collar 440 or gasket assembly 422 with an adhesive. Furthermore, the sleeve 534 can be made from any suitable material, such as a soft, breathable, moisture-wicking fabric, to make the sleep-apnea system 420 more comfortable to the subject 405 (e.g., FIG. 38), as compared to the sleep-apnea system without the sleeve, while still allowing the sleep-apnea system to draw a vacuum through the sleeve to create a negative-pressure region between the sleeve and the subject's neck 400 (e.g., FIG. 38). Moreover, some or all of the sleep-apnea-system components (e.g., pump, motor, controller, battery, temperature sensor, temperature adjuster) can be secured to, or disposed within one or more compartments formed in, the sleeve 534. In addition, the sleeve 534 can be machine washable and replaceable; if there are components secured to or disposed within the sleeve, then these components can be discarded with a used sleeve and replaced with a new sleeve, or the components can be removed from the used sleeve and reinstalled with the new sleeve. Furthermore, the sleeve 534 can be configured to extend partially or fully around the subject's neck 400.

Figure 42:
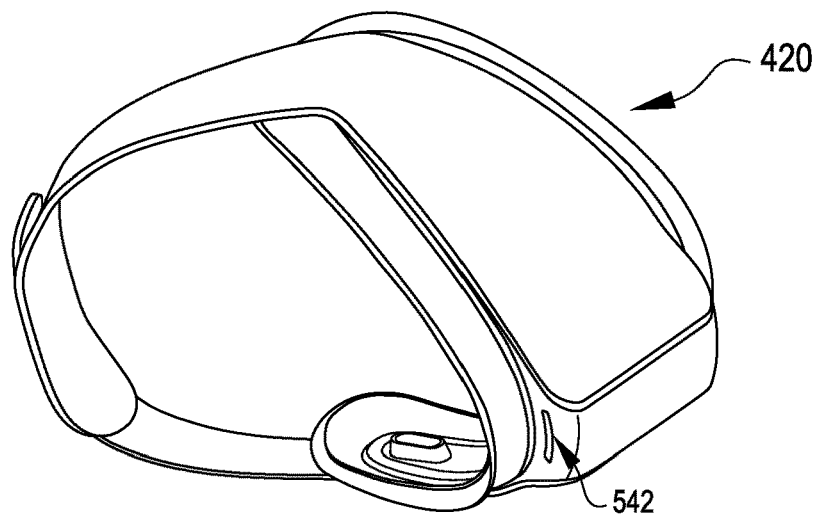
FIG. 42 is an isometric view of the sleep-apnea-treatment system of FIGS. 26-32 including battery-charging contacts, according to an embodiment.

FIG. 42 is an isometric view of the sleep-apnea-treatment system 420 of FIGS. 26-32 and 38, according to an embodiment in which the sleep-apnea system includes a rechargeable battery 110 (FIGS. 8 and 45).

Figure 43:
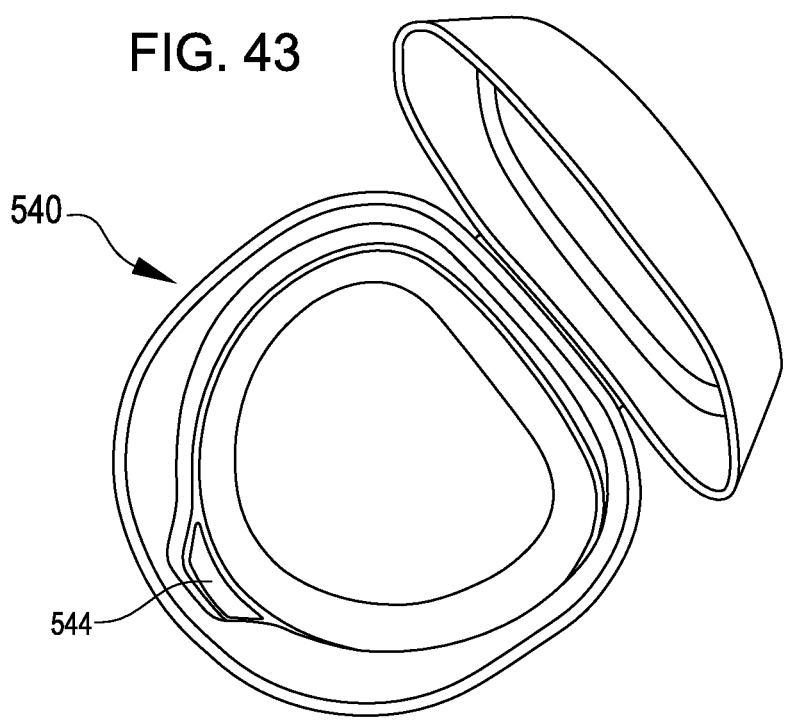
FIG. 43 is an isometric top view of a battery-charging storage case, in an open position, for the sleep-apnea-treatment system of FIG. 42, according to an embodiment.

FIG. 43 is an isometric top view of an empty charging-and-storage case 540 for the sleep-apnea treatment system 420 of FIG. 41, according to an embodiment.

Figure 44:
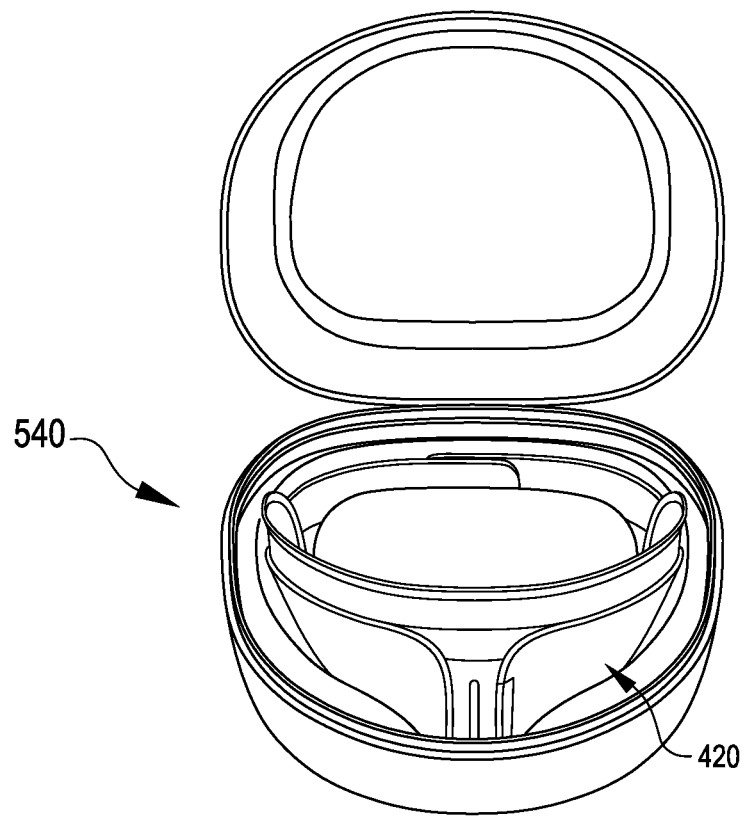
FIG. 44 is an isometric view of the sleep-apnea treatment system of FIG. 42 disposed in the battery-charging storage case of FIG. 43, according to an embodiment.

FIG. 44 is an isometric front view of the sleep-apnea-treatment system 420 of FIG. 42 inside of the charging-and-storage case 540 of FIG. 43, according to an embodiment.

Referring to FIGS. 42-44, the sleep-apnea system 420 includes electrically conductive charging contacts 542, which are configured to engage electrically conductive charging contacts 544 disposed in the case 540 while the sleep-apnea system is being stored in the case.

The charging-and-storage case 540 can be made from any suitable material, and can have any suitable configuration. For example, the charging case 540 can be made from a plastic and can have a rear-hinged clamshell configuration such as shown in FIGS. 43-44.

Furthermore, the charging-and-storage case 540 is configured to receive a power signal (e.g., an input voltage or an input current) from a power source (not shown in FIGS. 42-44) such as a standard alternating-current (AC) wall outlet (110 or 220 VAC), an AC adapter (e.g., a "wall wart"), a solar cell, and another battery, and can receive the power signal either via a wired connection (e.g., a power cord) or wirelessly (e.g., inductively or otherwise electromagnetically).

Either the sleep-apnea system 420 or the charging-and-storage case 540 includes battery-charging circuitry (not shown in FIGS. 42-44) that is configured to convert the power signal from the power source into a charging signal (e.g., a charging current or a charging voltage) suitable for charging the battery 110 (FIGS. 8 and 45) on board (e.g., in the compartment 462 of FIG. 34) the sleep-apnea system 420. If the sleep-apnea system 420 includes the battery-charging circuitry, then the case 540 provides to the battery-charging circuitry, via the charging contacts 542 and 544, the power signal from the power source to which the case is coupled. But if the case 540 includes the battery-charging circuitry, then the case provides to the battery 110, via the charging contacts 542 and 544, the charging signal. In an embodiment, the case 540 includes the battery-charging circuitry to reduce the size and weight of the sleep-apnea system 420.

Alternatively, the sleep-apnea system 420 and the charging-and-storage case 540 can omit the contacts 542 and 544, and the case can be configured to provide the power signal, or the charging signal, to the sleep-apnea system in a wireless manner. For example, the case 540 can be configured to provide the power signal or charging signal to the sleep-apnea system 420 inductively, i.e., in a manner similar to the manner in which a card reader provides a power signal to circuitry on board a smart card.

FIG. 45 is a block diagram of a component module 550 of the negative-pressure sleep-apnea-treatment system 420 of FIGS. 26-32, 38, 42, and 44, according to an embodiment. For example, the component module 550 can be partially or fully disposed within the collar compartment 462 of the collar 440 (FIG. 34); if only partially disposed within the compartment, then the remaining portions of the component module can be disposed in other sections of the collar, the gasket assembly 422, or outside of the collar and gasket assembly.

Unless stated otherwise, the structures and functions of the components of the component module 550 can be the same as, or similar to, the structures and functions of the corresponding components of the component module 74 of FIG. 8; therefore, like components of the component module 550 are identified with the same reference numerals as corresponding components of the component module 74.

And, unless stated otherwise, the sleep-apnea system 420 of FIGS. 26-32, 38, 42, and 44, and the component module 550 and its components, can be configured to operate according to the flow diagram 270 of FIG. 23.

In addition to the structure and functions of the power-switch assembly 100 described above in conjunction with FIG. 8, the power-switch assembly can include the switch 480 and other circuitry described above in conjunction with FIG. 36. Furthermore, in addition to be operated manually, the power-switch assembly 100 can be operated, e.g., to turn the sleep-apnea system 420 "on" (activate) and "off" (deactivate), by a remote-control device such as the remote-control device 484 (FIG. 37). Moreover, the power-switch assembly 100 can be operated to activate and deactivate the sleep-apnea system 420 while the sleep-apnea system is disposed in a base or case (e.g., the case 540 of FIGS. 43-44), or while the sleep-apnea system is attached to a vacuum hose (not shown in FIG. 45), in which case the power-switch assembly can be configured to allow the subject 405 (e.g., FIG. 38) to activate and deactivate a vacuum source disposed in a base unit to which the hose is attached. In addition, the power-switch assembly 100 can be configured to automatically deactivate the sleep-apnea system 420 when the subject 405 removes the sleep-apnea system from his/her body. For example, the sleep-apnea system 420 can include a sensor (e.g., accelerometer, gyroscope, temperatures sensor, infrared sensor) configured to sense when the subject 405 puts on, or takes off, the sleep-apnea system 420.

In addition to the functions of the motor assembly 116 and the pump assembly 118 described above in conjunction with FIG. 8, controller 134 can be configured to activate the motor assembly, and, therefore, to drive the one or more pumps of the pump assembly, intermittently to save power as compared to activating the motor and driving the one or more pumps continuously. For example, the controller 134 can be configured to operate the motor assembly 116 and pump assembly 118 using hysteresis as follows to open the subject's airway 14 (FIG. 1). The controller 134 is configured to activate the motor assembly 116 to drive one or more pumps of the pump assembly 118 until the magnitude of negative pressure in one or more pressure regions equals or exceeds a magnitude of a first threshold. The controller 134 is configured then to deactivate the motor assembly 116 until the magnitude of the negative pressure falls to, or below, a magnitude of a second threshold that is less than the magnitude of the first threshold. In response to the magnitude of the negative pressure equaling or being less than, the magnitude of the second threshold, the controller 134 is configured to activate the motor assembly 116 to repeat the hysteresis cycle.

Furthermore, in addition to the components described above in conjunction with the component module 74 of FIG. 8, the component module 550 includes at least a communication circuit 552, a condition-and-other-sensor assembly 554, and a therapy assembly 556.

The communication circuit 552 is configured to allow the controller 134 to communicate with a remote device, such as a remote computer system or a remote device such as the remote-control device 484 (FIG. 37). For example, the communication circuit 552 can include circuitry, a connector, and an antenna that are configured to allow the controller 134 to communicate with a remote device over a wired Ethernet® connection, and over a wireless channel, such as a Bluetooth®, Wi-Fi®, Zigbee®, infrared, or radio-frequency (RF) channel. The controller 134 is configured, e.g., to receive instructions and settings from the remote device, to provide to the remote device status, usage, and other information regarding the sleep-apnea system 420 (FIGS. 26-32, 38, 42, and 44), and to provide to the remote device information regarding the subject 405 (e.g., FIG. 38), who uses the sleep-apnea system. Examples of such instructions and settings include a maximum negative-pressure threshold for the one or more negative-pressure regions generated by the sleep-apnea system 420, a wake-up time, and whether to dispense a sealant with the sealant-dispenser assembly 124. Examples of status, usage, and other information include the charge level of the battery 110, hours that the subject 405 has used the sleep-apnea system 420, and a profile of detected apnea events (e.g., a profile of the degrees/magnitudes of apnea events, the number of apnea events per unit time, the average change in the degrees/magnitudes of apnea events, and the change in the number of apnea events per unit time), and whether it is time to replace one or more specified components of the sleep-apnea system. And examples of information regarding the subject 405 include a profile (e.g., magnitude, phase, change in magnitude, and change in phase) of physical conditions or parameters (e.g., blood pressure, blood-sugar level) of the subject over time. Furthermore, the communication circuit 552 can be configured to allow the controller 134 to upload this information to a database, such as a cloud database. Moreover, if the controller 134 is configured to operate by executing software instructions, or is otherwise software or firmware configurable, then the controller can be configured to download software and firmware via the communication circuit 552.

Still referring to FIG. 45, the condition-and-other-sensor assembly 554 can include one or more sensors that are configured to sense one or more conditions of the subject 405 (e.g., FIG. 45), or other conditions, for reasons other than detecting a level of sleep apnea being experienced by the subject, and for reasons other than detecting a level of negative pressure generated between the collar 440 (e.g., FIG. 44) and the neck 400 (e.g., FIG. 38) of the subject 405. For example, the assembly 554 can include one or more sensors configured to detect conditions (e.g., blood pressure, blood-sugar level, body-movement level, sleep quality) that indicate a level of health or comfort of the subject 405. Furthermore, the assembly 554 can include one or more sensors configured to detect conditions of the subject's usage (e.g., when the subject falls asleep, when the subject awakens, when the subject puts on and removes) of the sleep-apnea treatment system 420, and conditions (e.g., ambient temperature, level of ambient light, level of ambient/background noise, level of pollution) of the environment in which the subject 405 is immersed while using the sleep-apnea system.

Following are descriptions of sensors that can be included in the apnea-degree sensor assembly 128, in the condition-and-other-sensor assembly 554, or in both of the sensor assemblies 128 and 554. For example, each sensor assembly 128 and 554 can include a respective sensor of a same type (e.g., pulse oximetry), or the assemblies 128 and 554 effectively can share such a sensor, which the controller 134 can use, e.g., to determine a level of sleep apnea being experienced by the subject 405 (e.g., FIG. 38) and to determine a condition of the subject for purposes other than determining a level of sleep apnea being experienced by the subject.

For example, one or both of the sensor assemblies 128 and 554 can include a conventional pulse-oximetry (pulse-ox) sensor, which is configured to generate a signal indicative of a level of oxygen in the subject's blood, and which also can be configured to generate a signal indicative of the subject's heart rate.

There are two types of pulse-ox sensor: a reflective type, and a transmissive type. Although only the reflective type of pulse-ox sensor is described in detail herein, the assemblies 128 and 554 can also include the transmissive type of pulse-ox sensor.

A reflective pulse-ox sensor transmits, into the skin of the subject 405, two signals at respective near-infrared (IR) wavelengths, and a blood vessel of the subject redirects portions of the first and second signals back to the pulse-ox sensor. The amplitude of the received redirected portion of the first signal is independent of the amount of oxygen being carried by the hemoglobin in the blood flowing through the blood vessel; therefore, the first signal acts as a reference signal. In contrast, the amplitude of the received redirected portion of the second signal is proportional to the amount of oxygen being carried by the hemoglobin in the blood flowing through the blood vessel. Because both the first and second signals experience the same attenuation from the tissues through which they propagate, the difference in the amplitudes of the signals is proportional to the level of oxygen in the subject's blood.

The reflective pulse-ox sensor is configured to receive the redirected portions of the first and second signals, and circuitry in the sensor, or separate from the sensor (e.g., in the sensor assembly 128, the sensor assembly 554, the controller 134, or elsewhere in the component module 550), is configured to determine, in a conventional manner, a pulse-ox reading in response to the difference in the amplitudes of the received redirected portions of the first and second signals.

Circuitry in the sensor, or separate from the sensor, can also be configured to determine the subject's heart rate in response to the difference in the amplitudes of the received redirected portions of the first and second signals. Because there is always some oxygen in the blood of a living subject 405, during a high-pressure (i.e., systolic) portion of the subject's cardiac cycle, the amplitude of the redirected portion of the second signal is higher because there is more blood, and, therefore, more total oxygen, in the portion of the blood vessel on which the two transmitted IR signals are incident; similarly, during a low-pressure (i.e., diastolic) portion of the cardiac cycle, the amplitude of the redirected portion of the second signal is lower because there is less blood, and, therefore, less total oxygen, in the portion of the blood vessel on which the two transmitted IR signals are incident. Therefore, passing a signal that represents the difference between the amplitudes of the first and second received redirected signals through a bandpass filter having a pass band of approximately 50 Hz to 300 Hz results in a filtered signal having a frequency that is approximately equal to the subject's heart rate.

If the pulse-ox sensor is included in the apnea-degree sensor assembly 128, then the controller 134 can be configured to use the information provided by the pulse-ox sensor to determine a degree of sleep apnea being experienced by the subject 405 (e.g., FIG. 38). While a subject's airway 14 (FIG. 1) is obstructed during an obstructive-sleep-apnea event, the level of oxygen reaching the subject's blood via his/her lungs is reduced, and his/her heart rate becomes elevated. Therefore, by detecting at least one of a decrease in blood oxygen level and an increase in heart rate, the controller 134 can determine that the subject is experiencing a sleep-apnea event, and can take appropriate action (e.g., increasing the magnitude of the negative pressure being applied to the subject's throat region 406 or throat region 407 (FIGS. 24-25)) to alleviate the obstruction.

In some cases, the time between commencement of an airway obstruction and a measurable decrease in blood-oxygen level, or a measurable increase in heart rate, may be too long for blood-oxygen level or heart rate to be used as an indicator of sleep-apnea to which the controller 134 responds.

But even in these cases, a low blood-oxygen level or an elevated heart rate can be used as an indicator that the subject 405 is still recovering from a sleep-apnea event that the controller 134 detected via sensing of another marker.

And if the pulse-ox sensor is included in the condition-and-other-sensory assembly 554, then the controller 134 can be configured to use the information provided by the pulse-ox sensor to determine a health condition or other parameter of the subject 405. For example, a low blood-oxygen level, or an elevated, depressed, or erratic heart rate, over an extended period of time, can indicate that the subject 405 has a health problem such as a chronic obstructive pulmonary disease (COPD), or a heart problem such as atrial fibrillation or another heart arrhythmia, congestive heart failure, or blood-vessel blockage. Therefore, in response to such information from the pulse-ox sensor, the controller 134 can be configured to warn the subject 405, via the output device 140 or the communication circuit 552, of the abnormal parameter and suggest that the subject see a doctor. Or, the controller 140 even can be configured to diagnose the problem responsible for the abnormal parameter and to inform the subject 405, or the subject's doctor, via the output device 140 or the communication circuit 552.

Still referring to FIG. 45, one or both of the sensor assemblies 128 and 554 can include an audio sensor, such as a piezoelectric microphone, which is configured to generate a signal indicative of a level of sound that it receives.

Circuitry in the audio sensor, or separate from the audio sensor, can be configured to filter, or otherwise to process, the signal generated by the audio sensor so that the controller 134 can glean information from the signal. For example, the circuitry can be configured to filter the sensor signal to yield a filtered signal having a frequency approximately equal to the subject's breathing rate. Or, the circuitry can be configured to analyze, spectrally, the sensor signal to yield breathing sounds made by the subject 405 (e.g., FIG. 38), or to yield a breathing volume of the subject.

If the audio sensor is included in the apnea-degree sensor assembly 128, then the controller 134 can be configured to use the information provided by the audio sensor to determine a degree of sleep apnea being experienced by the subject 405. For example, in response to the subject's airway 14 (FIG. 1) being obstructed during an obstructive-sleep-apnea event, the breathing sounds (e.g., snoring) that the subject 405 makes can change, the subject's breathing rate can change, or the subject's breathing volume (i.e., the amount of air inhaled or exhaled) can change. As stated above, circuitry can be configured to process the signal generated by the audio sensor, and the controller 134 can be configured to determine, in response to the processed signal, whether a subject is experiencing a sleep-apnea event, and the level or degree of such an event. For example, the controller 134 can be configured to determine, in response to the processed signal, a breathing-sound profile of the subject 405 over time, and the look-up table (LUT) 148 can store representations of, and correlate, different breathing-sound profiles of the subject with respective levels of airway obstruction being experienced by the subject. By retrieving from the LUT 148 the level of airway obstruction corresponding to the determined breathing-sound profile (or corresponding to the stored profile that most closely matches the determined profile), the controller 134 can determine the level of airway obstruction being experienced by the subject 405 in response to the sensed breathing sounds, and can take appropriate action (e.g., increasing the magnitude of the negative pressure being applied to the subject's throat region 406 or throat area 407 (FIGS. 24-25)). Similarly, the controller 134 can be configured to determine a breathing-rate or breathing-volume profile of the subject 405, and the LUT 148 can store and correlate different breathing-rate or breathing-volume profiles of the subject with respective levels of airway obstruction being experienced by the subject. By retrieving from the LUT 148 the level of airway obstruction corresponding to the determined breathing-rate or breathing-volume profile (or the stored profile that most closely matches the determined profile), the controller 134 can determine the level of airway obstruction being experienced by the subject in response to the sensed breathing rate or sensed breathing volume, and can take appropriate action (e.g., increasing the magnitude of the negative pressure being applied to the subject's throat region 406 or throat area 407 (FIGS. 24-25)) to alleviate the obstruction.

If the audio sensor is included in the condition-and-other-sensory assembly 554, then the controller 134 can be configured to use the information provided by the audio sensor to determine a health condition or other parameter of the subject. For example, a low breathing rate, or a low breathing volume, over an extended period of time can indicate that the subject has a health problem such as a chronic obstructive pulmonary disease (COPD) or an airway obstruction that the sleep-apnea system 420 cannot alleviate. Therefore, in response to such information from the audio sensor, the controller 134 can be configured to warn the subject 405, via the output device 140 or communication circuit 552, of the abnormal parameter and suggest that the subject see a doctor. Or, the controller 134 even can be configured to diagnose the problem responsible for the abnormal parameter, and to provide the diagnosis to the subject 405 or the subject's doctor via the output device 140 or the communication circuitry 552.

Furthermore, one or both of the sensor assemblies 128 and 554 can include a motion sensor, such as a MEMS accelerometer or gyroscope, which can be configured to generate a signal indicative of a level of motion that it experiences, e.g., due to movement of the subject 405 (e.g., FIG. 38).

Circuitry in the motion sensor, or separate from the motion sensor, can be configured to filter, or otherwise to process, the signal generated by the motion sensor so that the controller 134 can glean information from the signal. For example, the motion sensor can be configured to sense the rising and falling of the subject's chest (not shown in FIG. 45) as he/she breathes, where the frequency of this rising and falling is the subject's breathing rate, and the amplitude of this rising and falling is proportional to the subject's breathing volume. Therefore, the circuitry can be configured to filter the sensor signal to yield a filtered signal having a frequency approximately equal to the subject's breathing rate. Or, the circuitry can spectrally analyze the sensor signal to yield a representation of other breathing movements (e.g., coughing or gasping) made by the subject 405, or to yield a representation of the breathing volume of the subject. In addition, if the motion sensor is close enough to one of the subject's carotid arteries, then the circuitry can be configured to filter the sensor signal to yield a filtered signal having a frequency equal to the subject's heart/pulse rate.

If the motion sensor is included in the apnea-degree sensor assembly 128, then the controller 134 can be configured to use the information provided by the motion sensor to determine a degree of sleep apnea being experienced by the subject 405. In response to the subject's airway 14 (FIG. 1) being obstructed during an obstructive-sleep-apnea event, the breathing movements (e.g., vibrations from snoring, rising and falling of chest, coughing, gasping) that the subject 405 makes can change, the subject's breathing rate can change, the subject's breathing volume can change, and the subject's heart rate can change. As stated above, circuitry can be configured to process the signal generated by the motion sensor, and the controller 134 can be configured to determine, in response to the processed signal, whether the subject 405 is experiencing a sleep-apnea event, and the degree/level of such an event. For example, the controller 134 can be configured to determine, in response to the processed signal, a breathing-movement profile of the subject 405, and the LUT 148 can store and correlate different breathing-movement profiles of the subject with respective levels of airway obstruction being experienced by the subject. By retrieving from the LUT 148 the level of airway obstruction corresponding to the determined breathing-movement profile (or corresponding to the stored profile that most closely matches the determined profile), the controller 134 can determine the level of airway obstruction being experienced by the subject 405 in response to the sensed breathing movements, and can take appropriate action (e.g., increasing the magnitude of the negative pressure being applied to the subject's throat region 406 or throat region 407 (FIGS. 24-25)). Similarly, the controller 134 can be configured to determine a breathing-rate, breathing-volume, or heart-rate profile of the subject 405, and the LUT 148 can store and correlate different breathing-rate, breathing-volume, or heart-rate profiles of the subject with respective levels of airway obstruction being experienced by the subject. By retrieving from the LUT 148 the level of airway obstruction corresponding to the determined breathing-rate, breathing-volume, or heart-rate profile (or corresponding to the stored profile that most closely matches the determined profile), the controller 134 can determine the level of airway obstruction being experienced by the subject in response to the sensed breathing rate, breathing volume, or heart rate, and can take appropriate action to reduce the degree of, or eliminate, the airway obstruction.

If the motion sensor is included in the condition-and-other-sensory assembly 554, then the controller 134 can be configured to use the information provided by the motion sensor to determine a health condition or other parameter of the subject. For example, excessive body movement over an extended period of time can indicate that the subject 405 is not sleeping comfortably or deeply enough, is sleepwalking, or has restless-leg syndrome. Therefore, in response to such information from the motion sensor, the controller 134 can be configured to warn the subject 405 or his/her doctor, via the output device 140 or the communication circuitry 552, of the abnormal parameter, and to suggest that the subject see his/her doctor. Or, the controller 140 even can be configured to diagnose the problem responsible for the abnormal parameter, and to provide the diagnosis to the subject 405 or to the subject's doctor via the output device 140 or the communication circuitry 552.

Moreover, one or both of the sensor assemblies 128 and 554 can include a stroke-volume sensor, such as micro-impulse radar transceiver, which can be configured to generate a signal indicative of a stroke volume, or a change in stroke volume, of the subject's heart (stroke volume is the volume of blood that the left ventricle pumps during a cardiac cycle).

Circuitry in the stroke-volume sensor, or separate from the stroke-volume sensor, can be configured to filter, or otherwise to process, the signal generated by the stroke-volume sensor so that the controller 134 can glean the stroke volume of the subject's heart from the signal. For example, the signal generated by the sensor can represent images of the left ventricle over time, and the circuitry can filter the signal such that the amplitude of the filtered signal is proportional to the stroke volume (the difference between the left ventricle at its largest volume and at its smallest volume).

If the stroke-volume sensor is included in the apnea-degree sensor assembly 128, then the controller 134 can be configured to use the information provided by the stroke-volume sensor to determine a degree of sleep apnea being experienced by the subject 405. In response to the subject's airway 14 (FIG. 1) being obstructed during an obstructive-sleep-apnea event, the stroke volume of the subject's heart may increase as the heart tries to provide more oxygen to the subject's tissues with blood that is less oxygenated than blood outside of an obstructive-sleep-apnea event. That is, the stroke volume increases to compensate for the lower level of oxygen in the subject's blood due to the airway obstruction. As stated above, circuitry can be configured to process the signal generated by the stroke-volume sensor, and the controller 134 can be configured to determine, in response to the processed signal, whether a subject is experiencing a sleep-apnea event, and the degree/level of such an event. For example, the controller 134 can be configured to determine, in response to the processed signal, a stroke-volume profile of the subject 405, and the LUT 148 can store and correlate different stroke-volume profiles of the subject with respective degrees/levels of airway obstruction being experienced by the subject. By retrieving from the LUT 148 the level of airway obstruction corresponding to the determined stroke-volume profile (or corresponding to the stored profile that most closely matches the determined profile), the controller 134 can determine the level of airway obstruction being experienced by the subject 405 in response to the sensed stroke volume, and can take appropriate action (e.g., increasing the magnitude of the negative pressure being applied to the subject's throat region 406 or throat region 407 (FIGS. 24-25)) to alleviate the obstruction.

In some cases, the time between commencement of an airway obstruction and a measurable increase in stroke volume is too long for stroke volume to be used as a sleep-apnea marker to which the controller 134 responds.

But even in these cases, the stroke volume can be used as an indicator that the subject 405 is still recovering from a sleep-apnea event that was detected via sensing of another sleep-apnea marker (e.g., breathing sound).

If the stroke-volume sensor is included in the condition-and-other-sensory assembly 554, then the controller 134 can be configured to use the information provided by the stroke-volume sensor to determine a health condition or other parameter of the subject 405. For example, excessive or low stroke volume over an extended period of time while the subject 405 is sleeping can indicate that the subject is not sleeping comfortably or deeply enough, is sleepwalking, or has a heart problem such as congestive heart failure. Therefore, in response to such information from the stroke-volume sensor, the controller 134 can be configured to warn the subject 405 or his/her doctor, via the output device 140 or the communication circuitry 552, of the abnormal stroke volume, and to suggest that the subject see a doctor. Or, the controller 140 even can be configured to diagnose the problem responsible for the abnormal stroke volume, and to provide the diagnosis to the subject or to the subject's doctor via the output device 140 or the communication circuitry 552.

And because stroke volume occurs periodically, a stroke-volume sensor and its associated circuitry can also be configured to provide the heart rate of the subject 405 (e.g., FIG. 38).

In addition, one or both of the assemblies 128 and 554 can include a conventional gas sensor (e.g., a spectral gas sensor), which can be configured to generate a signal indicative of a fraction or level (e.g., by mass, volume, or number of molecules), or a change in a fraction or level, of a substance in a subject's exhalant (i.e., the air exhaled by the subject 405). Examples of such a substance include water vapor, carbon dioxide ($CO_2$), oxygen ($O_2$), and volatile organic compounds (VOCs). And if the substance sensed is $CO_2$, then the gas sensor can include a non-dispersive infrared $CO_2$ module.

Circuitry in the gas sensor, or separate from the gas sensor, can be configured to filter, or otherwise to process, the signal generated by the gas sensor so that the controller 134 can glean a fraction or level, or a change in the fraction or level, of a substance exhaled by the subject as compared to the total of substances exhaled by the subject.

If the gas sensor is included in the apnea-degree sensor assembly 128, then the controller 134 can be configured to use the information provided by the gas sensor to determine a degree of sleep apnea being experienced by the subject 405. In response to the subject's airway 14 (FIG. 1) being obstructed during an obstructive-sleep-apnea event, the fraction or level of a substance in the subject's exhalant can increase (e.g., $CO_2$) or decrease (e.g., $O_2$). As stated above, circuitry can be configured to process the signal generated by the gas sensor, and the controller 134 can be configured to determine, in response to the processed signal, whether the subject 405 is experiencing a sleep-apnea event, and the degree/level of such an event. For example, the controller 134 can be configured to determine, in response to the processed signal, an exhaled-substance profile of the subject 405, and the LUT 148 can store and correlate different exhaled-substance profiles of the subject 405 with respective degrees/levels of airway obstruction that the subject is experiencing. By retrieving from the LUT 148 the degree/level of airway obstruction corresponding to the determined exhaled-substance profile (or corresponding to the stored profile that most closely matches the determined profile), the controller 134 can determine the level of airway obstruction that the subject 405 is experiencing in response to the sensed exhaled substance, and can take appropriate action (e.g., increase the magnitude of the negative pressure being applied to the subject's throat region 406 or throat region 407 (FIGS. 24-25)) to alleviate the obstruction.

If the gas sensor is included in the condition-and-other-sensory assembly 554, then the controller 134 can be configured to use the information provided by the gas sensor to determine a health condition or other parameter of the subject 405. For example, exhaling an excessive fraction or level of $CO_2$ over an extended period of time while the subject 405 is sleeping can indicate that the subject is not sleeping comfortably or deeply enough, or has a lung problem. Therefore, in response to such information from the gas sensor, the controller 134 can be configured to warn the subject 405 or his/her doctor, via the output device 140 or the communication circuitry 552, of the abnormal exhalant profile, and to suggest that the subject see a doctor. Or, the controller 140 even can be configured to diagnose the problem responsible for the abnormal exhalant profile, and to provide the diagnosis to the subject 405 or his/her doctor via the output device 140 or the communication circuitry 552.

Still referring to FIG. 45, one or both of the assemblies 128 and 554 can include a conventional chemical sensor, which can be configured to generate a signal indicative of a fraction or level (e.g., by mass, volume, or number of molecules), or a change in a fraction or level, of a sensed substance (e.g., in a liquid or a gas phase) in, for example, the subject's sweat, exhalant, saliva, lipids, or tears. Examples of such a substance include hormones such as cortisol, alcohol, water vapor, carbon dioxide ($CO_2$), oxygen ($O_2$), and volatile organic compounds (VOCs).

Circuitry in the chemical sensor, or separate from the chemical sensor, can be configured to filter, or otherwise to process, the signal generated by the chemical sensor so that the controller 134 can glean a fraction or level, or a change in the fraction or level, of a substance excreted by the subject 405 as compared to the total of substances excreted by the subject.

If the chemical sensor is included in the apnea-degree sensor assembly 128, then the controller 134 can be configured to use the information provided by the chemical sensor to determine a degree/level of sleep apnea that the subject 405 is experiencing. In response to the subject's airway 14 (FIG. 1) being obstructed during an obstructive-sleep-apnea event, the fraction or level of a substance that the subject 405 excretes can increase (e.g., cortisol) or decrease. As stated above, circuitry can be configured to process the signal generated by the chemical sensor, and the controller 134 can be configured to determine, in response to the processed signal, whether the subject 405 is experiencing a sleep-apnea event, and the degree/level of such an event. For example, the controller 134 can be configured to determine, in response to the processed signal, a sweat- or saliva-substance profile of the subject 405, and the LUT 148 can store and correlate different sweat- and saliva-substance profiles of the subject with respective levels of airway obstruction being experienced by the subject 405. By retrieving from the LUT 148 the level of airway obstruction corresponding to the determined sweat- and saliva-substance profile (or corresponding to the stored profile that most closely matches the determined profile), the controller 134 can determine the level of airway obstruction that the subject 405 is experiencing in response to the sensed excreted substance, and can take appropriate action (e.g., increasing the magnitude of the negative pressure being applied to the subjects throat region 406 or throat region 407 (FIGS. 24-25)) to alleviate the obstruction.

If the chemical sensor is included in the condition-and-other-sensory assembly 554, then the controller 134 can be configured to use the information provided by the chemical sensor to determine a health condition or other parameter of the subject's wellbeing. For example, sweating out an excessive fraction or level of cortisol over an extended period of time while the subject 405 is sleeping can indicate that the subject is not sleeping comfortably or deeply enough; similarly sweating out an excessive fraction or level of alcohol over an extended period of time while the subject is sleeping can indicate that the subject is drunk, and, therefore, may have a drinking problem. Therefore, in response to such information from the chemical sensor, the controller 134 can be configured to warn the subject 405 or his/her doctor, via the output device 140 or the communication circuitry 552, of the abnormal excretion profile, and to suggest that the subject see his/her doctor. Or, the controller 140 even can be configured to diagnose the problem responsible for the abnormal excretion profile, and to provide the diagnosis to the subject 405 or his/her doctor via the output device 140 or the communication circuitry 552.

Furthermore, one or both of the sensor assemblies 128 and 554 can include an electroencephalogram (EEG) sensor assembly, which is configured to generate one or more signals that represent electrical activity in a brain of a subject 405 (e.g., FIG. 38). The EEG sensor assembly can include one or more sensors that are attached to, or are part of, the collar 440, or that are remote from the collar (an example of such a remote sensor is an epidermal electronic sensor, which can be printed, or otherwise attached or mounted, directly onto a subject's skin).

Circuitry in the EEG sensor assembly, or separate from the EEG sensor assembly, can be configured to filter, or otherwise to process, the one or more signals generated by the EEG sensor assembly so that the controller 134 can glean information from the one or more signals. For example, the circuitry can be configured to filter one or more of the one or more sensor signals to yield one or more filtered signals that represent a sleep state, or other condition, of the subject 405. Or, the circuitry can be configured to analyze, spectrally, the one or more of the one or more sensor signals to yield the sleep state or other condition of the subject 405.

If the EEG sensor assembly is included in the apnea-degree sensor assembly 128, then the controller 134 can be configured to use the information provided by the EEG sensor assembly to determine a degree of sleep apnea being experienced by the subject 405. For example, in response to the subject's airway 14 (FIG. 1) being obstructed during an obstructive-sleep-apnea event, the sleep state of the subject 405 can change, or the electrical activity in the subject's brain can otherwise change. As stated above, circuitry can be configured to process the one or more signals generated by the EEG sensor assembly, and the controller 134 can be configured to determine, in response to the processed one or more signals, whether a subject is experiencing a sleep-apnea event, and the level or degree of such an event. For example, the controller 134 can be configured to determine, in response to the one or more processed signals, a sleep-state profile or a brain-wave profile of the subject 405 over time, and the look-up table (LUT) 148 can store representations of, and correlate, different sleep-state and brain-wave profiles of the subject with respective levels of airway obstruction being experienced by the subject. By retrieving from the LUT 148 the level of airway obstruction corresponding to the determined sleep-state or brain-wave profile (or corresponding to the stored profile that most closely matches the determined profile), the controller 134 can determine the level of airway obstruction being experienced by the subject 405 in response to the sensed sleep state or brain electrical activity, and can take appropriate action (e.g., increasing the magnitude of the negative pressure being applied to the subject's throat region 406 or throat area 407 (FIGS. 24-25)).

If the EEG sensor assembly is included in the condition-and-other-sensory assembly 554, then the controller 134 can be configured to use the information provided by the EEG sensor assembly to determine a health condition or other parameter of the subject. For example, a poor sleep-state profile (e.g., not entering one or more sleep states, staying in a sleep state for too short or too long a time) over an extended period of time can indicate that the subject has a health problem such as a chronic obstructive pulmonary disease (COPD), an airway obstruction that the sleep-apnea system 420 cannot alleviate, or a mental problem that is interfering with a subject's sleep. Therefore, in response to such information from the EEG sensor assembly, the controller 134 can be configured to warn the subject 405, via the output device 140 or communication circuit 552, of the abnormal parameter (e.g., poor sleep-state profile) and suggest that the subject see a doctor. Or, the controller 134 even can be configured to diagnose the problem (e.g., anxiety) responsible for the abnormal parameter, and to provide the diagnosis to the subject 405 or the subject's doctor via the output device 140 or the communication circuitry 552.

Moreover, one or both of the sensor assemblies 128 and 554 can include an electrocardiogram (EKG) sensor assembly, which is configured to generate one or more signals that represent electrical activity in a heart of a subject 405 (e.g., FIG. 38). The EKG sensor assembly can include one or more sensors that are attached to, or are part of, the collar 440, or that are remote from the collar (an example of such a remote sensor is an epidermal electronic sensor, which can be printed, or otherwise attached or mounted, directly onto a subject's skin).

Circuitry in the EKG sensor assembly, or separate from the EKG sensor assembly, can be configured to filter, or otherwise to process, the one or more signals generated by the EKG sensor assembly so that the controller 134 can glean information from the one or more signals. For example, the circuitry can be configured to filter one or more of the one or more sensor signals to yield one or more filtered signals that represent a sleep state, or other condition or parameter, of the subject 405. Or, the circuitry can be configured to analyze, spectrally, the one or more of the one or more sensor signals to yield the sleep state or other condition of the subject 405.

If the EKG sensor assembly is included in the apnea-degree sensor assembly 128, then the controller 134 can be configured to use the information provided by the EKG sensor assembly to determine a degree of sleep apnea being experienced by the subject 405. For example, in response to the subject's airway 14 (FIG. 1) being obstructed during an obstructive-sleep-apnea event, the sleep state of the subject 405 can change, or the electrical activity in the subject's heart can otherwise change. As stated above, circuitry can be configured to process the one or more signals generated by the EKG sensor assembly, and the controller 134 can be configured to determine, in response to the processed one or more signals, whether a subject is experiencing a sleep-apnea event, and the level or degree of such an event. For example, the controller 134 can be configured to determine, in response to the one or more processed signals, a sleep-state profile or a heart-wave profile of the subject 405 over time, and the look-up table (LUT) 148 can store representations of, and correlate, different sleep-state and heart-wave profiles of the subject with respective levels of airway obstruction being experienced by the subject. By retrieving from the LUT 148 the level of airway obstruction corresponding to the determined sleep-state or heart-wave profile (or corresponding to the stored profile that most closely matches the determined profile), the controller 134 can determine the level of airway obstruction being experienced by the subject 405 in response to the sensed sleep state or heart electrical activity, and can take appropriate action (e.g., increasing the magnitude of the negative pressure being applied to the subject's throat region 406 or throat area 407 (FIGS. 24-25)).

If the EKG sensor assembly is included in the condition-and-other-sensory assembly 554, then the controller 134 can be configured to use the information provided by the EKG sensor assembly to determine a health condition or other parameter of the subject. For example, a poor sleep-state profile (e.g., not entering one or more sleep states, staying in a sleep state for too short or too long a time) over an extended period of time can indicate that the subject has a health problem such as a chronic obstructive pulmonary disease (COPD), an airway obstruction that the sleep-apnea system 420 cannot alleviate, heart disease, or another heart problem that is interfering with a subject's sleep. Therefore, in response to such information from the EKG sensor assembly, the controller 134 can be configured to warn the subject 405, via the output device 140 or communication circuit 552, of the abnormal parameter (e.g., poor sleep-state profile, poor heart-wave profile) and suggest that the subject see a doctor. Or, the controller 134 even can be configured to diagnose the problem (e.g., heart disease, atrial fibrillation) responsible for the abnormal parameter, and to provide the diagnosis to the subject 405 or the subject's doctor via the output device 140 or the communication circuitry 552.

Furthermore, the controller 134 can be configured to determine a ballistocardiogram (BCG) from one or more of the subject's heart rate, variation in heart rate over time, change in stroke volume over time, and respiration rate, and can use the determined BCG to determine whether the subject 405 is experiencing a sleep-apnea event. For example, one or more of the above-described sensors in the apnea-degree sensor assembly 128 can sense the subject's heart rate, variation in heart rate over time, change in stroke volume over time, and respiration rate, and the sensors and their corresponding circuitry can generate signals representing these quantities. The controller 134 can be configured to determine, in response to the processed signal, a BCG profile of the subject 405, and the LUT 148 can store and correlate different BCG profiles of the subject with respective levels of airway obstruction being experienced by the subject. By retrieving from the LUT 148 the level of airway obstruction corresponding to the determined BCG profile (or corresponding to the stored profile that most closely matches the determined profile), the controller 134 can determine the level of airway obstruction being experienced by the subject, and can take appropriate action (e.g., increasing the magnitude of the negative pressure being applied to the subject's throat region 406 or throat region 407 (FIGS. 24-25)) to alleviate the obstruction.

Or, the controller 134 can be configured to use the determined BCG to determine a health condition or other parameter of the subject 405. For example, an abnormal BCG can indicate that the subject 405 has a heart problem. Therefore, in response to an abnormal BCG, the controller 134 can be configured to warn the subject 405 or his/her doctor, via the output device 140 or the communication circuitry 552, of the abnormal BCG, and to suggest that the subject see a doctor. Or, the controller 140 even can be configured to diagnose the problem responsible for the abnormal BCG, and to provide the diagnosis to the subject or his/her doctor via the output device 140 or the communication circuitry 552.

Moreover, the controller 134 can be configured to determine a photoplethysmography (PPG) from information provided by a pulse-oximetry sensor, and to use the determined PPG to determine whether the subject 405 is experiencing a sleep-apnea event. The controller 134 can be configured to determine, in response to the processed signal from the pulse-oximetry sensor, a PPG profile of the subject 405, and the LUT 148 can store and correlate different PPG profiles of the subject with respective degrees/levels of airway obstruction being experienced by the subject. By retrieving from the LUT 148 the level of airway obstruction corresponding to the determined PPG profile (or corresponding to the stored profile that most closely matches the determined profile), the controller 134 can determine the level of airway obstruction that the subject 405 is experiencing, and can take appropriate action (e.g., increasing the magnitude of the negative pressure being applied to the subject's throat region 406 or throat region 407 (FIGS. 24-25)) to alleviate the obstruction.

Or, the controller 134 can be configured to use the determined PPG to determine a health condition or other parameter of the subject 405 (e.g., FIG. 38). For example, an abnormal PPG can indicate that the subject 405 has a lung or heart problem. Therefore, in response to an abnormal PPG, the controller 134 can be configured to warn the subject 405 or his/her doctor, via the output device 140 or the communication circuitry 552, of the abnormal PPG, and to suggest that the subject see a doctor. Or, the controller 140 even can be configured to diagnose the problem responsible for the abnormal PPG, and to provide the diagnosis to the subject 405 or his/her doctor via the output device 140 or the communication circuitry 552.

Still referring to FIG. 45, the therapy assembly 556 is configured to provide, under the control of the controller 134, therapy to the subject 405 while he/she is wearing the negative-pressure sleep-apnea system 420 (FIGS. 26-32, 38, 42, and 44), according to an embodiment. For example, the therapy assembly 556 can include the electrodes 510a and 510b (FIG. 39), and can apply, via the electrodes, a current or voltage to open, or to maintain open, the subject's airway 14 (FIG. 1) by stimulating or "shocking" the subject 405. The controller 134 can be configured to implement a feedback loop that adjusts the current or voltage applied via the electrodes 510 to open, and to maintain open, the subject's airway 14. This loop can be in independent of, or combined with, a feedback loop that the controller 134 is configured to implement by adjusting a another parameter, e.g., the negative pressure within one or more of the pressure regions, to open, and to maintain open, the subject's airway 14 with the smallest magnitude of negative pressure possible. Where these feedback loops are independent, the controller 134 has at least two variables, pressure and temperature, that it can adjust to open, and maintain open, the subject's airway 14. Furthermore, the therapy assembly 556 can include piezoelectric speakers and can be configured to generate, with the speakers, a sound, such as the sound of waves breaking onto a beach, that can soothe the subject 405 and can help the subject to sleep. Or, the therapy assembly 556 can be configured to sound an alarm with the speakers to awaken the subject 405 in response to the controller 134 detecting a sleep-apnea event that endures for a time that exceeds a safe-time threshold.

Still referring to FIG. 45, alternate embodiments of the component module 550 are contemplated. For example, alternate embodiments described above in conjunction with FIG. 8 for the component module 74 may also be applicable to the component module 550, and alternate embodiments described for the component module 550 may also be applicable to the component module 74. Furthermore, the component module 500 may include components not disclosed herein, or may omit one or more of the components disclosed herein.

Figure 46:
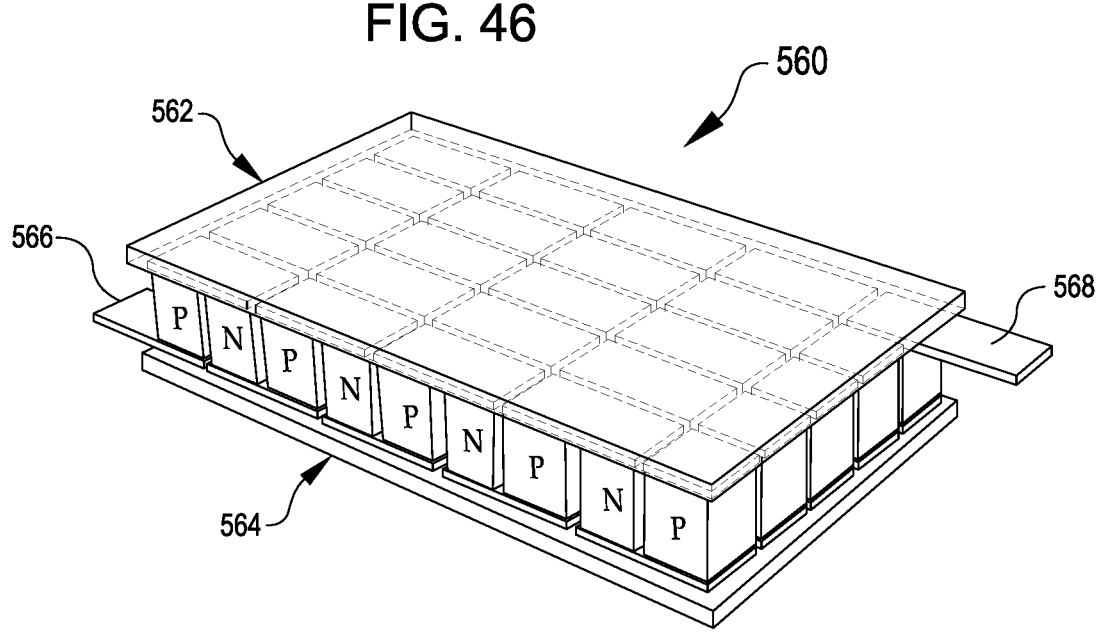
FIG. 46 is an isometric view of an energy-harvesting thermoelectric power source that the auxiliary power source of FIG. 45 can include, according to an embodiment.

FIG. 46 is an isometric view of a conventional thermoelectric couple (TEC) 560 of the auxiliary power source 112 of the component modules 74 and 550 (FIGS. 8 and 45), according to an embodiment. The TEC 560 is configured to harvest energy from the subject 405 (e.g., FIG. 38) while the subject is wearing the negative-pressure sleep-apnea treatment system 420 (FIGS. 26-32, 38, 42, and 44). The power supply 117 of the component modules 74 and 550 can be configured to receive the energy harvested by the TEC 560, and to convert the harvested energy into a power signal for powering one or more of the components of the component modules 74 and 550 and for charging the battery 110.

The TEC 560 is configured to convert a temperature differential between a "hot" side 562 and a "cold" side 564 into a current through, and a voltage across, conductive terminals 566 and 568. For example, the TEC 560 can be disposed in the sleep-apnea system 420 (FIGS. 26-32, 38, 42, and 44) such that the "hot" side 562 contacts a part (e.g., the neck 400) of the subject's body, and the "cold" side 564 is exposed to the air. Because the normal body temperature of a human subject is approximately 98.6° F., and because a typical room temperature is approximately 68° F., the temperature differential across the "hot" and "cold" sides 562 and 564 is approximately 30° F. In response to such a temperature differential, one or more TECs 560 configured to have, in aggregate, a "hot" side 562 having an effective area of approximately 100 square millimeters ($mm^2$), and a "cold" side 564 having an effective area of approximately 120 $mm^2$, can generate approximately 5 milliwatts (mW) of power. The one or more TECs 560 can be disposed, for example, in the straps 444 and 446 (FIG. 32) of the sleep-apnea system 420 such that the "hot" side 562 of each TEC is adjacent to, or in contact with, the subject's neck 400 (e.g., FIG. 38). Or, the one or more TECs 560 can be disposed along the inside surface 452 of the collar 440 (e.g., FIG. 31), in the sleeve 534 (FIG. 41), or remote from the sleep-apnea system 420 (e.g., in an article of clothing such as a shirt or hat). If disposed remote from the sleep-apnea system 420, then the one or more TECs 560 can transfer harvested power to the power supply 117 (FIGS. 8 and 45) via a wired or wireless connection.

Still referring to FIG. 46, further details of the TEC 560, and of other energy-harvesting devices that the auxiliary power source 112 (FIGS. 8 and 45) can include, are disclosed in Bhatnagar et al., *Energy Harvesting for Assistive and Mobile Applications*, Energy Science & Engineering, 3(3), pp. 153-173, (2015), which is incorporated herein by reference.

Figure 47:
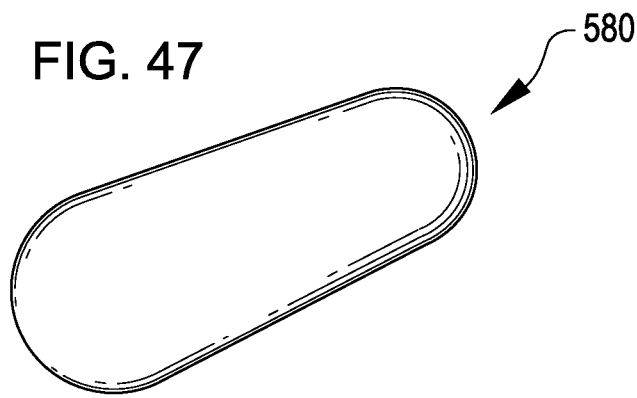
FIG. 47 is an isometric view of an element of an energy-harvesting motion power source that the auxiliary power source of FIG. 45 can include, according to an embodiment.

FIG. 47 is an isometric view of a shape-adaptive triboelectric nanogenerator (saTENG) unit 580, according to an embodiment.

Figure 48:
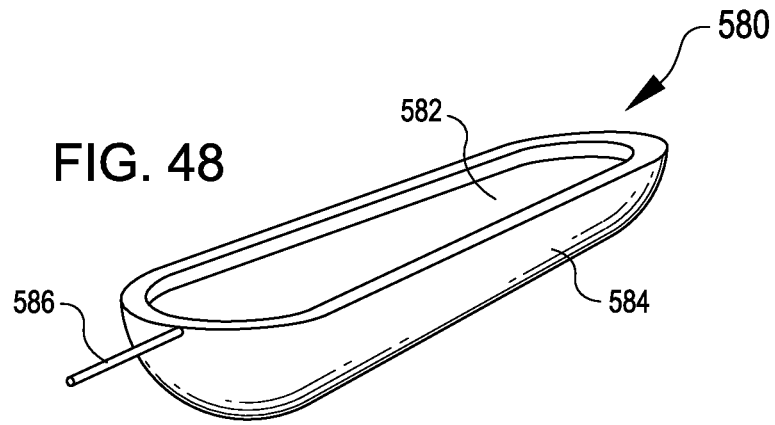
FIG. 48 is an isometric view of a bisection of the element of FIG. 47, according to an embodiment.

FIG. 48 is an isometric cutaway view of the saTENG unit 580 of FIG. 47, according to an embodiment.

Referring to FIGS. 47-48, the saTENG unit 580 includes a conductive liquid electrode 582 disposed inside of a rubber layer or shell 584. A conductor is inserted through an end of the shell 584 to provide a terminal or pin 586 for the electrode 582. Examples of substances from which the electrode 582 can be formed include water and a solution of sodium chloride (NaCl).

Figure 49:
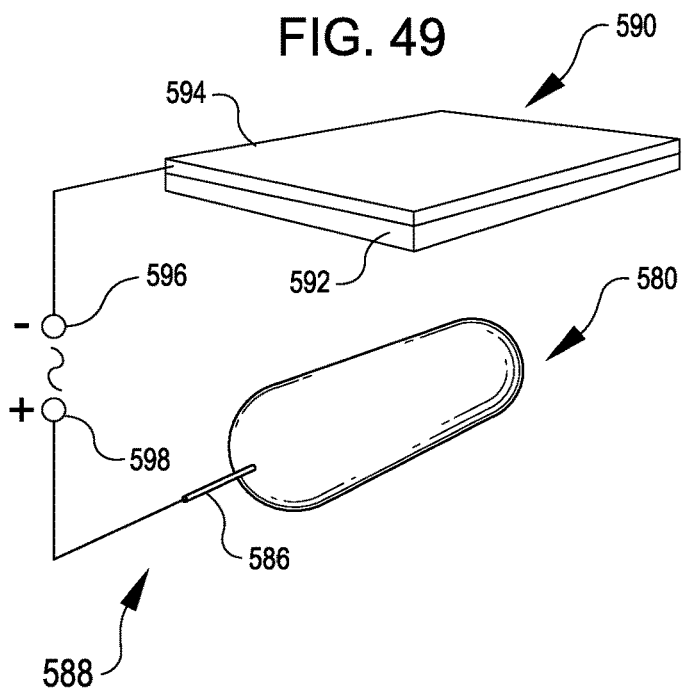
FIG. 49 is an isometric view of an energy-harvesting motion power source that includes the element of FIGS. 47-48, according to an embodiment.

FIG. 49 is an isometric view of a saTENG power generator 588, which includes the saTENG unit 580 of FIGS. 47-48, according to an embodiment. The auxiliary power source 112 of the component modules 74 and 550 (FIGS. 8 and 45) includes the power generator 588, which is configured to harvest energy from the subject 405 while he/she is wearing the negative-pressure sleep-apnea treatment system 420 (FIGS. 26-32, 38, 42, and 44). The power supply 117 (FIGS. 8 and 45) of the component modules 74 and 550 can be configured to receive the energy harvested by the power generator 588, and to convert the harvested energy into a power signal for powering one or more of the components of the component modules, and for charging the battery 110 (FIGS. 8 and 45) of the component modules.

In addition to the saTENG unit 580 (FIGS. 47-48), the power generator 588 includes an electrode 590 having a nylon layer 592 and an aluminum layer 594.

The power generator 588 is configured to convert motion and deformation (e.g., stretching and contracting) of the saTENG unit 580 relative to the electrode 590 into a current through, and a voltage across, conductive terminals 596 and 598. For example, one or more power generators 588 can be disposed in the sleep-apnea system 420 such that movement of the subject's body (e.g., movement cause by breathing or tossing and turning) causes the respective saTENG unit 580 in each of the one or more power generators to move or deform relative to the respective electrode 590. In response to such movement or deformation of the respective saTENG unit 580 in each of one or more power generators 588, the power generators are configured to generate power to the power supply 117 (FIGS. 8 and 45) as described above. The one or more power generators 588 can be disposed, for example, in the straps 444 and 446 (FIG. 32) of the sleep-apnea system 420. Or, the one or more power generators 588 can be disposed inside of, or can be otherwise secured to, the collar 440 (FIG. 31) or the sleeve 534 (FIG. 41), or can be located remote from the sleep-apnea system 420, e.g., in an article of clothing such as a shirt or hat. If disposed remote from the sleep-apnea system 420, then the one or more power generators 588 can be configured to transfer harvested power to the power supply 117 via a wired or wireless connection.

Referring again to FIGS. 47-49, further details of the saTENG unit 580, of the power generator 588, and of other energy-harvesting devices that the auxiliary power source 112 (FIGS. 8 and 45) can include, are disclosed in Yi et al., *A Highly Shape-Adaptive, Stretchable Design Based On Conductive Liquid For Energy Harvesting And Self-Powered Biomechanical Monitoring*, Sci. Adv., pp. 1-10, 17 Jun. 2016, which is incorporated herein by reference.

Figure 50:
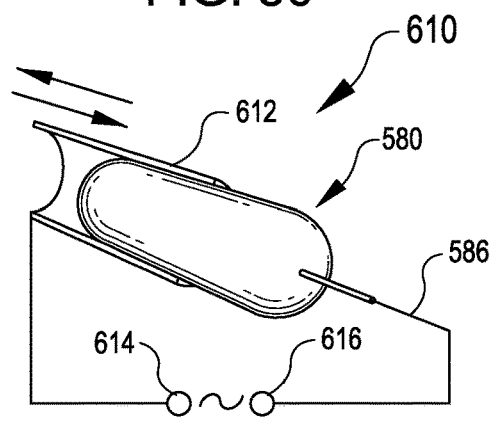
FIG. 50 is an isometric view of an energy-harvesting motion power source that includes the element of FIGS. 47-48, according to another embodiment.

FIG. 50 is an isometric view of a saTENG power generator 610, which includes the saTENG unit 580 of FIGS. 47-48, according to another embodiment. The auxiliary power source 112 of the component modules 74 and 550 (FIGS. 8 and 45) includes the power generator 610, which is configured to harvest energy from the subject 405 while he/she is wearing the negative-pressure sleep-apnea treatment system 420 (FIGS. 26-32, 38, 42, and 44). The power supply 117 (FIGS. 8 and 45) of the component modules 74 and 550 can be configured to receive the energy harvested by the power generator 610, and to convert the harvested energy into a power signal for powering one or more of the components of the component modules and for charging the battery 110 (FIGS. 8 and 45) of the component modules.

In addition to the saTENG unit 580 of FIGS. 47-48, the power generator 610 includes an aluminum electrode 612.

Figure 51:
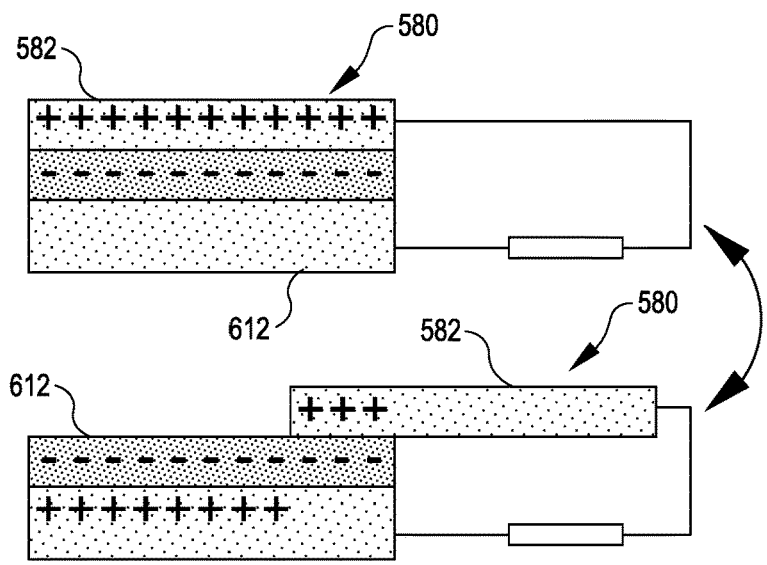
FIG. 51 is a diagram of an aspect of the operation of the energy-harvesting motion power source of FIG. 50, according to another embodiment.

FIG. 51 is a charge diagram for the power generator 610 of FIG. 50, the diagram showing how movement of the saTENG 580 relative to the electrode 612 displaces charge in electrodes 582 and 612, according to an embodiment. As described below, it is in response to this displacement of charge that the power generator 610 generates a current and a voltage.

Referring to FIGS. 50-51, the operation of the power generator 610 is described, according to an embodiment.

The power generator 610 is configured to convert motion and deformation (e.g., stretching and contracting) of the saTENG unit 580 relative to the electrode 612 into a current through, and a voltage across, conductive terminals 614 and 616 by displacing charge in the electrodes 582 (FIG. 48) and 612. For example, one or more power generators 610 can be disposed in the sleep-apnea system 420 such that movement of the subject's body (e.g., movement caused by breathing or tossing and turning) causes the respective saTENG unit 580 in each of the one or more power generators to move or deform relative to the respective electrode 612. In response to such movement or deformation of the respective saTENG unit 580 in each of one or more power generators 610, the power generators can generate power to the power supply 117 as described above. The one or more power generators 610 can be disposed, for example, in the straps 444 and 446 (FIG. 32) of the sleep-apnea system 420. Or, the one or more power generators 610 can be disposed inside of, or can be otherwise secured to, the collar 440 (FIG. 31) or the sleeve 534 (FIG. 41), or can be located remote from the sleep-apnea system 420, e.g., in an article of clothing such as a shirt or hat. If disposed remote from the sleep-apnea system 420, then the one or more power generators 610 can transfer harvested power to the power supply 117 (FIGS. 8 and 45) via a wired or wireless connection.

Still referring to FIGS. 50-51, further details of the power generator 610, and of other energy-harvesting devices that the auxiliary power source 112 (FIGS. 8 and 45) can include, are disclosed in Yi et al., *A Highly Shape-Adaptive, Stretchable Design Based On Conductive Liquid For Energy Harvesting And Self-Powered Biomechanical Monitoring*, Sci. Adv., pp. 1-10, 17 Jun. 2016, which is incorporated herein by reference.

Figure 52:
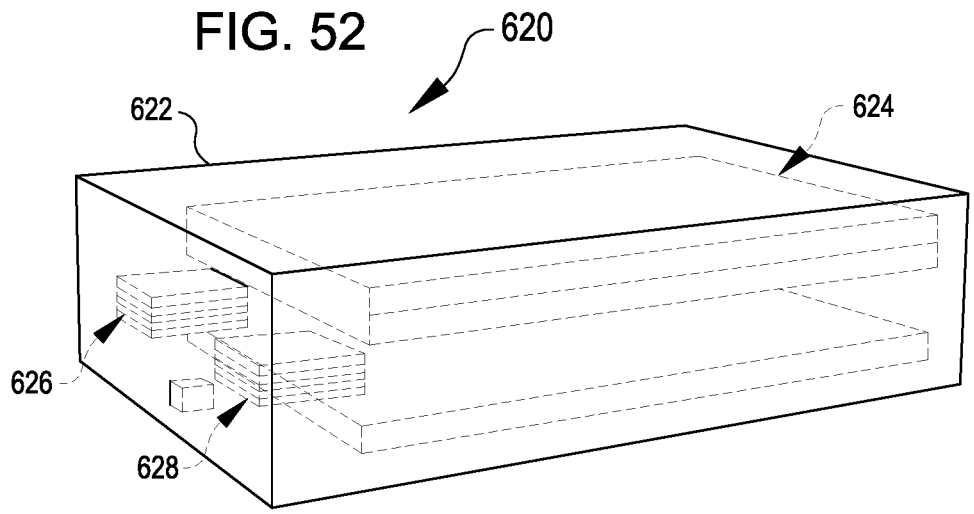
FIG. 52 is an isometric view of an energy-harvesting twist-stretch power source that the auxiliary power source of FIG. 45 can include, according to an embodiment.

FIG. 52 is an isometric transparent view of a TENG power generator 620, according to another embodiment. The auxiliary power source 112 of the component modules 74 and 550 (FIGS. 8 and 45) includes the power generator 620, which is configured to harvest energy from the subject 405 (e.g., FIG. 38) while he/she is wearing the negative-pressure sleep-apnea treatment system 420 (FIGS. 26-32, 38, 42, and 44). The power supply 117 (FIGS. 8 and 45) of the component modules 74 and 550 can be configured to receive the energy harvested by the power generator 620, and to convert the harvested energy into a power signal for powering one or more of the components of the component modules, and for charging the battery 110 (FIGS. 8 and 45) of the component modules.

The TENG power generator 620 includes a wrapper 622, a TENG 624 disposed in the wrapper, and at least one supercapacitor, here two equal-sized supercapacitors, 626 and 628, disposed in the wrapper and coupled to each other in electrical parallel to form, effectively, a single supercapacitor having a capacitance that is twice that of each of the supercapacitors 626 and 628. The wrapper 622 is configured to be stretchable, and can be made from any suitable material such as silicone rubber.

Figure 53:
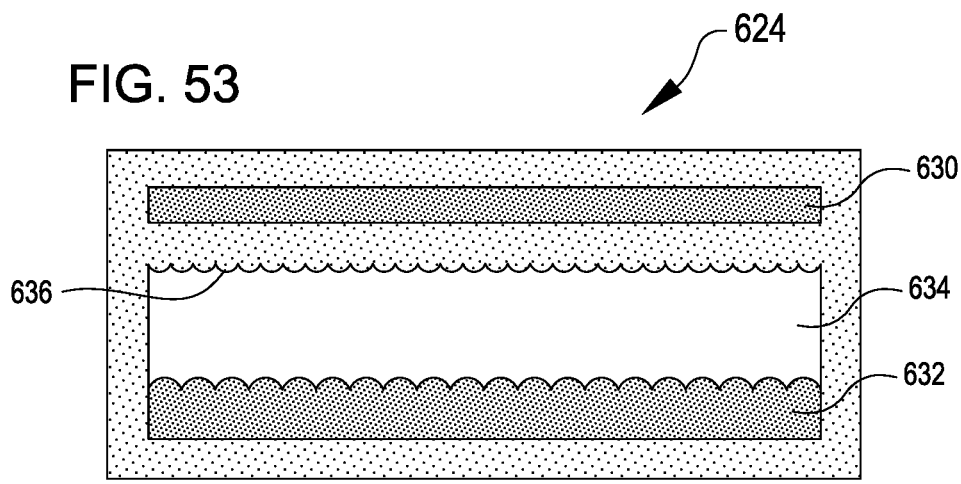
FIG. 53 is a cutaway side view of a triboelectric nano-generator (TENG) of the energy-harvesting twist-stretch power source of FIG. 52, according to an embodiment.

FIG. 53 is a cross section of the TENG 624 of FIG. 52, according to an embodiment. The TENG 624 includes two electrodes 630 and 632, a space 634 between the electrodes, and a portion 636 of the wrapper 622 disposed between the electrodes. The space 634 can be filled with any suitable material, such as air, and the electrodes 630 and 632 can be formed from any suitable material, such as a compound of carbon black (CB) and silicone rubber.

Figure 54:
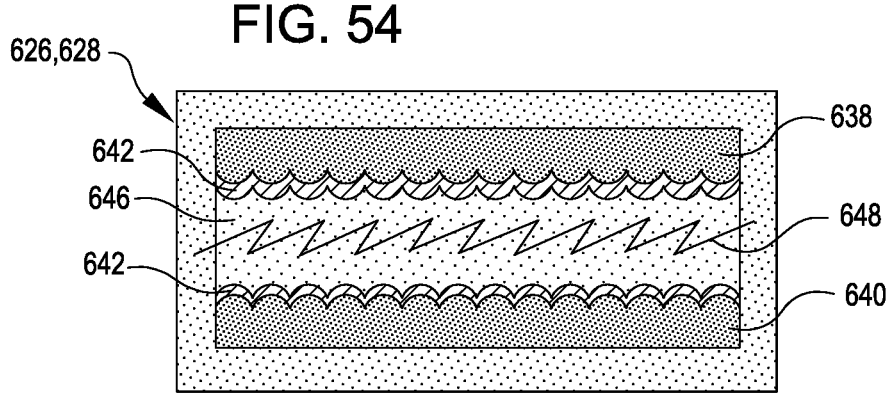
FIG. 54 is a cutaway side view of an energy-storing component of the energy-harvesting twist-stretch power source of FIG. 52, according to an embodiment.

FIG. 54 is a cross-sectional view of each of the supercapacitors 626 and 628 of FIG. 52, according to an embodiment. Each supercapacitor 626 and 628 includes two electrodes 638 and 640, a coating 642 on each of the electrodes, an electrolyte 646 disposed between the electrodes, and a wrinkled separator 648 disposed in the electrolyte. The electrodes 638 and 640 can be formed from any suitable material, such as the same material from which are formed the electrodes 630 and 632 of the TENG 624 of FIG. 53. The coating 642 can be formed from any suitable material, such as a composite of an active material (e.g., soluble polypyrrole (PPy)) and a conducting additive (e.g., carbon black).

The electrolyte 646 can be formed from any suitable material, such as a poly-vinyl-alcohol-(PVA)-phosphoric-acid-($H_3PO_4$) gel. And the separator 648, which prevents the electrodes 638 and 640 from short-circuiting together as the supercapacitors 626 and 628 are stretched or twisted, can be formed from any suitable material such as polyethylene.

Referring to FIGS. 52-54, the TENG power generator 620 is configured to generate power in response to the generator being deformed (e.g., stretched or twisted). In response to being deformed, the TENG 624 charges the supercapacitors 626 and 628, which, like a battery, are configured to generate a voltage and a current with the stored charge. For example, one or more power generators 620 can be disposed in the sleep-apnea system 420 (FIGS. 26-32, 38, 42, and 44) such that movement of the subject's body (e.g., movement cause by breathing or tossing and turning) causes the respective TENG 624 in each of the one or more power generators to deform. In response to such deformation of the respective TENG 624 in each of one or more power generators 620, the power generators can provide power to the power supply 117 (FIGS. 8 and 45) as described above. The one or more power generators 620 can be disposed, for example, in the straps 444 and 446 (FIG. 32) of the sleep-apnea system 420, considering that the straps may be subject to stretching and twisting, particularly while a subject is putting on, or taking of, the sleep-apnea system 420. Or, the one or more power generators 620 can be disposed inside of, or can be otherwise secured to, the collar 440 (FIG. 31) or the sleeve 534 (FIG. 41), or can be located remote from the sleep-apnea system 420, e.g., in an article of clothing such as a shirt or hat. If disposed remote from the sleep-apnea system 420, then the one or more power generators 630 can transfer harvested power to the power supply 117 (FIGS. 8 and 45) via a wired or wireless connection.

Still referring to FIGS. 52-54, further details of the power generator 620, and of other energy-harvesting devices that the auxiliary power source 112 (FIGS. 8 and 45) can include, are disclosed in Yi et al., *Stretchable And Waterproof Self-charging Power System For Harvesting Energy From Diverse Deformation And Powering Wearable Electronics*, American Chemical Society (ACS) Nano, 10, pp. 6519-6525, (2016), which is incorporated herein by reference.

Figure 55:
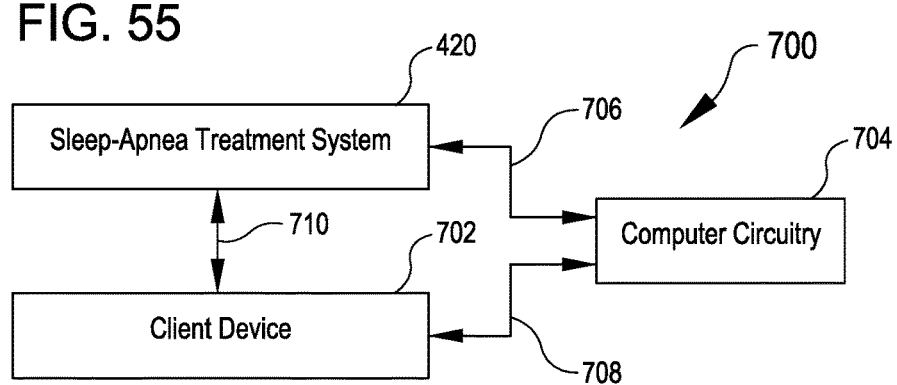
FIG. 55 is a block diagram of a system that includes the sleep-apnea-treament system of FIGS. 26-32, 42, and 44, a client, and computer circuitry that can correlate data obtained by the sleep-apnea-treatment system with data related to a subject who uses the sleep-apnea-treatment system, according to an embodiment.

FIG. 55 is a block diagram of a system 700, which includes the negative-pressure sleep-apnea-treatment system 420 (FIGS. 26-32, 38, 42, and 44), according to an embodiment. As described below, the system 700 can be configured to determine and to convey, to the subject 450, lifestyle changes for reducing the frequency or severity of sleep-apnea events that the subject experiences, and can be configured to determine and to convey, to the subject, adjustments to the subject's usage of the sleep-apnea system 420 for improving the subject's wellbeing (e.g., health).

In addition to the sleep-apnea system 420, the system 700 includes a client device 702 and computing circuitry 704. The computing circuitry 704 and the sleep-apnea system 420 are configured to communicate with each other via a wired or wireless channel (e.g., a wired or wireless bus) 706, the computing circuitry and the client device 702 are configured to communicate with each other via a wired or wireless channel 708, and the sleep-apnea system and the client device are configured to communicate with each other via a wired or wireless channel 710.

The client device 702 can include any device that is suitable for allowing the subject 405 (e.g., FIG. 38), the sensors 126 and 128 of the component modules 74 and 550 (FIGS. 8 and 45), or the sensors 554 of the component module 550 to input data related to the subject's lifestyle and wellbeing. Examples of the client device 702 include a client computer such as a laptop computer, a tablet computer, or a smart phone, or one or more sensors that can sense conditions and other parameters of the subject 405, such as blood pressure, mood, diet, degree of alertness, and whether the subject is awake or asleep.

And the computing circuitry 704 can include any circuitry that is suitable for determining, and conveying or implementing, changes to the subject's lifestyle to improve his/her sleep apnea, and changes to a subject's use of the sleep-apnea system 420 to improve his/her wellbeing. For example, the computing circuitry 704 can include specialized circuitry that is permanently configured to perform computations and tasks such as those described above and below. The computing circuitry 704 can also include circuitry, such as a microprocessor or microcontroller, that is configurable by software to perform computations and tasks such as those described above and below. Furthermore, the computing circuitry 704 can include circuitry, such as one or more field-programmable-gate arrays (FPGAs) or FPGA circuits, configurable by firmware to perform computations and tasks such as those described above and below. And the computing circuitry 704 can be local to the sleep-apnea system 420 and the client device 702, or can be part of a larger network such as the internet or the cloud.

Still referring to FIG. 55, alternate embodiments of the system 700 are contemplated. For example, one or both of the client device 702 and the computing circuitry 704 can be onboard the sleep-apnea system 420, and can be part of the component modules 74 and 550 (FIGS. 8 and 45) of the sleep-apnea system. Furthermore, the one or more sensors 554 (FIGS. 8 and 45) of the component module 74 can also act as, or be part of, the client device 702, and can be configured to sense one or more conditions or other parameters of the subject 405 that are indicative of the subject's lifestyle and wellbeing. Moreover, the system 700 can include the sleep-apnea treatment system 70 (FIGS. 4-8) instead of, or in addition to, the sleep-apnea treatment system 420.

Figure 56:
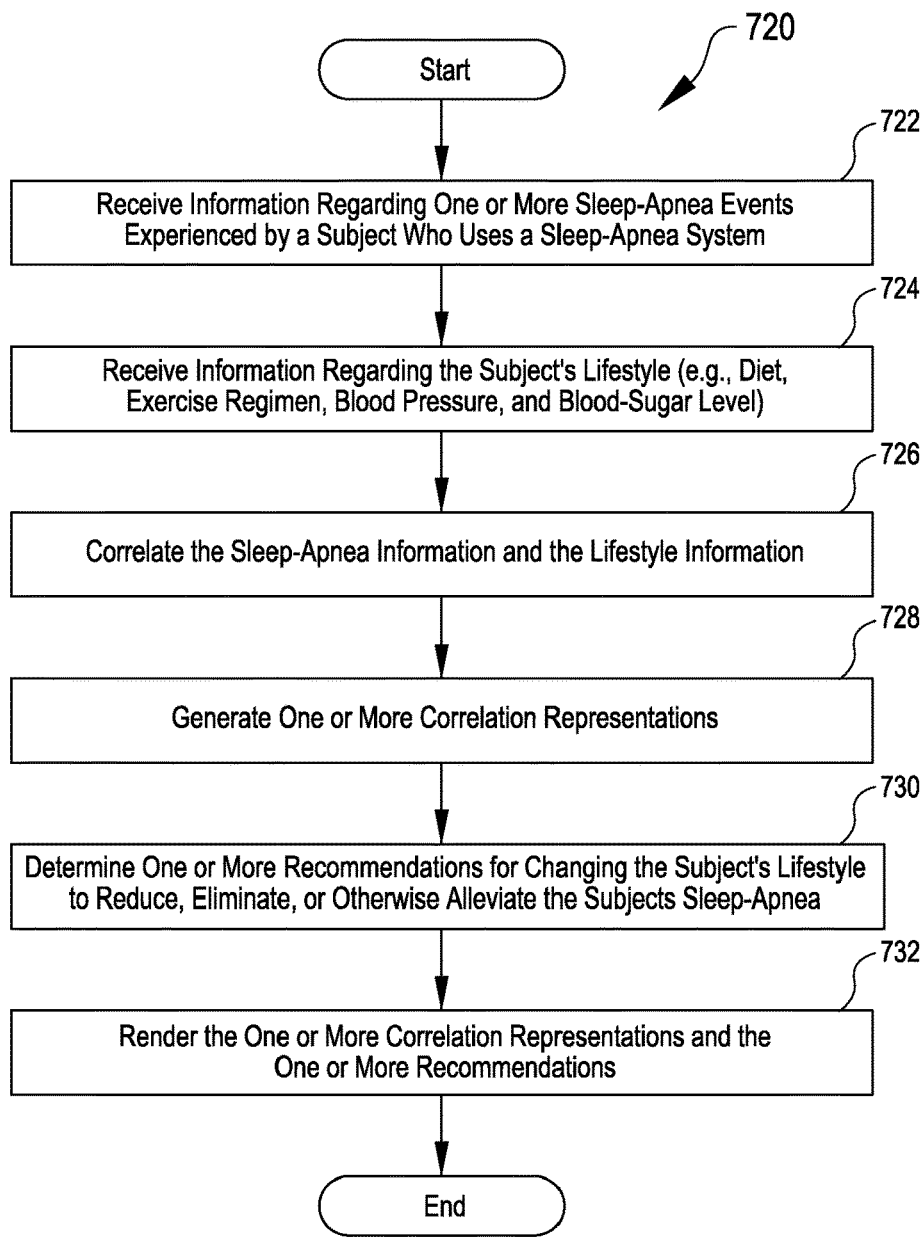
FIG. 56 is a flow diagram of an algorithm that can be executed by the system of FIG. 55 to determine changes to a subject's lifestyle that can improve the subject's sleep-apnea, according to an embodiment.

FIG. 56 is a flow diagram 720 of a procedure that the system 700 of FIG. 55 can be configured to implement for alleviating the subject's sleep apnea, according to an embodiment.

Referring to FIGS. 55-56, the procedure of the flow diagram 720 is described, according to an embodiment.

At a step 722, the computing circuitry 704 receives, from the sleep-apnea system 420, information regarding one or more sleep-apnea events experienced by the subject 405 (e.g., FIG. 38) over a period of time. For example, the sleep-apnea system 420 can be configured to detect, with one or more sensors of the sensor assembly 128 (FIGS. 8 and 45), one or more sleep-apnea events, and to determine, with the controller 134, one or more parameters of the one or more events. Examples of sleep-apnea events include airway obstructions and sleep-disturbances (e.g., a change in the subject's state of sleep, a change in the subject's duration of sleep, and other changes in the subject's sleep pattern) due to airway obstructions, and examples of parameters of sleep-apnea events include duration, frequency, and severity of the events (e.g., the percentage of the airway that is open or obstructed, the degree of change in the subject's sleep state, such as whether the subject woke up due to an event and how much the subject's sleep duration has changed from a benchmark duration). The sleep-apnea system 420 can be configured to store these determined parameters in the memory 130 (FIGS. 8 and 45), and to provide these stored parameters to the computing circuitry 704 automatically or in response to, e.g., a request from the computing circuitry.

Next, at a step 724, the computing circuitry 704 receives, from the client device 702, information regarding the subject's lifestyle. Examples of information regarding the subject's lifestyle include lifestyle parameters such as the subject's diet, meal times, snack times, exercise regimen including exercise frequency, exercise intensity, and exercise type, body weight, percentage of body fat, sleep schedule including number of hours of sleep per night, bed time, and out-of-bed time (the computing circuitry 704 may have already received this information from the sleep-apnea system 420), level of stress, habits (e.g., smoking, drinking too much alcohol, and taking nutritional supplements), blood pressure, blood-sugar level, medications taken, medication schedule, and electronics use including number of hours per day of use in bed before sleep or between sleep periods (e.g., wake up, use electronic device, then go back to sleep). For example, the subject 405, or another person, can enter this information via a keyboard of the client device 702, or the client device can include one or more sensors to sense such lifestyle parameters. The client device 702 can be configured to store these lifestyle parameters in a memory (not shown in FIG. 56), and to provide these stored parameters to the computing circuitry 704 automatically or in response to, e.g., a request from the computing circuitry.

Then, at a step 726, the computing circuitry 704 correlates the information received from the sleep-apnea system 420 regarding sleep-apnea events experienced by the subject 405 with the information received from the client device 702 regarding the subject's lifestyle. For example, the computing circuitry 704 can correlate the severity of airway obstructions to the subject's weight over a period of time, and can correlate the frequency of sleep-apnea events with a frequency or quantity at which the subject consumes a particular food or beverage, like coffee, over time. And in a further example, the computing circuitry 704 can correlate the severity of airway obstructions to the number of days per week that a subject exercises for more than 30 minutes.

Next, at a step 728, the computing circuitry 704 generates one or more plots, charts, graphs, or other representations of the correlations generated at step 726. For example, the computer circuitry 704 can generate a plot of the frequency of airway obstructions versus the average duration of the subject's exercise routines. These representations can be designed for display to the subject 405 or to another person (e.g., the subject's doctor) via a display device that, for example, is part of the client device 702. Or, these representations can be a data structure in a memory of the computing circuitry 704.

Then, at a step 730, the computing circuitry 704 determines, in response to the correlation representations generated at the step 728, recommendations of changes to the subject's lifestyle that may improve or eliminate the subject's sleep apnea. For example, if a correlation of the percentage of airway obstruction versus the subject's weight indicates that the average percentage of airway obstruction increases as the subject's weight increases, then the computing device 704 can generate a textual or audio message, for display/play via the client device 702, stating that if the subject 405 loses a particular number of pounds, then he/she can reduce the average percentage of airway obstruction by a particular amount. Or, if the correlation of average frequency of airway obstructions per night versus the number of cups of coffee the subject 405 drinks per day indicates the average frequency of airway obstructions per night increases as the number of cups of coffee per day increases, then the computing device 704 can generate a textual or audio message, for display/play via the client device 702, stating that if the subject 405 cuts back to no more than a particular number of cups of coffee per day, then he/she can reduce the average frequency of airway obstructions per night by a particular amount.

Next, at a step 732, the computing circuitry 704 renders (e.g., displays or plays) the one or more recommendations determined at the step 730 via a media-rendering device, such as the client device 702.

Still referring to FIG. 56, alternate embodiments of the procedure described in conjunction with the flow diagram 720 are contemplated. For example, the procedure can include one or more steps in addition to those described, or can omit one or more of the described steps 722-732. Furthermore, instead of generating recommendations based on the correlation data, the computing circuitry 704 can provide the correlation data to a doctor or to another healthcare professional, who can develop recommendations in response to the correlation data, and who can make the developed recommendations to the subject 405. Or, the computing circuitry 704 can provide the correlation data to the subject 405, who can draw his/her own conclusions from the data and adjust his/her lifestyle accordingly.

Figure 57:
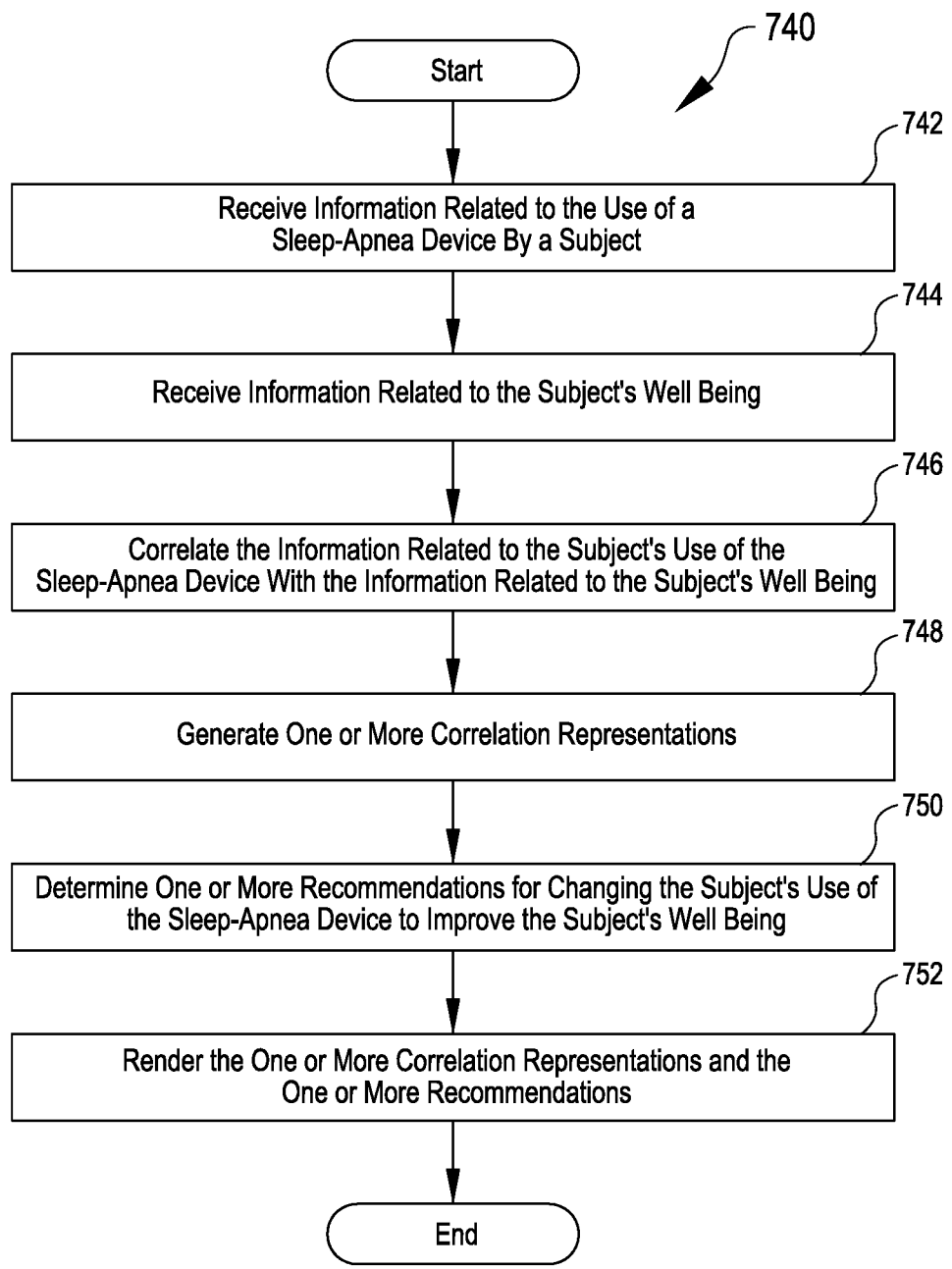
FIG. 57 is a flow diagram of an algorithm that can be executed by the system of FIG. 55 to determine changes that are related to a subject's use of a sleep-apnea-treatment device and that can improve the subject's wellbeing, according to an embodiment.

FIG. 57 is a flow diagram 740 of a procedure that the system 700 of FIG. 55 can be configured to implement for improving the subject's wellbeing, according to an embodiment.

Referring to FIGS. 55 and 57, the procedure of the flow diagram 740 is described, according to an embodiment.

At a step 742, the computing circuitry 704 receives, from the sleep-apnea system 420, information regarding the subject's use of the sleep-apnea system over a period of time. For example, the controller 134 (FIGS. 8 and 45) of the sleep-apnea system 420 can be configured to determine, in response to information sensed and provided by one or more sensors 126 and 128 of the component modules 74 and 550 (FIGS. 8 and 45), by one or more sensors 554 of the component module 550, or by other components of the component modules, parameters of the subject's use of the sleep-apnea system. Examples of parameters of use of the sleep-apnea system 420 include the average number of hours per night, and the average number of nights per week, that the subject 405 wears the sleep-apnea system, and the settings of the sleep-apnea system (e.g., maximum negative pressure, temperature within the pressure chamber, whether the sealant-dispenser assembly 124 (FIGS. 8 and 45) is active, a set wakeup time, and what parameters are sensed (e.g., breathing sound, breathing rate) to detect an apnea event). The sleep-apnea system 420 can be configured to store these determined parameters in the memory 130 (FIGS. 8 and 45), and to provide these stored parameters to the computing circuitry 704 automatically or in response to, e.g., a request from the computing circuitry.

Next, at a step 744, the computing circuitry 704 receives, from the client device 702, information regarding the subject's wellbeing. Examples of information regarding the subject's wellbeing include the subject's mental state, emotional state, level of daytime fatigue (e.g., the number of times per day the subject naps or "nods off"), and health parameters such as the subject's weight, percentage of body fat, blood pressure, blood-sugar level, blood-oxygen level, and levels of other substances (e.g., vitamins, minerals, and hormones) in the subject's body. For example, the subject 405, or another person, can enter this information via a keyboard of the client device 702, or the client device can include one or more sensors to sense such wellbeing parameters. The client device 702 can be configured to store these wellbeing parameters in a memory (not shown in FIGS. 55 and 57), and to provide these stored parameters to the computing circuitry 704 automatically or in response to, e.g., a request from the computing circuitry.

Then, at a step 746, the computing circuitry 704 correlates the information received from the sleep-apnea system 420 regarding the subject's use of the sleep-apnea system with the information received from the client device 702 regarding the subject's wellbeing. For example, the computing circuitry 704 can correlate the average number of hours per night that the subject 405 wears the sleep-apnea system 420 with the subject's blood pressure over a period of time, and can correlate the average number of nights per week that the subject wears the sleep-apnea system with the subject's reported level of daytime fatigue over a period of time.

Next, at a step 748, the computing circuitry 704 generates one or more plots, charts, graphs, or other representations of the correlations generated at the step 746. For example, the computer circuitry 704 can generate a plot of the average number of hours per night that the subject wears the sleep-apnea system 420 versus the subject's percentage of body fat. These representations can be designed for display to the subject 405, or to another person, via a display device that, for example, is part of the client device 702. Or, these representations can be a data structure in a memory of the computing circuitry 704.

Then, at a step 750, the computing circuitry 704 determines, in response to the correlation representations that it generated at the step 748, recommendations of changes to the subject's use of the sleep-apnea system 420 that may improve the subject's wellbeing. For example, if a correlation of the average number of nights that the subject uses the sleep-apnea system 420 versus the subject's weight indicates that the subject's weight increases as the average number of nights of use decreases, then the computing device 704 can generate a textual or audio message, for display/play via the client device 702, stating that if the subject 405 increases the number of days per week that he/she uses the sleep-apnea system 420 to a number that the computing device specifies, then he/she can lose a number of pounds within a range (e.g., 5-15 pounds) that the computing device specifies. Or, if the correlation of the average number of hours per night that the subject 405 uses the sleep-apnea system 420 versus the subject's blood pressure indicates that the subjects blood pressure increases as the average number of hours of use per night decreases, then the computing device 704 can generate a textual or audio message, for display/play via the client device 702, stating that if the subject increases the number of hours per night that he/she uses the sleep-apnea system 420 to a number that the computing device specifies (e.g., increase by two hours, from five hours to seven hours), then he/she can reduce his/her systolic blood pressure by an amount within a range (e.g., 5-15 millimeters of Mercury (mm Hg)).

Next, at a step 752, the computing circuitry 704 displays or otherwise renders the one or more recommendations determined at the step 750 via a media-rendering device, such as the client device 702.

Still referring to FIG. 57, alternate embodiments of the procedure described in conjunction with the flow diagram 740 are contemplated. For example, the procedure can include one or more steps in addition to those described, or can omit one or more of the described steps 742-752. Furthermore, instead of generating recommendations based on the correlation data, the computing circuitry 704 can provide the correlation data to a doctor or other healthcare professional, who can develop and make recommendations to the subject 405 in response to the correlation data. Or, the computing circuitry 704 can provide the correlation data to the subject 405, who can draw his/her own conclusions from the data and adjust his/her usage of the sleep-apnea system 420 accordingly.

Figure 58:
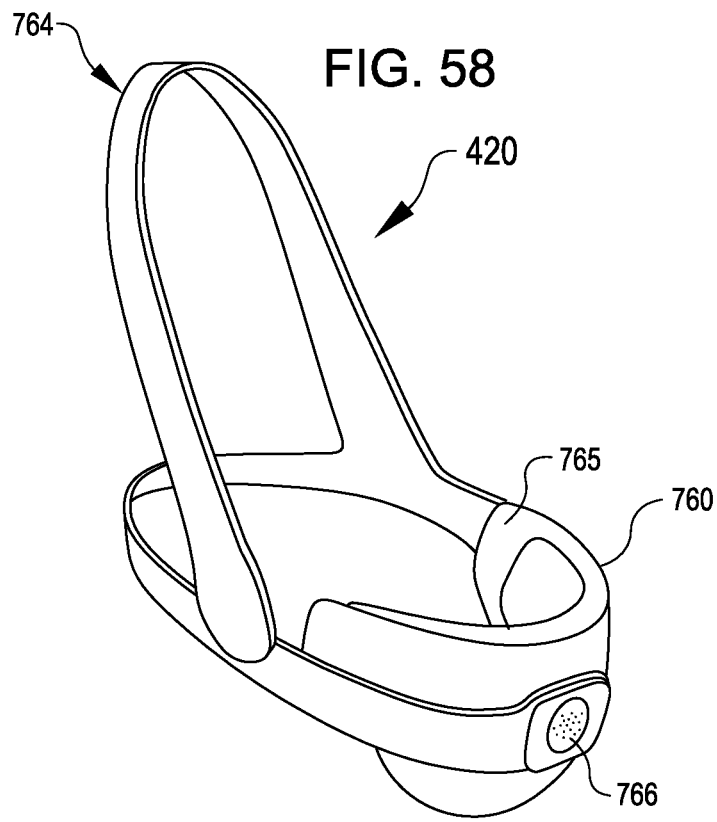
FIGS. 58-59 are isometric views of a sleep-apnea-treatment system, according to another embodiment.

FIG. 58 is an isometric view of the negative-pressure sleep-apnea-treatment system 420, according to another embodiment.

Figure 59:
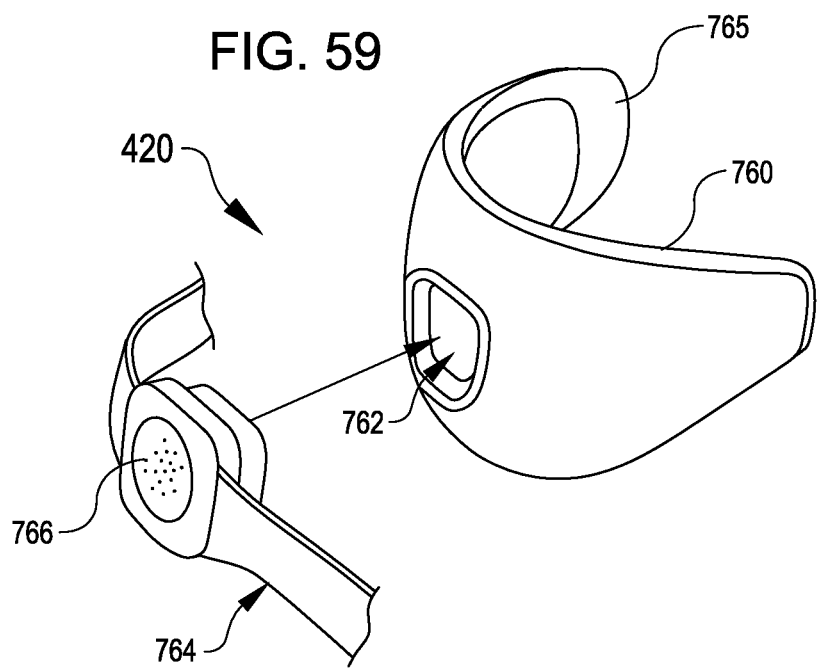

FIG. 59 is an isometric exploded view of the sleep-apnea-treatment system 420 of FIG. 58, according to an embodiment.

Referring to FIGS. 58-59, the sleep-apnea system 420 includes a collar assembly 760 having a receptacle 762, a strap assembly 764 configured to secure the sleep-apnea system to the subject's neck 400 (e.g., FIG. 38), a gasket assembly 765 configured to make an airtight seal with the subject's neck, and a component module 766 attached to the strap assembly and configured to fit into the receptacle while the subject is wearing the sleep-apnea system. Other than having the receptacle 762, the collar assembly 760 can be similar to the collar assembly 440 (e.g., FIGS. 30-37), the strap assembly 764 can be made from a material that is similar to the material from which the strap assembly 424 (e.g., FIGS. 30-32), is made, and the gasket assembly 765 can be similar to the gasket assembly 422 (FIGS. 27-28, 30-34, and 39-40). And other than being configured to fit into the receptacle 762, the component module 766 can be structurally and functionally similar to the component module 550 (FIG. 45).

Still referring to FIGS. 58-59, alternate embodiments of the sleep-apnea system 420 are contemplated. For example, a remote-control device, such as the remote-control device 484 (FIG. 37), can be configured to program, to receive and to analyze the status of, and to otherwise control, the sleep-apnea system 420. The remote-control device 484 can be part of, or separate from, the sleep-apnea system 420.

Figure 60:
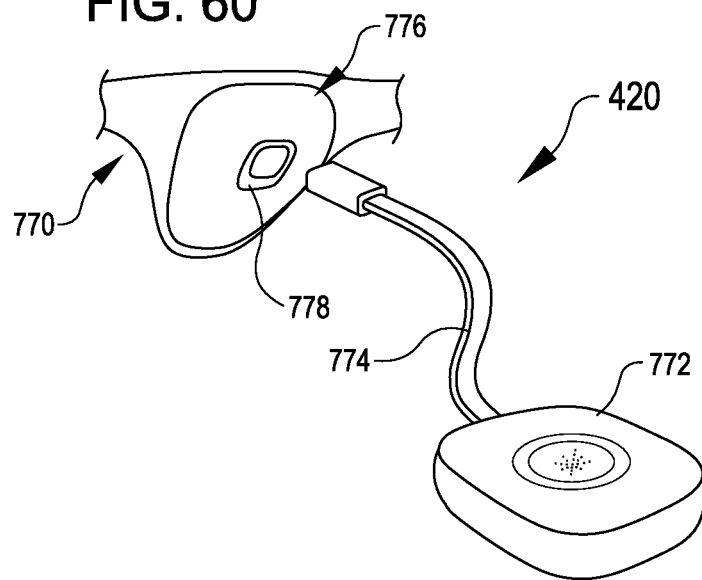
FIG. 60 is an isometric view of a sleep-apnea-treatment system, according to yet another embodiment.

FIG. 60 is an isometric view of the negative-pressure sleep-apnea-treatment system 420, according to yet another embodiment.

The sleep-apnea system 420 includes a wearable unit 770, a base unit 772, and an air hose 774 configured for pneumatically coupling the wearable unit to the base unit. The wearable unit 770 includes a collar assembly 776 having a hose connector 778, a strap assembly (not shown in FIG. 60) configured to secure the wearable unit 770 around the subject's neck 400 (e.g., FIG. 38), and a gasket assembly (not shown in FIG. 60) configured to form an airtight seal with the subject's neck. The base unit 772 includes at least a motor assembly and a pump assembly (not shown in FIG. 60), such as the motor assembly 116 and the pump assembly 118 of FIG. 45, and is configured to generate a negative pressure within a pressure chamber (not shown in FIG. 60) between an inner surface of the collar assembly 776 and the subject's neck 400 by drawing a vacuum in the pressure chamber via the connector 778, the hose 774, and another hose connector (not shown in FIG. 60) located on the base unit. Other than having the hose connector 778, the collar assembly 776 can be similar to the collar assembly 440 (e.g., FIGS. 30-37), the strap assembly can be similar to the strap assembly 424 (e.g., FIGS. 30-32), and the gasket assembly can be similar to the gasket assembly 422 (FIGS. 27-28, 30-34, and 39-40). In addition to the pump and motor assemblies 116 and 118, the base unit 772 can include one or more other components of the component module 550 (FIG. 45), and can include a power supply (not shown in FIG. 60) that allows "plugging" the base unit into a wall outlet that provides 110 or 220 VAC. Moreover, the collar assembly 776 also can include one or more components of the component module 550, such as components of the module that the base unit 772 lacks.

Still referring to FIG. 60, alternate embodiments of the sleep-apnea system 420 are contemplated. For example, a remote-control device, such as the remote-control device 484 (FIG. 37), can be configured to program, to receive and to analyze the status of, and to otherwise control the sleep-apnea system 420. The remote-control device 484 can be part of, or separate from, the sleep-apnea system 420.

Figure 61:
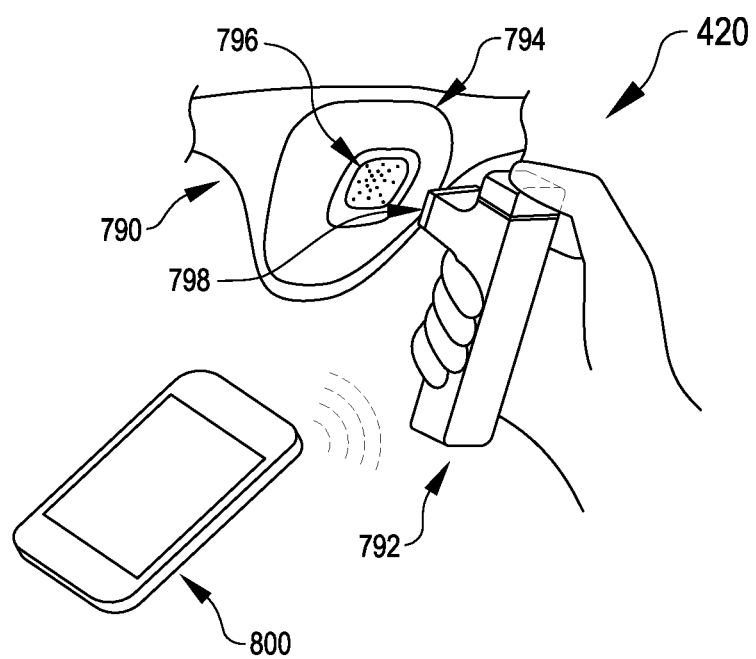
FIG. 61 is an isometric view of a sleep-apnea-treatment system, according to still another embodiment.

FIG. 61 is an isometric view of the negative-pressure sleep-apnea-treatment system 420, according to still another embodiment.

The sleep-apnea system 420 includes a wearable unit 790, and a hand-held unit 792 for pressurizing, with negative pressure, a pressure chamber (not shown in FIG. 61) adjacent to a region, e.g., the throat region 406 or throat region 407 (FIGS. 24-25), of the subject's throat. The wearable unit 790 includes a collar assembly 794 having a pneumatic connector 796, a strap assembly (not shown in FIG. 61) configured to secure the wearable unit 790 around a subject's neck 400 (e.g., FIG. 38), and a gasket assembly (not shown in FIG. 61) configured to form an airtight seal with the subject's neck. The hand-held unit 792 includes a pneumatic connector 798 and at least a motor assembly and a pump assembly (not shown in FIG. 60), such as the motor assembly 116 and the pump assembly 118 (FIG. 45), and is configured to generate a negative pressure within a pressure chamber between an inner surface of the collar assembly 794 and the subject's neck 400 by drawing a vacuum in the pressure chamber via the connectors 796 and 798. The collar assembly 794 and the gasket assembly of the sleep-apnea system 420 are designed to hold the negative pressure in the pressure chamber for a period of time (e.g., one or more hours, or the entire time that the subject is sleeping). If the magnitude of the negative pressure decreases to or below a threshold pressure, then circuitry onboard the collar assembly 794 can sound an alarm to notify the subject 405 (e.g., FIG. 38) that he/she should use the hand-held unit 792 to reestablish the proper pressure within the pressure chamber. Or, the collar assembly 794 can be configured to transmit to the hand-held unit 792 information sufficient for the hand-held unit to determine that the magnitude of the negative pressure has decreased to or below the threshold pressure; in response to this determination, the hand-held unit can sound the above-mentioned alarm. Other than having the pneumatic connector 796, the collar assembly 794 can be similar to the collar assembly 440 (e.g., FIGS. 30-37), the strap assembly can be similar to the strap assembly 424 (e.g., FIGS. 30-32), and the gasket assembly can be similar to the gasket assembly 422 (FIGS. 27-28, 30-34, and 39-40). In addition to the pump and motor assemblies 116 and 118, the hand-held unit 792 can include one or more other components of the component module 550 (FIG. 45), and can include a power supply (not shown in FIG. 60) that allows "plugging" the hand-held unit into a wall outlet that provides 110 or 220 VAC. Moreover, the collar assembly 794 also can include one or more components of the component module 550, such as components of the module that the hand-held unit 792 lacks.

Still referring to FIG. 61, alternate embodiments of the sleep-apnea system 420 are contemplated. For example, a remote-control device 800, which can be similar to the remote-control device 484 (FIG. 37), can be configured to program, to receive and to analyze the status of, and to otherwise control, the hand-held unit 792 of the sleep-apnea system 420. The remote-control device 800 can be part of, or separate from, the sleep-apnea system 420.

Figure 62:
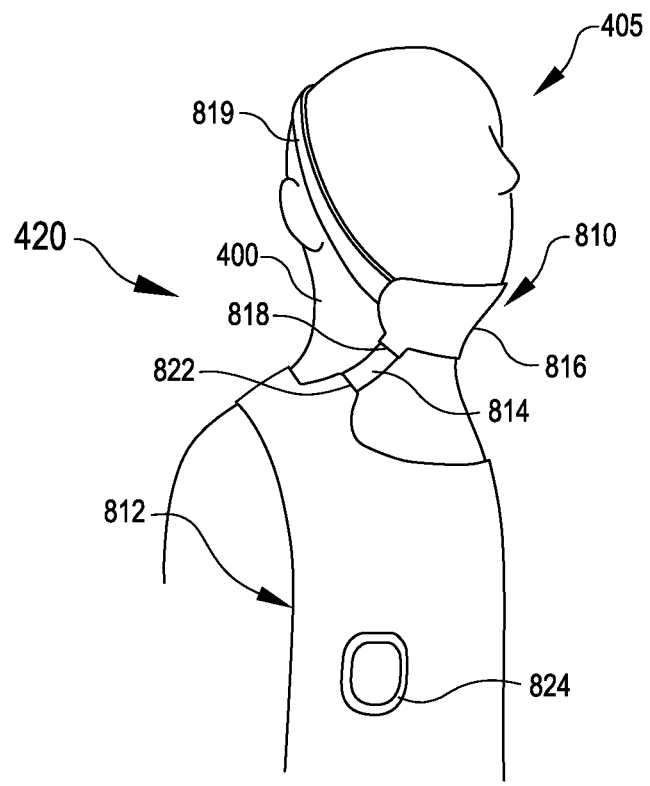
FIG. 62 is an isometric view of a subject wearing a sleep-apnea-treatment system, according to another embodiment.

FIG. 62 is an isometric view of the subject 405 wearing the negative-pressure sleep-apnea-treatment system 420, according to another embodiment.

The sleep-apnea system 420 includes a wearable unit 810, a garment unit 812, and an air hose 814 configured for pneumatically coupling the wearable unit to the garment unit. The wearable unit 810 includes a collar assembly 816 having a hose connector 818, a strap assembly 819 configured to secure the wearable unit 810 around the subject's neck 400, and a gasket assembly (not shown in FIG. 62) configured to form an airtight seal with the subject's neck. The garment unit 812 includes a hose connector 822 and at least a motor assembly and a pump assembly (not shown in FIG. 62), such as the motor assembly 116 and the pump assembly 118 (FIG. 45), and is configured to generate a negative pressure within a pressure chamber (not shown in FIG. 62) between an inner surface of the collar assembly 816 and the subject's neck 400 by drawing a vacuum in the pressure chamber via the hose 814 and the connectors 818 and 822. Other than having the hose connector 818, the collar assembly 816 can be similar to the collar assembly 440 (e.g., FIGS. 30-37), the strap assembly 819 can be similar to the strap assembly 424 (e.g., FIGS. 30-32), and the gasket assembly can be similar to the gasket assembly 422 (FIGS. 27-28, 30-34, and 39-40). The garment unit 812 can be any wearable item, such as an undergarment, shirt, pants, arm band, or hat, and can be made from any suitable material. In addition to the pump and motor assemblies 116 and 118, the garment unit 812 can include one or more other components of the component module 550 (FIG. 45), and can include a power supply (not shown in FIG. 60) that allows "plugging" the garment unit into a wall outlet that provides 110 or 220 VAC. For example, the garment unit 812 can include a module 824, which can be similar to the module 550, and can have one or more of the sensors 126, 128, and 554 (FIG. 45) disposed at suitable locations of the garment unit. Such one or more sensors 126, 128, and 554 can be located on the inner surface (the side facing the subject 405 when worn) of the garment, inside of the garment, or on the outer surface (the side facing away from the subject when worn) of the garment. Moreover, the collar assembly 816 also can include one or more components of the component module 550, such as components of the module that the garment unit 812 lacks.

Still referring to FIG. 62, alternate embodiments of the sleep-apnea system 420 are contemplated. For example, a remote-control device, such as the remote-control device 484 (FIG. 37), can be configured to program, to receive and to analyze the status of, and to otherwise control the sleep-apnea system 420. The remote-control device can be part of, or separate from, the sleep-apnea system 420.

Figure 63:
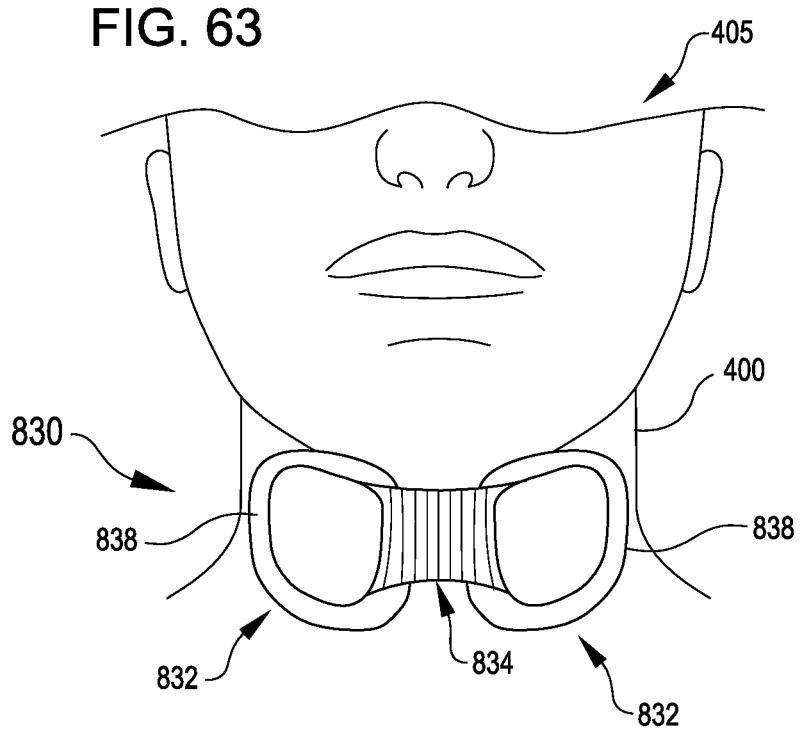
FIG. 63 is an isometric view of a subject wearing a sleep-apnea-treatment system, according to yet another embodiment.

FIG. 63 is an isometric view of a negative-pressure sleep-apnea-treatment system 830, according to an embodiment.

The sleep-apnea system 830 includes multiple pressure-chamber units 832 (two units in this embodiment), an elastic coupler 834 disposed between, and coupling together, the pressure-chamber units, and a strap assembly (not shown in FIG. 63) configured for securing around the back of the subject's neck 400 to hold the pressure-chamber units in place against the neck and throat of the subject 405. Each pressure-chamber unit 832 includes a gasket assembly 838 configured to form an airtight seal against the subject's neck 400, at least a motor assembly and a pump assembly (not shown in FIG. 63), such as the motor assembly 116 and the pump assembly 118 (FIG. 45), and is configured to generate a negative pressure within a pressure chamber (not shown in FIG. 63) between an inner surface of the pressure-chamber unit 832 and the subject's throat by drawing a vacuum in the pressure chamber. For example, each unit 832 can include a component module (not shown in FIG. 63) such as the component module 550 (FIG. 45). Alternatively, one of the units 832 can contain at least one component of the module 550, and the other pressure-chamber unit can include at least one other component of the module 550, and the pressure-chamber units can communicate with each other electrically or pneumatically via one or more respective conduits (not shown in FIG. 63) disposed in or on the elastic coupler 834. Other than having a different size and a different shape, each pressure-chamber unit 832 can be similar to the collar assembly 440 (e.g., FIGS. 30-37), the strap assembly can be similar to the strap assembly 424 (e.g., FIGS. 30-32), and the gasket assembly can be similar to the gasket assembly 422 (FIGS. 27-28, 30-34, and 39-40). And the elastic coupler 834 can be formed from any suitable material, such as the same material from which the strap assembly is formed.

Still referring to FIG. 63, alternate embodiments of the sleep-apnea system 830 are contemplated. For example, a remote-control device, such as the remote-control device 484 (FIG. 37), can be configured to program, to receive and to analyze the status of, and to otherwise control the sleep-apnea system 830. The remote-control device can be part of, or separate from, the sleep-apnea system 830.

From the foregoing it will be appreciated that, although specific embodiments have been described herein for purposes of illustration, various modifications may be made without deviating from the spirit and scope of the disclosure. Furthermore, it is contemplated that any feature disclosed in conjunction with an embodiment can be incorporated into any other embodiment. For example, any feature disclosed in conjunction with an embodiment of the sleep-apnea-treatment system 70 can be incorporated into any embodiment of the sleep-apnea-treatment systems 420 and 830, and vice-versa. Moreover, where an alternative is disclosed for a particular embodiment, this alternative may also apply to other embodiments even if not specifically stated. For example, one or more of the above-described techniques can be implemented in a sleep-apnea-treatment system (e.g., a CPAP system) other than the sleep-apnea-treatment systems 70, 420, and 830. In addition, one or more of the above-described techniques may be modified for implementation on a system (e.g., a CPAP system) that treats sleep apnea with positive pressure instead of negative pressure. Furthermore, it is contemplated that a system may treat sleep apnea with both positive and negative pressure using one or more of the above-described techniques. Moreover, "and" and "or" are to be interpreted as follows. A "or" B, and A "and" B, are to be interpreted as meaning A, B, or both A and B, unless otherwise indicated expressly or implicitly by, e.g., context.

While various aspects and embodiments have been disclosed herein, other aspects and embodiments will be apparent to those skilled in the art from the detailed description provided herein. The various aspects and embodiments disclosed herein are for purposes of illustration and are not intended to be limiting, with the true scope and spirit being indicated by the following claims.

The invention claimed is:

1. A system, comprising:
 a collar configured to maintain an airway of a subject open while the subject is sleeping by applying to a throat of the subject a negative pressure having a magnitude;
 a pump configured to generate the negative pressure;
 a motor configured to drive the pump;
 a sensor configured to generate a first sense signal that is related to a degree to which the airway is open; and
 a controller configured
  to determine at least one dimension of the airway in response to the first sense signal,
  to determine the degree to which the airway is open at least in part in response to the determined at least one dimension of the airway, and
  to vary the magnitude of the negative pressure in response to the determined degree to which the airway is open.

2. The system of claim 1, wherein the pump, motor, sensor, and controller are secured to the collar.

3. The system of claim 1, further comprising:
 a base unit including the pump, the motor, the sensor, a memory, and the controller; and
 a hose configured to couple the base unit to the collar.

4. The system of claim 1 wherein the collar is configured to apply the negative pressure to a region of the throat above a sternal head of the subject, below an anterior belly of Digastricus of the subject, and between sternocleidomastoid muscles of the subject.

5. The system of claim 1 wherein the collar is configured to apply the negative pressure to a region of the throat above a thyroid cartilage of the subject, below an anterior belly of Digastricus of the subject, and between sternocleidomastoid muscles of the subject.

6. The system of claim 1, further comprising a flexible sleeve that is configured to be removably disposable between the collar and the throat of the subject.

7. The system of claim 1, further comprising:
 wherein the collar has a perimeter; and
 a gasket assembly disposed around the perimeter and having a surface configured to form a seal with a neck of the subject, the surface including openings through which the pump is configured to pull air to draw the gasket assembly against the neck.

8. The system of claim 1 wherein the sensor includes a reflective sensor configured:
 to transmit electromagnetic energy toward the subject;
 to receive a portion of the transmitted electromagnetic energy redirected by the subject; and
 to generate the sense signal related to a received portion of the transmitted electromagnetic energy redirected by the subject.

9. The system of claim 1 wherein the sensor includes a pulse oximetry sensor configured to generate the sense signal related to a level of oxygen in blood of the subject.

10. The system of claim 1 wherein the sensor includes a microphone configured to generate the sense signal related to a level of sound generated by the subject.

11. The system of claim 1 wherein the sensor includes an accelerometer configured to generate the sense signal related to a level of movement of the subject.

12. The system of claim 1 wherein the sensor includes a gas sensor configured to generate the sense signal related to a level of a substance in air expired by the subject.

13. The system of claim 1 wherein the sensor includes electrodes configured to contact a neck of the subject and to generate the sense signal related to a current flowing into or out from one of the electrodes.

14. The system of claim 1 wherein the sensor includes electrodes configured to contact a neck of the subject and to generate the sense signal related to a voltage across the electrodes.

15. The system of claim 1, further comprising:
a light sensor configured to generate a second sense signal related to a level of ambient light; and
wherein the controller is configured to vary the magnitude of the negative pressure at least in part in response to the second sense signal.

16. The system of claim 1, further comprising:
a power source;
a heating-cooling assembly secured to the collar, coupled to the power source, and configured to heat and to cool a region of a neck of the subject; and
wherein the controller is configured to cause the heating-cooling assembly to change a temperature of the region of the neck of the subject in response to the sense signal.

17. The system of claim 1, further comprising:
a power source secured to the collar; and
a power supply secured to the collar and configured
to convert energy from the power source to a power signal, and
to provide the power signal to one of the motor, sensor, and controller.

18. The system of claim 1, further comprising a power source secured to the collar and configured to generate energy in response to movement of the subject.

19. The system of claim 1, further comprising:
a tactile switch disposed adjacent to a side of the collar, the side configured to face away from the subject, the tactile switch having on and off states; and
a power supply secured to the collar and configured
to provide power from a power source to one of the motor, sensor, and controller in response to the tactile switch having the on state; and
to withhold power to one of the motor, sensor, and controller in response to the tactile switch having the off state.

20. The system of claim 1, further comprising a vacuum sensor secured to the collar and configured:
to generate a signal that is related to the magnitude of the negative pressure, and to provide the signal to the controller.

21. The system of claim 1, further comprising:
a memory configured to store degrees to which the airway is open; and
wherein the controller is configured to determine the degree to which the airway is open by determining which of the stored degrees to which the airway is open corresponds to the sense signal.

22. A system, comprising:
a collar configured to maintain an airway of a subject open while the subject is sleeping by applying to a throat of the subject a negative pressure having a magnitude;
a pump configured to generate the negative pressure;
a motor configured to drive the pump;
a sensor configured to generate a sense signal that is related to a degree to which the airway is open;
a controller configured to vary the magnitude of the negative pressure in response to the sense signal; and
a power source secured to the collar and configured to generate energy in response to a temperature differential.

23. A system, comprising:
a collar configured to maintain an airway of a subject open while the subject is sleeping by applying to a throat of the subject a negative pressure having a magnitude;
a pump configured to generate the negative pressure;
a motor configured to drive the pump;
a sensor configured to generate a sense signal that is related to a degree to which the airway is open;
a controller configured to vary the magnitude of the negative pressure in response to the sense signal; and
a power source secured to the collar and configured to generate energy in response to an electromagnetic wave incident on the collar.

24. A method, comprising:
maintaining an airway of a subject open while the subject is sleeping by applying a negative pressure having a magnitude to a region of a throat of the subject above a sternal head of the subject, below an anterior belly of Digastricus of the subject, and between sternocleidomastoid muscles of the subject;
determining a level of movement of the subject;
determining a degree to which the airway is open at least in part in response to a determined level of movement of the subject; and
adjusting the magnitude of the negative pressure in response to a determined degree to which the airway is open.

25. The method of claim 24, further comprising:
forming a seal around the region of the throat with a gasket assembly disposed around a perimeter of a collar that is held against the throat of the subject, the gasket assembly having a surface configured to form a seal with a neck of the subject, the surface including openings; and
enhancing the seal by drawing a fluid through the openings.

26. The method of claim 24 wherein determining the degree to which the airway is open includes:
determining a level of oxygen in blood of the subject; and
determining the degree to which the airway is open at least in part in response to a determined level of oxygen in the blood of the subject.

27. The method of claim 24 wherein determining the degree to which the airway is open includes:
determining a level of sound made by the subject; and
determining the degree to which the airway is open at least in part in response to a determined level of sound made by the subject.

28. The method of claim 24 wherein determining the degree to which the airway is open includes:
determining a stroke volume of a heart of the subject; and
determining the degree to which the airway is open at least in part in response to a determined stroke volume of the heart of the subject.

29. A method, comprising:
maintaining an airway of a subject open while the subject is sleeping by applying a negative pressure having a magnitude to a region of a throat of the subject above a sternal head of the subject, below an anterior belly of Digastricus of the subject, and between sternocleidomastoid muscles of the subject;
determining a cross-sectional area of the airway of the subject;
determining a degree to which the airway is open in response to a determined cross-sectional area of the airway of the subject; and
adjusting the magnitude of the negative pressure in response to a determined degree to which the airway is open.

30. A non-transitory computer-readable medium storing instructions that, when executed by a computing machine, cause the computing machine, or an apparatus under control of the computing machine:

to maintain an airway of a subject open while the subject is sleeping by applying a negative pressure having a magnitude to a region of a throat of the subject above a sternal head of the subject, below an anterior belly of Digastricus of the subject, and between sternocleidomastoid muscles of the subject;

to determine a level of movement of the subject;

to determine a degree to which the airway is open in response to a determined level of movement of the subject; and to adjust the magnitude of the negative pressure in response to a determined degree to which the airway is open.

31. A non-transitory computer-readable medium storing instructions that, when executed by a computing machine, cause the computing machine, or an apparatus under control of the computing machine:

to maintain an airway of a subject open while the subject is sleeping by applying a negative pressure having a magnitude to a region of a throat of the subject above a sternal head of the subject, below an anterior belly of Digastricus of the subject, and between sternocleidomastoid muscles of the subject;

to determine a cross-sectional area of the airway of the subject;

to determine a degree to which the airway is open in response to a determined cross-sectional area of the airway of the subject; and to adjust the magnitude of the negative pressure in response to a determined degree to which the airway is open.

\* \* \* \* \*